US008016757B2

(12) United States Patent
Kaczkowski et al.

(10) Patent No.: US 8,016,757 B2
(45) Date of Patent: Sep. 13, 2011

(54) NON-INVASIVE TEMPERATURE ESTIMATION TECHNIQUE FOR HIFU THERAPY MONITORING USING BACKSCATTERED ULTRASOUND

(75) Inventors: Peter J. Kaczkowski, Seattle, WA (US); Ajay Anand, Elmsford, NY (US)

(73) Assignee: University of Washington, Seattle, WA (US)

( * ) Notice: Subject to any disclaimer, the term of this patent is extended or adjusted under 35 U.S.C. 154(b) by 1384 days.

(21) Appl. No.: 11/537,416

(22) Filed: Sep. 29, 2006

(65) Prior Publication Data
US 2007/0106157 A1    May 10, 2007

Related U.S. Application Data

(60) Provisional application No. 60/722,491, filed on Sep. 30, 2005.

(51) Int. Cl.
*A61B 8/00* (2006.01)
(52) U.S. Cl. ............ 600/438; 374/43; 374/44; 374/117; 374/118; 374/119; 600/437; 600/439; 601/2; 601/3
(58) Field of Classification Search ............... 374/1, 43, 374/44, 117, 118, 119; 600/437, 438, 439; 601/2, 3
See application file for complete search history.

(56) References Cited

U.S. PATENT DOCUMENTS

| 385,256 A | 6/1888 | Eggers |
| 2,992,553 A | 7/1961 | Joy .................................. 73/644 |
| 4,059,098 A | 11/1977 | Murdock ........................... 128/2 |
| 4,484,569 A | 11/1984 | Driller et al. .................... 128/60 |
| 4,545,386 A | 10/1985 | Hetz et al. ...................... 600/462 |
| 4,601,296 A | 7/1986 | Yerushalmi .................... 607/156 |
| 4,688,578 A | 8/1987 | Takano et al. .................. 128/660 |
| 4,708,836 A | 11/1987 | Gain et al. ..................... 264/40.1 |
| 4,773,865 A | 9/1988 | Baldwin ........................ 434/268 |
| RE33,590 E | 5/1991 | Dory ...................... 128/999.999 |
| 5,039,774 A | 8/1991 | Shikinami et al. .............. 528/60 |
| 5,065,742 A | 11/1991 | Belikan et al. ................... 128/24 |
| 5,080,101 A | 1/1992 | Dory ...................... 128/999.999 |
| 5,080,102 A | 1/1992 | Dory ...................... 128/999.999 |
| 5,088,498 A | 2/1992 | Beach et al. ................... 600/453 |

(Continued)

FOREIGN PATENT DOCUMENTS

DE            04230415      *    3/1994

(Continued)

OTHER PUBLICATIONS

Accord et al., "The Issue of Transmurality in Surgical Ablation for Atrial Fibrillation." *Cardiothoracic Surgery Network*: 3pp, Aug. 8, 2005.*

(Continued)

*Primary Examiner* — Long V Le
*Assistant Examiner* — Ellsworth Weatherby

(57) ABSTRACT

Ultrasound data are collected from a thermal source and a mass of tissue before initiating therapy to measure two parameters of the bio-heat transfer equation (BHTE). The parameters are the thermal diffusivity (K) of the tissue and the magnitude of the thermal source (Q). Once the parameters have been obtained, the BHTE can be calibrated to the specific mass of tissue and the specific thermal source. The calibrated BHTE can be used to generate a temperature dependence curve calibrated to the thermal source and tissue, and spatio-temporal temperature maps, to facilitate pre-therapy planning. During therapy, ultrasound data are collected to determine if Q changes during therapy, and if so, the BHTE is recalibrated using the new Q value, increasing an accuracy of the temperature estimations.

38 Claims, 22 Drawing Sheets

U.S. PATENT DOCUMENTS

| | | | | |
|---|---|---|---|---|
| 5,150,712 A | 9/1992 | Dory | | 128/999.999 |
| 5,170,790 A | 12/1992 | Lacoste et al. | | 600/437 |
| 5,178,148 A | 1/1993 | Lacoste et al. | | 600/439 |
| 5,183,046 A | 2/1993 | Beach et al. | | 600/453 |
| 5,194,291 A | 3/1993 | D'Aoust et al. | | 148/276 |
| 5,215,680 A | 6/1993 | D'Arrigo | | 516/11 |
| 5,219,401 A | 6/1993 | Cathignol et al. | | 128/999.999 |
| 5,230,334 A | 7/1993 | Klopotek | | 128/999.999 |
| 5,289,820 A | 3/1994 | Beach et al. | | 600/443 |
| 5,311,869 A | 5/1994 | Okazaki | | 128/999.999 |
| 5,391,140 A | 2/1995 | Schaetzle et al. | | 601/4 |
| 5,394,877 A | 3/1995 | Orr et al. | | 600/459 |
| 5,471,988 A | 12/1995 | Fujio et al. | | 128/999.999 |
| 5,474,071 A | 12/1995 | Chapelon et al. | | 600/439 |
| 5,492,126 A | 2/1996 | Hennige et al. | | 600/439 |
| 5,507,790 A | 4/1996 | Weiss | | 607/100 |
| 5,520,188 A | 5/1996 | Hennige et al. | | 128/999.999 |
| 5,522,878 A | 6/1996 | Montecalvo et al. | | 607/152 |
| 5,526,815 A | 6/1996 | Granz et al. | | 128/999.999 |
| 5,534,232 A | 7/1996 | Denes et al. | | 422/186.26 |
| 5,536,489 A | 7/1996 | Lohrmann et al. | | 424/9.52 |
| 5,558,092 A | 9/1996 | Unger et al. | | 128/999.999 |
| 5,573,497 A | 11/1996 | Chapelon | | 601/2 |
| 5,609,485 A | 3/1997 | Bergman et al. | | 434/262 |
| 5,638,823 A | 6/1997 | Akay et al. | | 600/528 |
| 5,657,760 A | 8/1997 | Ying et al. | | 128/999.999 |
| 5,666,954 A | 9/1997 | Chapelon et al. | | 600/439 |
| 5,716,374 A | 2/1998 | Francese et al. | | 606/207 |
| 5,720,286 A | 2/1998 | Chapelon et al. | | 600/439 |
| 5,720,287 A | 2/1998 | Chapelon et al. | | 600/439 |
| 5,726,066 A | 3/1998 | Choi | | 438/3 |
| 5,755,228 A | 5/1998 | Wilson et al. | | 128/660.06 |
| 5,762,066 A | 6/1998 | Law et al. | | 128/999.999 |
| 5,769,790 A | 6/1998 | Watkins et al. | | 600/439 |
| 5,807,285 A | 9/1998 | Vaitekunas | | 601/2 |
| 5,810,007 A | 9/1998 | Holupka et al. | | 600/439 |
| 5,817,021 A | 10/1998 | Reichenberger | | 600/439 |
| 5,823,962 A | 10/1998 | Schaetzle et al. | | 600/439 |
| 5,824,277 A | 10/1998 | Campos et al. | | 423/242.1 |
| 5,827,204 A | 10/1998 | Grandia et al. | | 601/2 |
| 5,833,647 A | 11/1998 | Edwards | | 604/22 |
| 5,840,028 A | 11/1998 | Chubachi et al. | | 600/437 |
| 5,846,517 A | 12/1998 | Unger | | 424/9.52 |
| 5,853,752 A | 12/1998 | Unger et al. | | 424/450 |
| 5,873,828 A | 2/1999 | Fujio et al. | | 600/439 |
| 5,879,314 A | 3/1999 | Peterson et al. | | 601/2 |
| 5,882,302 A | 3/1999 | Driscoll, Jr. et al. | | 600/371 |
| 5,895,356 A | 4/1999 | Andrus et al. | | 600/439 |
| 5,897,495 A | 4/1999 | Aida et al. | | 600/411 |
| 5,906,580 A | 5/1999 | Kline-Schoder et al. | | 600/459 |
| 5,919,139 A | 7/1999 | Lin | | 600/443 |
| 5,922,945 A | 7/1999 | Allmaras et al. | | 73/52 |
| 5,931,786 A | 8/1999 | Whitmore, III et al. | | 600/459 |
| 5,935,339 A | 8/1999 | Henderson et al. | | 134/1 |
| 5,951,476 A | 9/1999 | Beach | | 600/437 |
| 5,976,092 A | 11/1999 | Chinn | | 600/459 |
| 5,993,389 A | 11/1999 | Driscoll, Jr. et al. | | 600/371 |
| 5,997,481 A | 12/1999 | Adams et al. | | 600/459 |
| 6,007,499 A | 12/1999 | Martin et al. | | 601/3 |
| 6,036,650 A | 3/2000 | Wu et al. | | 600/462 |
| 6,039,694 A | 3/2000 | Larson et al. | | 600/459 |
| 6,050,943 A | 4/2000 | Slayton et al. | | 600/439 |
| 6,067,371 A | 5/2000 | Gouge et al. | | 382/128 |
| 6,071,239 A | 6/2000 | Cribbs et al. | | 600/439 |
| 6,128,522 A | 10/2000 | Acker et al. | | 600/411 |
| 6,179,831 B1 | 1/2001 | Bliweis | | 606/21 |
| 6,200,539 B1 | 3/2001 | Sherman et al. | | 422/186.04 |
| 6,221,015 B1 | 4/2001 | Yock | | 600/439 |
| 6,267,734 B1 | 7/2001 | Ishibashi et al. | | 601/2 |
| 6,406,759 B1 | 6/2002 | Roth | | 427/562 |
| 6,409,720 B1 | 6/2002 | Hissong et al. | | 606/27 |
| 6,425,867 B1 | 7/2002 | Vaezy | | 600/439 |
| 6,443,894 B1 | 9/2002 | Sumanaweera et al. | | 600/443 |
| 6,488,639 B1 | 12/2002 | Ribault et al. | | 601/2 |
| 6,491,672 B2 | 12/2002 | Slepian et al. | | 604/267 |
| 6,548,047 B1 | 4/2003 | Unger | | 424/9.51 |
| 6,551,576 B1 | 4/2003 | Unger et al. | | 424/9.52 |
| 6,584,360 B2 | 6/2003 | Francischelli et al. | | 607/98 |
| 6,595,934 B1 | 7/2003 | Hissong et al. | | 601/3 |
| 6,599,256 B1 | 7/2003 | Acker et al. | | 601/2 |
| 6,626,855 B1 | 9/2003 | Weng et al. | | 601/3 |
| 6,633,658 B1 | 10/2003 | Dabney et al. | | 382/128 |
| 6,656,136 B1 | 12/2003 | Weng et al. | | 601/2 |
| 6,676,601 B1 | 1/2004 | Lacoste et al. | | 600/439 |
| 6,685,639 B1 | 2/2004 | Wang et al. | | 600/439 |
| 6,706,892 B1 | 3/2004 | Ezrin et al. | | 548/548 |
| 6,709,407 B2 | 3/2004 | Fatemi | | 600/559 |
| 6,716,184 B2 | 4/2004 | Vaezy et al. | | 601/3 |
| 6,719,694 B2 | 4/2004 | Weng et al. | | 600/439 |
| 6,719,699 B2 | 4/2004 | Smith | | 600/459 |
| 6,726,627 B1 | 4/2004 | Lizzi et al. | | 600/439 |
| 6,735,461 B2 | 5/2004 | Vitek et al. | | 600/411 |
| 6,764,488 B1 | 7/2004 | Burbank et al. | | 606/51 |
| 6,846,291 B2 | 1/2005 | Smith et al. | | 600/459 |
| 6,875,176 B2 | 4/2005 | Mourad et al. | | 600/442 |
| 6,875,420 B1 | 4/2005 | Quay | | 424/9.52 |
| 6,905,498 B2 | 6/2005 | Hooven | | 606/50 |
| 6,932,771 B2 | 8/2005 | Whitmore et al. | | 607/105 |
| 6,955,648 B2 | 10/2005 | Mozayeni et al. | | 600/454 |
| 7,022,077 B2 | 4/2006 | Mourad et al. | | 600/442 |
| 7,052,463 B2 | 5/2006 | Peszynski et al. | | 600/459 |
| 7,149,564 B2 | 12/2006 | Vining et al. | | 600/425 |
| 7,260,250 B2 | 8/2007 | Summers et al. | | 382/128 |
| 7,285,093 B2 | 10/2007 | Anisimov et al. | | 600/437 |
| 7,445,599 B2 | 11/2008 | Kelly et al. | | 600/437 |
| 7,534,209 B2 | 5/2009 | Abend et al. | | 600/437 |
| 7,628,764 B2 | 12/2009 | Duarte et al. | | 601/2 |
| 7,684,865 B2 | 3/2010 | Aldrich et al. | | 607/40 |
| 7,697,972 B2 | 4/2010 | Verard et al. | | 600/424 |
| 2002/0193831 A1 | 12/2002 | Smith, III | | 607/5 |
| 2003/0018255 A1 | 1/2003 | Martin et al. | | 600/3 |
| 2003/0069569 A1* | 4/2003 | Burdette et al. | | 600/427 |
| 2003/0195420 A1* | 10/2003 | Mendlein et al. | | 600/459 |
| 2003/0208101 A1* | 11/2003 | Cecchi | | 600/466 |
| 2004/0002654 A1 | 1/2004 | Davidson et al. | | 600/454 |
| 2004/0030268 A1 | 2/2004 | Weng et al. | | 601/2 |
| 2004/0078034 A1* | 4/2004 | Acker et al. | | 606/27 |
| 2004/0097840 A1* | 5/2004 | Holmer | | 601/2 |
| 2004/0122493 A1* | 6/2004 | Ishibashi et al. | | 600/437 |
| 2004/0153126 A1* | 8/2004 | Okai | | 606/27 |
| 2004/0234453 A1* | 11/2004 | Smith | | 424/9.5 |
| 2004/0254620 A1* | 12/2004 | Lacoste et al. | | 607/96 |
| 2005/0065436 A1* | 3/2005 | Ho et al. | | 600/431 |
| 2005/0182319 A1* | 8/2005 | Glossop | | 600/424 |
| 2005/0240102 A1 | 10/2005 | Rachlin et al. | | 600/437 |
| 2006/0184069 A1 | 8/2006 | Vaitekunas | | 601/2 |
| 2008/0045864 A1* | 2/2008 | Candy et al. | | 601/2 |
| 2008/0045865 A1* | 2/2008 | Kislev | | 601/3 |
| 2008/0200815 A1* | 8/2008 | Van Der Steen et al. | | 600/467 |
| 2008/0319375 A1* | 12/2008 | Hardy | | 604/22 |

FOREIGN PATENT DOCUMENTS

| | | | |
|---|---|---|---|
| EP | 0 420 758 | * | 4/1991 |
| EP | 1 265 223 | * | 12/2002 |
| JP | H09-103434 | | 4/1997 |
| JP | 2002-500939 | | 1/2002 |
| JP | 2004-113789 | | 4/2004 |
| WO | WO 97/31364 | * | 8/1997 |
| WO | WO 00/72919 | * | 12/2000 |
| WO | WO 02/069805 | * | 9/2002 |

OTHER PUBLICATIONS

Amenta et al., "A New Voronoi-Based Surface Reconstruction Algorithm." *Computer Graphics*: 7pp, 1998.*

American Red Cross., "Blood 101." 4pp., Dec. 11, 2007.*

Anand et al., "Using the ATL 1000 to Collect Domodulated RF Data for Monitoring HIFU Lesion Formation." *Presented at SPIE Medical Imaging 2003*. 11pp, 2003.*

Aurenhammer, F. "Voronoi diagrams—A Survey of a Fundamental Geometric Data Structure." *ACM Computing Surveys*, vol. 23, No. 3: 345-405, Sep. 1991.

Bachmann et al., "Targeting Mucosal Addressin Cellular Adhesion Molecule (MAdCAM)-1 to Noninvasively Image Experimental Crohn's Disease." *Gastroenterology*; vol. 130: 8-16, 2006.

Bauer et al., "Ultrasound Imaging with SonoVue: Low Mechanical Index Real-Time Imaging." *Acad. Radiol.*; vol. 9, Suppl. 2: S282-S284, 2002.

Beard et al., "An Annular Focus Ultrasonic Lens for Local Hyperthermia Treatment of Small Tumors." *Ultrasound in Medicine & Biology*; vol. 8, No. 2: 177-184, 1982.

Bokarewa et al., "Tissue factor as a proinflammatory agent." *Arthritis Research*, vol. 4: 190-195, Jan. 10, 2002.

Bots et al., "Intima Media Thickness as a Surrogate Marker for Generalised Atherosclerosis." *Cardiovascular Drugs and Therapy*, ProQuest Medical Library; vol. 16, No. 4: 341-351, Jul. 2002.

Brayman et al., "Erosion of Artificial Endothelia In Vitro by Pulsed Ultrasound: Acoustic Pressure, Frequency, Membrane Orientation and Microbubble Contrast Agent Dependence." *Ultrasound in Medicine & Biology*; vol. 25, No. 8: 1305-1320, 1999.

Buller et al., "Accurate Three-dimensional Wall Thickness Measurement From Multi-Slice Short-Axis MR Imaging." *Computers in Cardiology*, 245-248, 1995.

Chao et al., "Aspheric lens design." *Ultrasonics Symposium*, 2000 IEEE, vol. 2: Abstract Only, Oct. 2000.

Cheliue et al., "Fabrication of Medical Models From Scan Data via Rapid Prototyping Techniques." 9 pp., Feb. 7, 2007.

Chen et al., "A comparison of the fragmentation thresholds and inertial cavitation doses of different ultrasound contrast agents." *Journal of the Acoustical Society of America*, vol. 113, No. 1: 643-665, Jan. 2003.

Chen et al., "Inertial Cavitation Dose and Hemolysis Produced In Vitro With or Without Optison." *Ultrasound in Medicine & Biology*, vol. 29, No. 5: 725-737, 2003.

Chong et al., "Tissue Factor and Thrombin Mediate Myocardial Ischemia-Reperfusion Injury." *The Society of Thoracic Surgeons*, vol. 75: S649-655, 2003.

Dayton et al., "The magnitude of radiation force on ultrasound contrast agents." *Journal of the Acoustical Society of America*, vol. 112, No. 5, Part 1: 2183-2192, Nov. 2002.

Dempsey et al., "Thickness of Carotid Artery Atherosclerotic Plaque and Ischemic Risk." *Neurosurgery*, vol. 27, No. 3: 343-348, 1990.

Ebbini et al., "Image-guided noninvasive surgery with ultrasound phased arrays." *SPIE*, vol. 3249: 230-239, Apr. 2, 1998.

Edelsbrunner, Herbert. "Geometry and Topology for Mesh Generation." *Cambridge University Press*: 68pp, 2001.

Everbach et al., "Cavitational Mechanisms in Ultrasound-Accelerated Thrombolysis at 1 MHz." *Ultrasound in Medicine & Biology*, vol. 26, No. 7: 1153-1160, 2000.

Ewert et al., "Anti-myeloperoxidase antibodies stimulate neutrophils to damage human endothelial cells." *Kidney International*, vol. 41: 375-383, 1992.

Ganapathy et al., "A New General Triangulation Method for Planar Contours." *Computer Graphics* vol. 16, No. 3:69-75, 1982.

Gray, Henry. "The Skull." *Anatomy of the Human Body*: 7pp., 1918.

Guzman et al., "Ultrasound—Mediated Disruption of Cell Membranes. I. Quantification of Molecular uptake and Cell Viability. / II. Heterogeneous effects on cells." *Journal of the Acoustical Society of America*, vol. 110, No. 1: 588-606, Jul. 2001.

Hadimioglu et al., "High-Efficiency Fresnel Acoustic Lenses." *Ultrasonics Symposium 1993 IEEE*: 579-582, 1993.

Han et al., "A Fast Minimal Path Active Contour Model." IEEE Transactions on Image Processing, vol. 10, No. 6: 865-873, Jun. 2001.

Hatangadi, Ram. "A Novel Dual Axis Multiplanar Transesophageal Ultrasound Probe for Three-Dimensional Echocardiograph."_*University of Washington, Department of Sciences and Engineering*, vol. 55-11B: Abstract 1pg, 1994.

Holt et al., "Bubbles and Hifu: the Good, the Bad and the Ugly." *Boston University, Department of Aerospace and Mechanical Engineering*: 120-131, 2002.

Hubka et al., "Three-dimensional echocardiographic measurement of left ventricular wall thickness: In vitro and in vivo validation." *Journal of the American Society of Echocardiography*, vol. 15, No. 2: 129-135, 2002.

Hwang et al., "Vascular Effects Induced by Combined 1-MHz Ultrasound and Microbubble Contrast Agent Treatments In Vivo." *Ultrasound in Medicine & Biology*, vol. 31, No. 4: 553-564, 2005.

Hynynen et al., "Potential Adverse Effects of High-Intensity Focused Ultrasound Exposure on Blood Vessels In Vivo." *Ultrasound in Medicine & Biology*, vol. 22, No. 2: 193-201, 1996.

Iannuzzi et al., "Ultrasonographic Correlates of Carotid Atherosclerosis in Transient Ischemic Attack and Stroke" *Stroke*, ProQuest Medical Library, vol. 26, No. 4: 614-619, 1995.

Idell et al., "Fibrin Turnover in Lung Inflammation and Neoplasia." *American Journal of Respiratory and Critical Care Medicine*, vol. 163: 578-584, 2001.

Indman, Paul. "Alternatives in Gynecology." *Hysteroscopy*, OBGYN.net, 2000. http://www.gynalternatives.com/hsc.html.

Kaczkowski et al., "Development of a High Intensity Focused Ultrasound System for Image-Guided Ultrasonic Surgery." *Ultrasound for Surgery*, 2001. <http://cimu.apl.washington.edu/hifusurgerysystem.html>.

Kang et al., "Analysis of the Measurement Precision of Arterial Lumen and Wall Areas Using High-Resolution MRI." *Magnetic Resonance in Medicine*, vol. 44: 968-972, 2000.

Klibanov et al., "Detection of Individual Microbubbles of an Ultrasound contrast Agent: Fundamental and Pulse Inversion Imaging." *Academy of Radiology*, vol. 9, Suppl. 2: S279-S281, 2002.

Kudo et al., "Study on Mechanism of Cell Damage Caused by Microbubbles Exposed to Ultrasound." *Ultrasound in Medicine & Biology*, vol. 29, Supplement: 4pp, 2003.

Lalonde et al., "Field conjugate acoustic lenses for ultrasound hyperthermia." *Ultrasonics, Ferroelectrics and Frequency Control, IEEE Transactions*, vol. 40, Issue 5: Abstract 1pg., Sep. 1993.

Meyers, D. "Multiresolution tiling." *Computer Graphics*, No. 5: 325-340, 1994.

Miller et al., "A Review of In Vitro Bioeffects of Inertial Ultrasonic Cavitation From a Mechanistic Perspective." *Ultrasound in Medicine & Biology*, vol. 22, No. 9: 1131-1154, 1996.

Miller et al., "Diagnostic ultrasound activation of contrast agent gas bodies induces capillary rupture in mice." *PNAS*, vol. 97, No. 18: 10179-10184, 2000.

Ng et al., "Therapeutic Ultrasound: Its Application in Drug Delivery." *Medicinal Research Reviews*, vol. 22, No. 2: 204-233, 2002.

O'Leary et al., "Carotid-artery Intima and Media Thickness as a Risk Factor for Myocardial Infarction and Stroke in Older Adults." Cardiovascular Health Study Collaborative Research Group. *New England Journal of Medicine*, vol. 340, No. 1: 14-22, Jan. 7, 1999.

Ostensen et al., "Characterization and Use of Ultrasound Contrast Agents." *Academy of Radiology*, vol. 9, Suppl. 2: S276-S278, 2002.

Owaki et al., "The Ultrasonic Coagulating and Cutting System Injuries Nerve Function." *Endoscopy*, vol. 34, No. 7: 575-579, 2002.

Pignoli et al., "Intimal plus medial thickness of the arterial wall: a direct measurement with ultrasound imaging." *Circulation*, vol. 74, No. 6:1399-1406, Dec. 1986.

Poliachik et al., "Activation, Aggregation and Adhesion of Platelets Exposed to High-Intensity Focused Ultrasound." *Ultrasound in Medicine & Biology*, vol. 27, No. 11: 1567-1576, 2001.

Poliachik et al., "Effect of High—Intensity Focused Ultrasound on Whole Blood With or Without Microbubble Contrast Agent." *Ultrasound in Medicine & Biology*, vol. 25, No. 6: 991-998, 1999.

Porter et al., "Ultrasound, Microbubbles and Thrombolysis." *Progress in Cardiovascular Diseases*, vol. 44, No. 2: 101-110, Oct. 2001.

Rivens et al., "Vascular Occlusion Using Focused Ultrasound Surgery for Use in Fetal Medicine." *European Journal of Ultrasound*, vol. 9: 89-97, 1999.

Rosen et al., "Vascular Occlusive Diseases." 37pp., revised 2002.

Rosenschein et al., "Shock-Wave Thrombus Ablation, A New Method for Noninvasive Mechanical Thrombolysis." *The American Journal of Cardiology*, vol. 70, Issue 15: Abstract, Nov. 15, 1992.

Rosenschein et al., "Ultrasound Imaging-Guided Noninvasive Ultrasound Thrombolysis-Preclinical Results." *Circulation*, vol. 102: 238-245, 2000. <http://www.circulationaha.com.org>.

Schulte-Altedorneburg et al., "Accuracy of in Vivo Carotid B-Mode Ultrasound Compared with Pathological Analysis: Intima-Media Thickening, Lumen Diameter, and Cross-Sectional Area." *Stroke*, vol. 32, No. 7: 1520-1524, 2001.

Tachibana et al., "Albumin Microbubble Echo-Contrast Material as an Enhancer for Ultrasound Accelerated Thrombolysis." *Circulation*, vol. 92: 1148-1150, 1995.

Tachibana et al., "The Use of Ultrasound for Drug Delivery." *Echocardiography*, vol. 18, No. 4: 323-328, May 2001.

Tardy et al., "In Vivo Ultrasound Imaging of Thrombi Using a Target-specific Contrast Agent." *Academy of Radiology*, vol. 9, Suppl. 2: S294-S296, 2002.

Vaezy et al., "Acoustic surgery." *Physics World*: 35-39, Aug. 2001.

Vaezy et al., "Hemostasis and Tumor Treatment using High Intensity Focused Ultrasound: Experimental Investigations and Device Development." *First International Workshop on the Application of HIFU in Medicine*: 46-49, 2001.

Vaezy et al., "Hemostasis using high intensity focused ultrasound." *European Journal of Ultrasound*, vol. 9: 79-87, 1999.

Vaezy et al., "Intra-operative acoustic hemostasis of liver: production of a homogenate for effective treatment." *Ultrasonics*, vol. 43: 265-269, 2005.

Von Land et al., "Development of an Improved Centerline Wall Motion Model." *IEEE*: 687-690, 1991.

Watkin et al., "Multi-Modal Contrast Agents: A First Step." *Academy of Radiology*, vol. 9, Suppl. 2: S285-S287, 2002.

Wickline et al., "Blood Contrast Enhancement with a Novel, Non-Gaseous Nanoparticle Contrast Agent." *Academy of Radiology*, vol. 9, Suppl. 2: S290-S293, 2002.

Williamson et al., "Color Doppler Ultrasound Imaging of the Eye and Orbit." *Survey of Ophthamology*, vol. 40, No. 4: 255-267, 1996.

Yu et al., "A microbubble agent improves the therapeutic efficiency of high intensity focused ultrasound: a rabbit kidney study." *Urological Research*, PubMed: Abstract, 2004.

n. a., "Cavitation." Ultrasound TIP—U.S. Database: Dec. 12, 2007.

n. a., "Mechanical Bioeffects in the Presence of Gas-Carrier Ultrasound Contrast Agents." *Journal of Ultrasound & Medicine*, vol. 19: 120-142, 2000.

n. a., "Breast Cancer—Insightec: focused ultrasound for non invasive treatment." FAQ, 2000. <http://www.exablate2000.com/physicians_faq.html>.

Anand, Ajay and Kaczkowski, Peter J. "Monitoring formation of high intensity focused ultrasound (HIFU) induced lesions using backscattered ultrasound." Acoustical Society of America. (Mar. 10, 2004).

Aaslid et al., "Noninvasive transcranial Doppler ultrasound recording of flow velocity in basal cerebral arteries." *Journal of Neurosurgery*, vol. 57: 769-774, 1982.

Campbell et al. "Pulsatile Echo-encephalography." *Acta Neurologica Scandinavica Supplementum 45*, vol. 46: 1-57, 1970.

Dahl et al., "Simultaneous Assessment of Vasoreactivity Using Transcranial Doppler Ultrasound and Cerebral Blood Flow in Healthy Subjects." *Journal of Cerebral Blood Flow and Metabolism*, vol. 14, No. 6: 974-981, 1994.

Gao et al., "Imaging of the Elastic Properties of Tissue—A Review." *Ultrasound in Medicine & Biology*, vol. 22, No. 8: 959-977, 1996.

Klingelhöfer et al., "Chapter 4: Functional Ultrasonographic Imaging" in Babikian VL, Wechsler LR, eds. *Transcranial Doppler Ultrasonography*. Woburn, MA: Butterworth-Heinemann, 49-66, 1999.

Markwalder et al., "Dependency of Blood Flow Velocity in the Middle Cerebral Artery on End-Tidal Carbon Dioxide Partial Pressure—A Transcranial Ultrasound Doppler Study." *Journal of Cerebral Blood Flow and Metabolism*, vol. 4, No. 3: 368-372, 1984.

\* cited by examiner

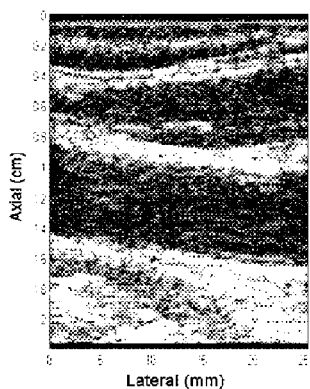 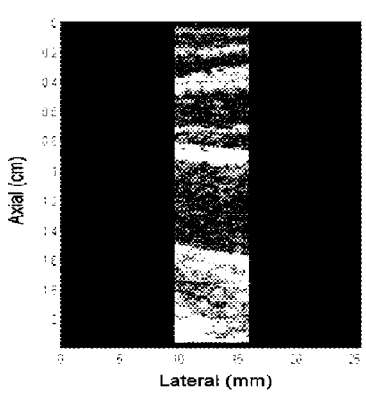 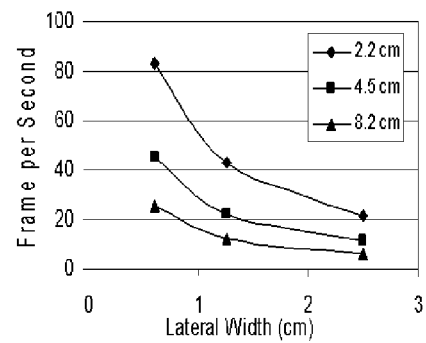
*FIG. 7A*   *FIG. 7B*   *FIG. 7C*
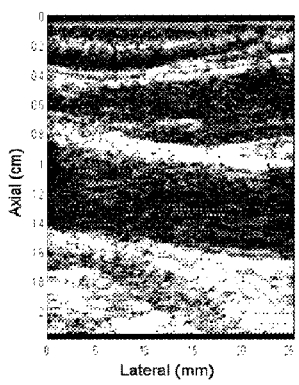 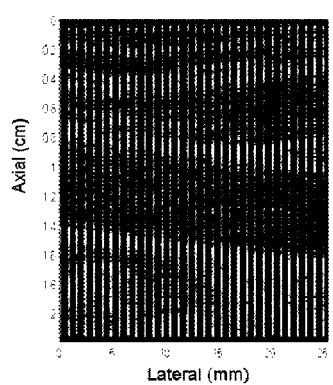 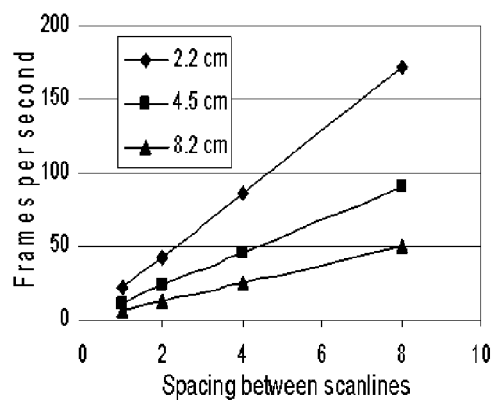
*FIG. 8A*   *FIG. 8B*   *FIG. 8C*
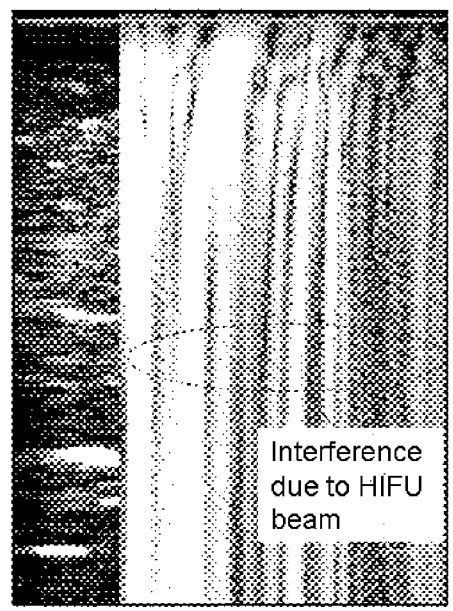
*FIG. 9*

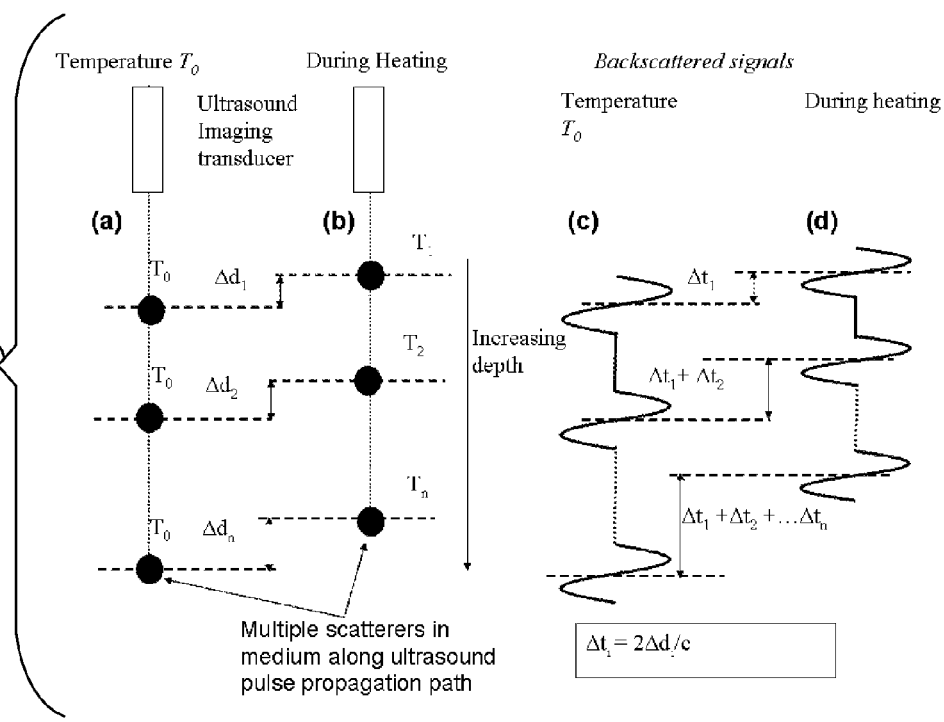
FIGS. 14A-D
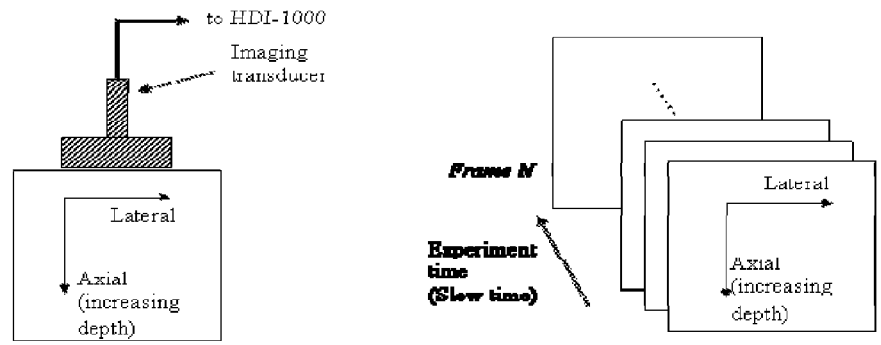
FIGS. 16A-16B
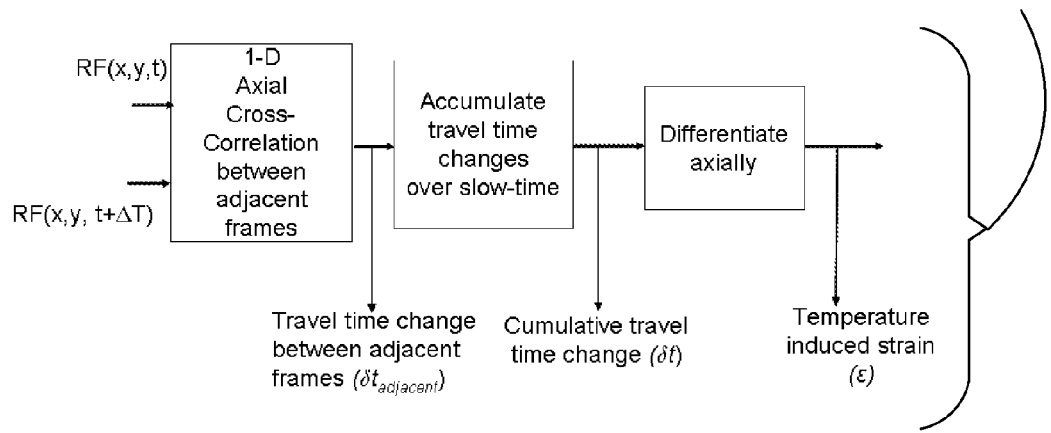
FIG. 16C

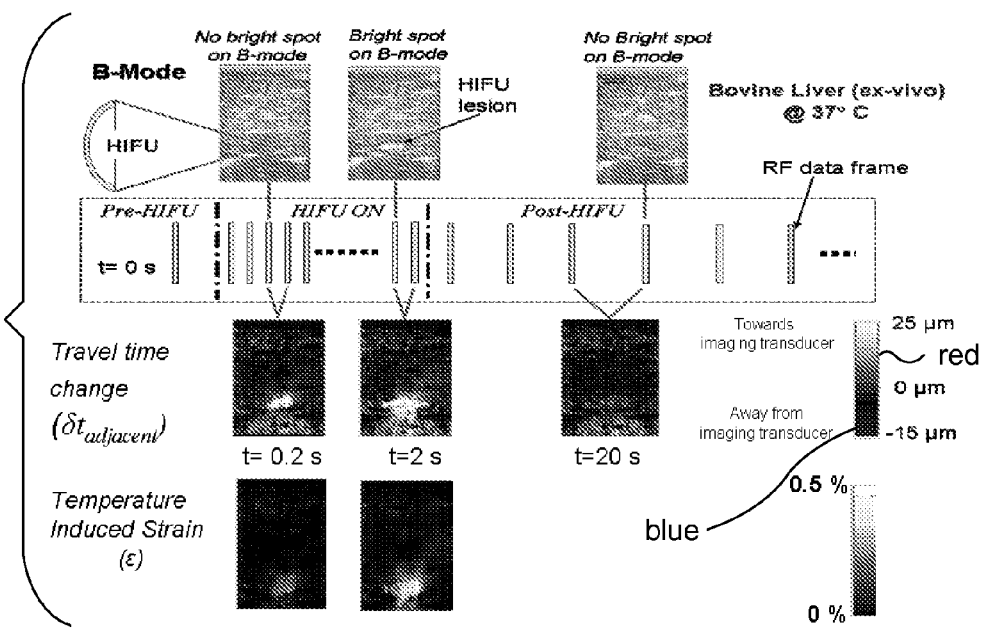
FIG. 17
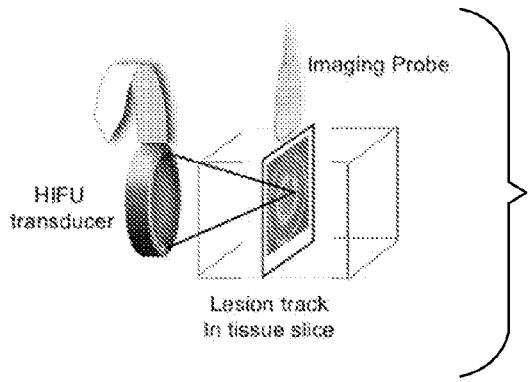
FIG. 18
FIGS. 19A-19B
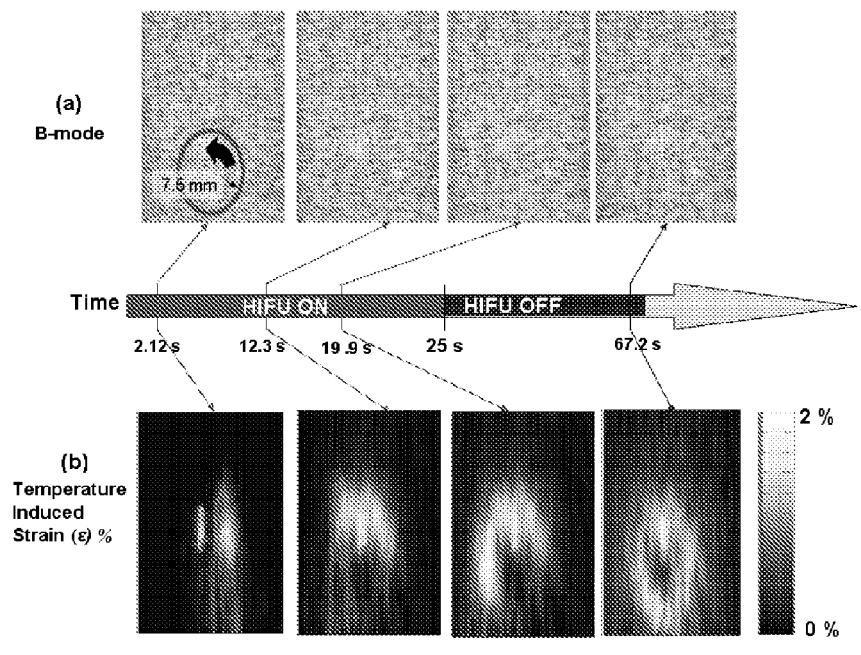

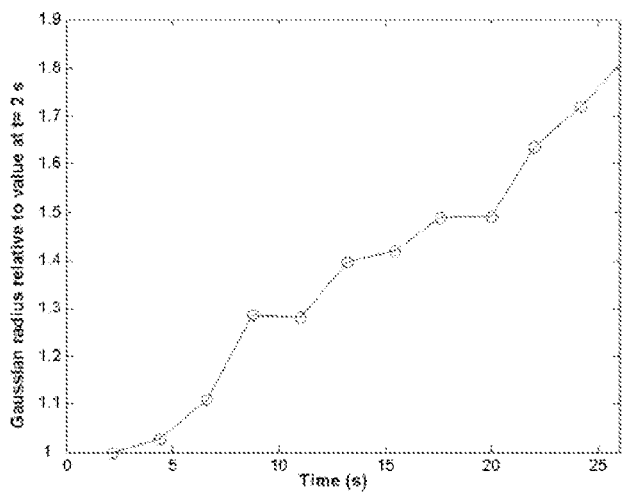
*FIG. 20*
*FIG. 21*
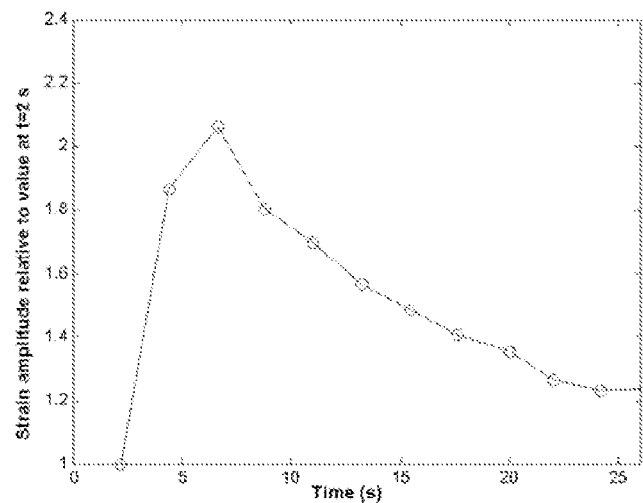
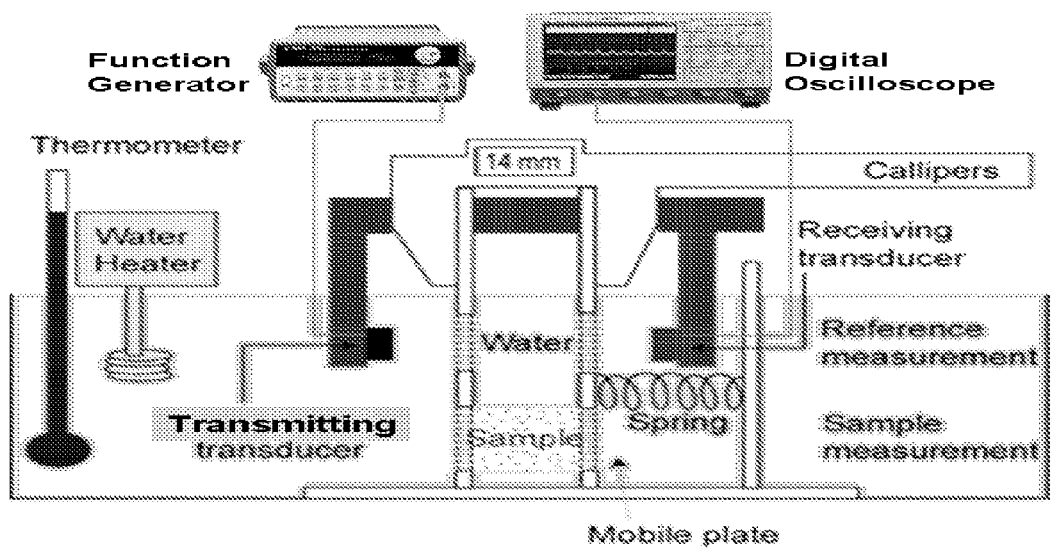
*FIG. 22*

1. Fix value for thermal diffusivity (K) from "probe" experiment 1
2. Assume initial "guess" heat source $Q_{curr}' = Q_0$; Initial temperature distribution $T_0 = 37$;
3. Time instant of hyperechoic spot = $t_{100}$ measured from "probe" experiment 2
4. Input expected temperature profile at $t_{100}$ in focus=$T_{expected}$ (100°C at focal peak)

NON-INVASIVE TEMPERATURE ESTIMATION TECHNIQUE FOR HIFU THERAPY MONITORING USING BACKSCATTERED ULTRASOUND

RELATED APPLICATIONS

This application is based on a prior copending provisional application Ser. No. 60/722,491, filed on Sep. 30, 2005, the benefit of the filing date of which is hereby claimed under 35 U.S.C. §119(e).

GOVERNMENT RIGHTS

This invention was made with U.S. Government support under grant Nos. N00014-01-G-0460 and N00014-99-1-0982 awarded by the Office of Naval Research (ONR) and by grant No. DAMD17-02-2-0014 awarded by the Department of the Army (U.S. Army Medical Research Acquisition Activity). The U.S. Government has certain rights in the invention.

BACKGROUND

There exist several medical therapies that involve inducing temperature changes in parts of the body. To facilitate the monitoring of such therapies, it would be desirable to provide apparatus and techniques for non-invasively measuring the temperature of an internal treatment site.

One such therapeutic technique involves the use of high intensity ultrasound fields, which can be focused on deep seated regions within the human body. If sufficient acoustic energy is concentrated within the focal volume, the temperature in that region can be increased to a level sufficient to induce cellular necrosis. This technique is commonly referred to as High Intensity Focused Ultrasound (HIFU) or Focused Ultrasound Surgery (FUS). The focusing of ultrasound can result in high acoustic intensities (measured as power density in W/cm$^2$) at the focus. An intensity gain of 100 to 1000 times can be achieved in the cross-sectional area of the beam at the focus, resulting in intensities upward of 1000 W/cm$^2$, orders of magnitude greater than that of diagnostic ultrasound systems. The technique has potential applications in any medical field that may benefit from the selective destruction of tissue volumes. Clinical interest has concentrated on treating soft-tissue cancers, de-bulking enlarged prostates (benign prostatic hyperplasia), and acoustic homeostasis. HIFU provides the ability to ablate localized tissue volumes without damaging intervening and surrounding tissue, thus eliminating the need for incisions—a feature that distinguishes it from other widely used ablative therapies, such as Radio Frequency (RF) ablation.

HIFU therapy is significantly different than conventional hyperthermia treatment, in which the temperature is raised a few degrees above body temperature and maintained for a relatively lengthy time, typically on the order of minutes. In HIFU therapy, the temperature typically rises by more than 40-50° C. in a few seconds, with increases up to 70° C. in one second having been reported. One consequence of the rapid heating to cytotoxic temperatures is that there is a very narrow boundary between live cells and dead cells at the edges of the focal point volume. The volume of dead cells is referred to as a lesion, and this method of selectively inducing cellular necrosis is commonly referred to as thermal ablation.

Some form of medical imaging can be employed to facilitate HIFU therapy. Because HIFU therapy can be carried out non-invasively, a non-invasive imaging technology will normally be employed. Medical imaging can facilitate HIFU therapy by enabling the exact location of abnormal tissue to be identified and targeted, by providing verification that the HIFU focal point properly corresponds to the abnormal tissue, by facilitating monitoring during HIFU treatment to ensure optimal therapeutic dose control, and by enabling post-therapy imaging of the treatment site to assess treatment efficacy. Ultrasound imaging for guiding HIFU therapy offers the following advantages: ultrasound imaging can be performed in real-time, ultrasound imaging has minimal side effects, ultrasound imaging equipment is ubiquitous and relatively inexpensive, ultrasound imaging and therapeutic ultrasound can be easily integrated into a single assembly, and acoustic distortions arising from sound wave and tissue interactions will generally have similar effects on both imaging ultrasound and HIFU.

Temperature measurements during HIFU therapy are useful for several reasons. First, a spatio-temporal temperature map overlaid over a B-mode ultrasound image of the treatment site will enable a clinician to prevent the temperatures of non-target tissue (such as tissue beyond the bounds of a tumor) from reaching necrotic levels. Further, temperature measurements can be used to calculate a thermal dose. It has been suggested and experimentally verified that, once a tissue type dependent thermal dose has been achieved for a given volume inside the tumor, irreversible damage will have been caused in this region. Based on the times for which temperatures are held, an equivalent time at one reference temperature (usually taken to be 43° C.) is computed, and this time estimate is referred to as the thermal dose. The mathematical expressions for thermal dose are as follows:

$$TD_{43} = (x, t_{end} - t_0) = \sum_{t=t_o}^{t_{end}} 2^{T(t,x)-43} \Delta t, \; T >= 43 \qquad (1)$$

$$TD_{43}(x, t_{end} - t_0) = \sum_{t=t_o}^{t_{end}} 0.5^{T(t,x)-43} \Delta t, \; T < 43$$

where T is the temperature at time t, $\Delta t$ represents the time interval between consecutive temperature measurements, $TD_{43}$ is the thermal dose referenced to 43° C., x is the spatial location in tissue where the thermal dose is computed, and $t_o$ and $t_{end}$ represent the start time and end time of treatment, respectively. This expression has typically been used in hyperthermia treatments, in which the heating profile is relatively long and stays near 43.0° C., but also has been suggested for use in HIFU. From Eq. (1), it can be seen that estimating the temporal and spatial profile of the temperature rise during treatment is important for computing the thermal dose delivered to the patient.

Thus, it would be desirable to provide techniques and apparatus enabling ultrasound imaging and ultrasound data-based temperature estimates to be performed during HIFU therapy. Indeed, several suggested techniques have been investigated. In particular, the relationship between the speed of sound in tissue and temperature (i.e., acoustic attenuation) has been studied, in order to enable temperature monitoring to be achieved. Due to the nature of ultrasound imaging, it is relatively straightforward to collect time-of-flight data for ultrasound waves propagating between an imaging transducer and the treatment site. Changes in temperature at the treatment site will affect the speed at which reflected ultrasound waves propagate between the treatment site and the imaging transducer (acting as a receiver), enabling an estimation of temperature at the treatment site to be made.

Unfortunately, temperature estimates generated using the above-noted technique are prone to significant errors, for several reasons. Because the acoustic attenuation of a given mass of tissue is difficult to measure non-invasively, a generic acoustic attenuation value for biological tissue is generally employed to generate temperature estimates based on backscattered ultrasound data. However, the acoustic attenuation of biological tissue is not a constant value, and different types of tissue exhibit different acoustic attenuation (i.e., the speed of sound in fatty tissue is different than the speed of sound in muscle tissue, even at the same temperature). Thus, the use of a generic value for acoustic attenuation will introduce errors into the temperature estimates, and the use of numerical model-based approaches to derive temperature values assuming a priori knowledge of attenuation coefficient are therefore ineffective. It would therefore be desirable to provide a more accurate method and apparatus for obtaining profiles of the spatio-temporal temperature distribution of tissue during thermal therapy.

SUMMARY

The concepts disclosed herein enable ultrasound based non-invasive quantitative temperature estimations to be achieved over the therapeutic temperature range of interest for monitoring thermal-based therapies (such as cryogenic therapy or HIFU), using acoustic travel time changes measured from backscattered ultrasound. Specifically, the model-based techniques described herein are based on combining spatio-temporal constraints imposed by an underlying physical model for heat diffusion, and the bio-heat transfer equation (BHTE), with non-invasively acquired ultrasound backscatter data. This approach addresses the lack of sensitivity of earlier ultrasound-based temperature estimation methods that were based only on acoustic attenuation.

The disclosure provided herein is thus directed to non-invasive temperature monitoring using ultrasound over a wide range of temperatures (from at least room temperature up to the boiling point of water). Furthermore, another aspect of the concepts disclosed herein is a method for using ultrasound to non-invasively measure heat diffusivity of a region of interest (i.e., of a tissue mass), and the magnitude of a heat source in a region of interest. Still another aspect of the concepts disclosed herein is the use of the BHTE to constrain temperature fields estimated using ultrasound. It should be noted that the model-constrained inversion of ultrasound data can be used for applications beyond temperature measurement, such as flow measurement and tissue displacement/strain measurements (elastography), as well as to provide detailed time and temperature maps useful for pre-therapy planning.

In general, two different calibration experiments (one calibration experiment for each of two parameters defined in the BHTE) are performed on the tissue to be thermally treated. One parameter is Q', which relates to the magnitude of the thermal source employed during therapy, as well as tissue properties affecting propagation of thermal energy through the tissue. In one exemplary embodiment, the thermal source is a HIFU therapy probe (i.e., a HIFU transducer or transducers configured to provide HIFU therapy). It should be recognized that other thermal sources, such as a hot wire, radio-frequency ablation, or microwaves, can also be utilized to provide the thermal therapy. It should also be recognized that the thermal source is simply responsible for changing a temperature of tissue, regardless of whether the temperature increases or decreases. Thus, for cryogenic therapy, the thermal source will be used to lower the temperature of a mass of tissue.

The second parameter is K, the thermal diffusivity of the tissue being treated. Signal processing of RF backscattered ultrasound data is used to non-invasively estimate these parameters in situ. Essentially, the pre-calibration exposures employ the same thermal source that will be used to provide therapy, and apply to the same tissue to which therapy will later be provided, which minimizes any variation due to tissue irregularities and differences between thermal sources.

Once the calibration experiments are completed, the data collected in the calibration experiments and the thermal model (i.e., the BHTE) are used to define a temperature dependence curve (i.e., a speed of sound in tissue versus temperature relationship) unique to the tissue being treated and to the thermal source that will be used to provide the thermal therapy. At this point, detailed time and temperature maps can be generated before therapy is initiated, to facilitate pre-therapy planning. During the thermal therapy, backscatter data are collected, and Q' is redefined, based on the collected data. Note that Q' measured during therapy is likely to be different than Q' measured during the calibration experiment, because of attenuation changes to the ultrasound beam caused by variations in tissue absorption in the beam path. Because the previously generated temperature dependence curve was generated based on the Q' value measured in the calibration experiments, any changes to Q' during therapy will affect the temperature dependence curve. Thus, as Q' changes during therapy, new temperature dependence curves are generated to increase the accuracy of the temperature estimations during therapy. The real-time temperature measurements (based on the updated temperature dependence curve) can be compared to the time and temperature maps generated for pre-therapy planning, such that therapy time can be increased or decreased based on real-time data. For example, if the real-time data indicate that the pre-therapy time and temperature maps overestimated the real-time temperature measurements, the therapy time can be increased. Conversely, if the real-time data indicate that the pre-therapy time and temperature maps underestimated the real-time temperature measurements, the therapy time can be decreased. The real-time temperature measurements provide greater control over the thermal therapy, maximizing the therapeutic dose delivered to the target tissue, while minimizing undesired thermal effects on non-target tissue.

To estimate K, the thermal source is employed to induce a relatively modest change in temperature of the target tissue. A temperature change of about 5° C. to about 15° C. is generally sufficient. As the tissue returns to the ambient temperature (i.e., to the temperature before being changed by the thermal source), ultrasound data are collected for the target tissue. RF waveforms are processed to estimate a spatial width of the temperature distribution (the Gaussian radius) as a function of time, using measures of the ultrasound strain for each RF A-line. To achieve enhanced accuracy, a unique strain estimation method is used to detect very small strains over very small regions, using a model for waveform compounding that uses a Gaussian peak function to fit the strain due to the dissipation of heat resulting from the HIFU beam pattern. In this temperature regime, the ultrasonic strain is assumed to be linear with temperature, but the absolute temperature need not be known. The rate of change of the Gaussian radius leads directly to an estimate for K. Independent measures of K determined using invasive transient hot wire techniques in the same tissue have validated the accuracy of this technique for estimating K.

In one exemplary embodiment, where the thermal source is a HIFU transducer, to estimate K, a brief low intensity HIFU exposure is employed to raise tissue temperature at the focal point less than about 15° C. in a few seconds. During cool down of the treated tissue, the RF waveforms are processed as described above. Significantly, no damage will occur to the target tissue in this procedure, since the temperature rise and duration are not sufficient to cause such damage.

To estimate Q', the time required for the thermal source to change the temperature of target tissue to a predetermined temperature value is measured. The measured time, the thermal model (e.g., the BHTE), and the previously determined value for K are used to determine Q'. Q' can thus be determined non-invasively. If it is acceptable to determine Q' invasively, a thermocouple or other temperature sensor can simply be introduced into the target tissue, and the time required to reach a specific temperature is measured. To determine Q' non-invasively presents a greater challenge. The predetermined temperature is selected such that some physical change in the target tissue can be detected non-invasively. For example, the boiling point of water can be selected as the predetermined temperature, because the onset of boiling in tissue can be detected non-invasively. If an imaging modality can detect the onset of freezing (i.e., the generation of ice crystals) non-invasively, then the freezing point of water in tissue can be used as the predetermined temperature.

In one exemplary embodiment, the time is measured for a thermal source, such as a HIFU transducer, to bring the focal zone to the boiling point. The onset of boiling can be detected in several different ways. A first exemplary technique to detect the onset of boiling is to use an audio range hydrophone (or microphone, or some other acoustic sensor) to detect the onset of popping sounds associated with boiling in the tissue. A second exemplary technique to detect the onset of boiling is to use B-mode ultrasound imaging to detect the sudden appearance of a bright echogenic spot at the HIFU focus. The time required to bring the sample to boiling is used to estimate Q' by iteration of the numerical BHTE (using the value for K that was previously determined). This technique to estimate Q' has been verified by comparing non-invasively estimated Q' values generated as indicated above, with Q' values obtained using invasively disposed thermocouples; the results compare favorably. This non-invasive technique to estimate Q' also compares favorably with linear acoustic calculations using independently measured HIFU and tissue medium parameters.

Although such techniques were developed as an integral component of estimating temperature during HIFU therapy, such techniques can be independently employed in therapy planning and dosimetry applications, where information about local tissue thermal parameters is required to accurately predict the applied thermal dose and to plan the therapy protocol. Such techniques can also be utilized as a general tissue characterization technique and are applicable in other thermally ablative treatment modalities, such as RF ablation, and microwave therapy, which also relies on rapid heating for tissue necrosis. The techniques can also be applied to cryo-surgery, in which tissue is destroyed by freezing. Finally, such techniques may be useful in other methods that modify tissue properties, for example, using alcohol injection.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

Figure 1A:
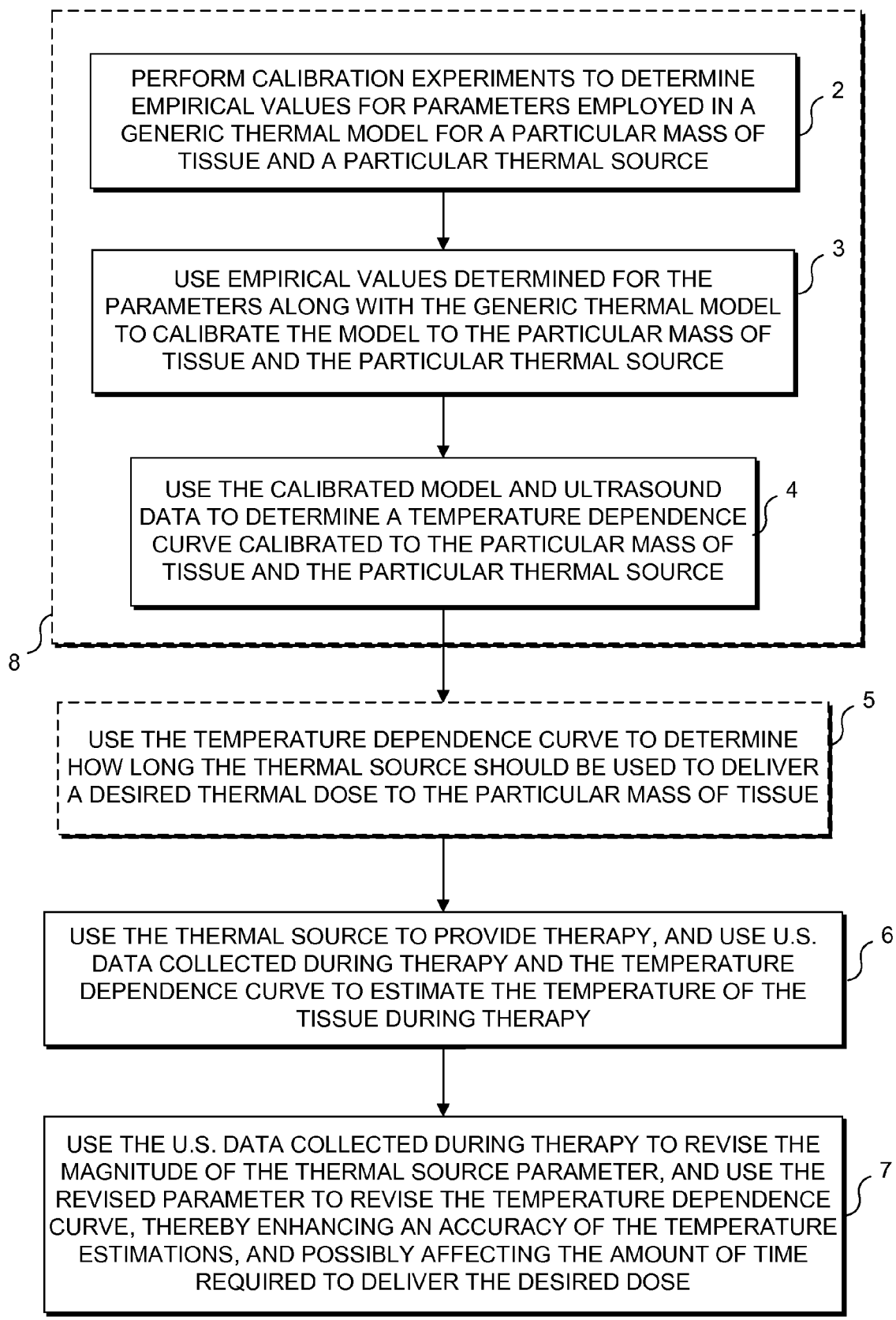
FIG. 1A is a high level flowchart schematically illustrating the overall steps of an exemplary method for non-invasively estimating tissue temperature during thermal therapy, using ultrasound data.
Figure 1B:
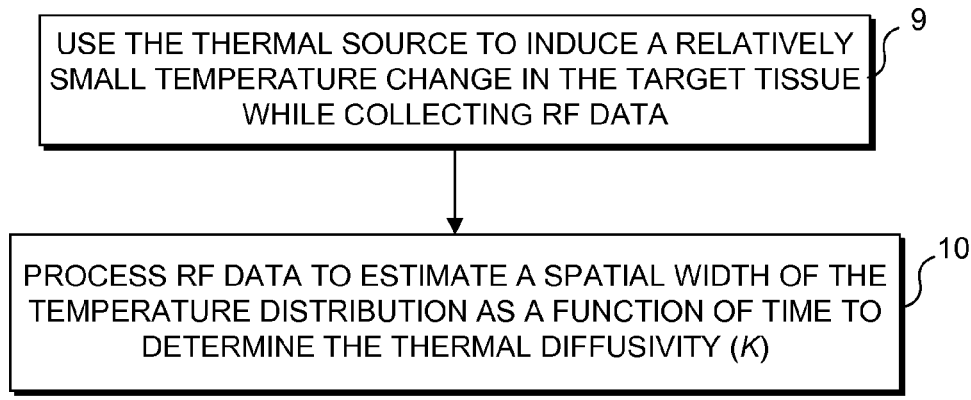
FIG. 1B is a high level flowchart schematically illustrating the overall steps for performing a first of two calibration experiments required to implement the method of FIG. 1A.
Figure 1C:
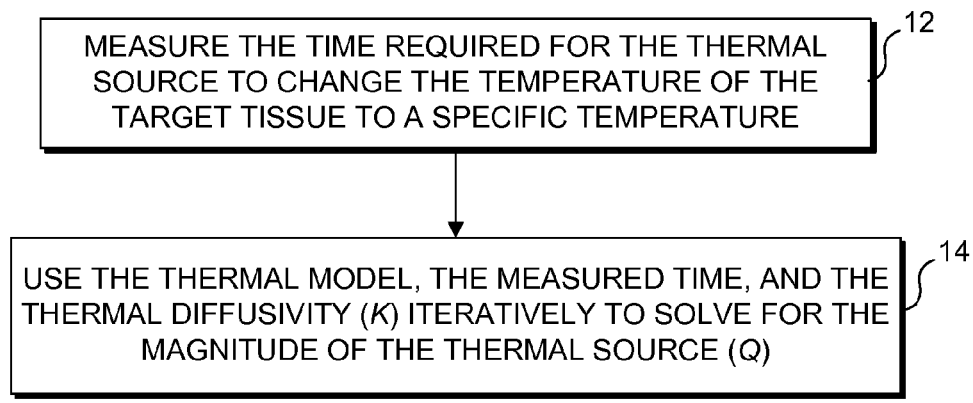
FIG. 1C is a high level flowchart schematically illustrating the overall steps for performing a second of the two calibration experiments required to implement the method of FIG. 1A.
Figure 2A:
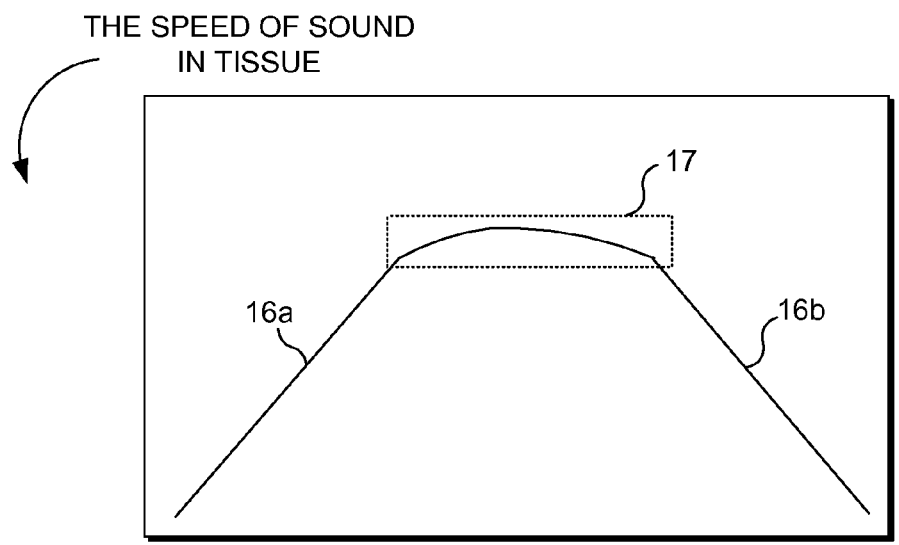
Figure 2B:
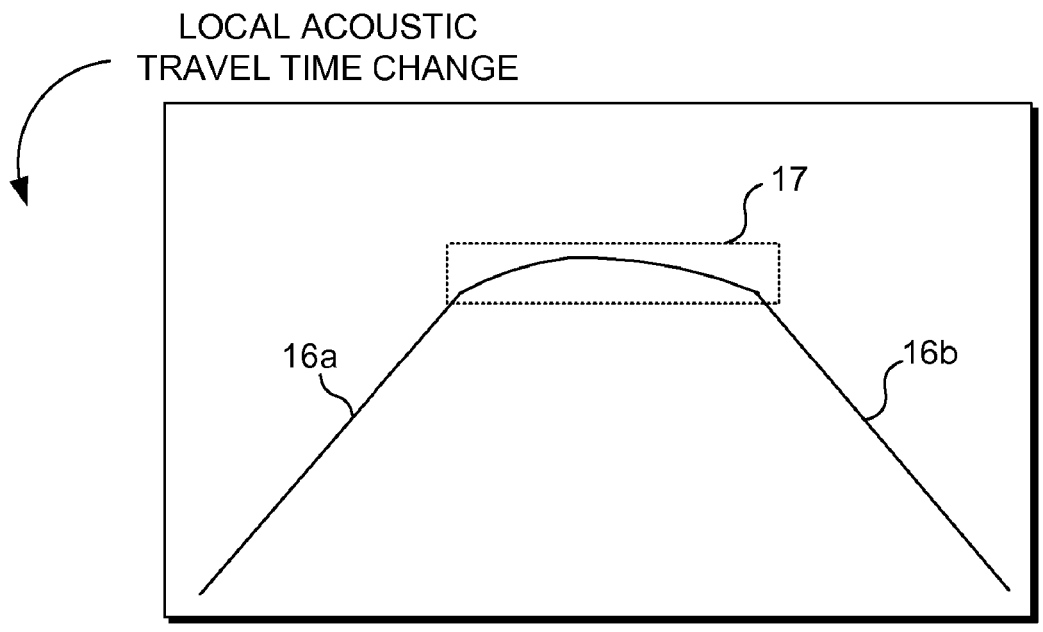
Figure 2C:
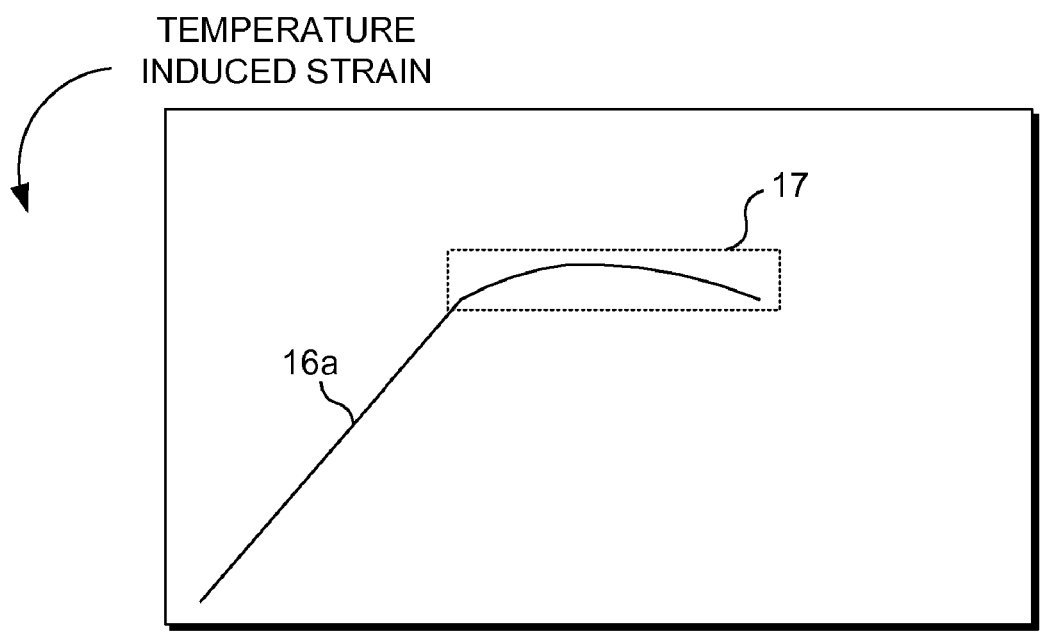
Figure 2D:
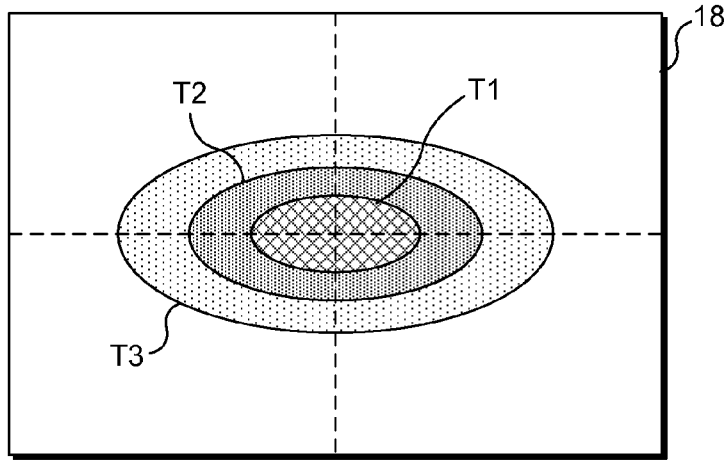
Figure 3A:
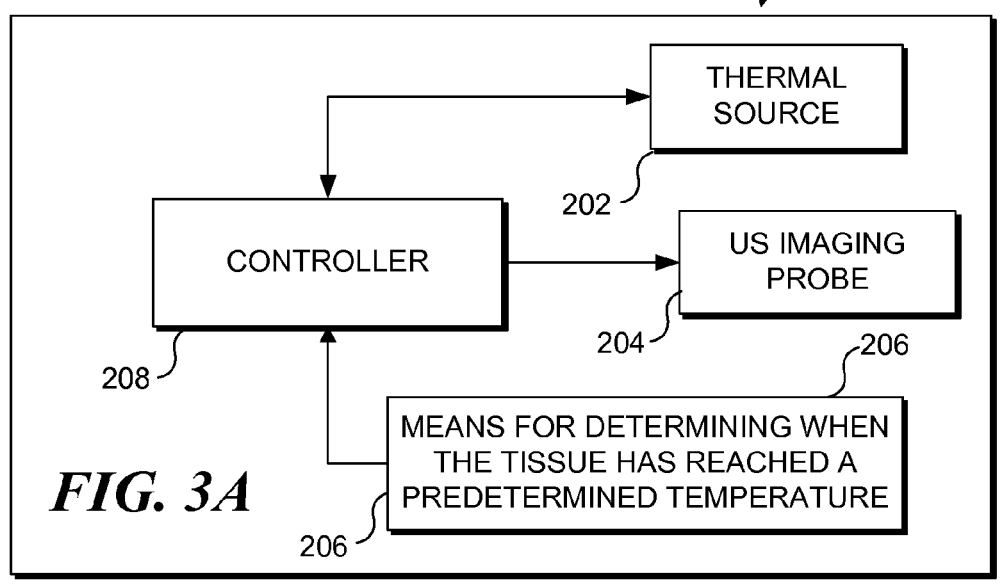
Figure 3B:
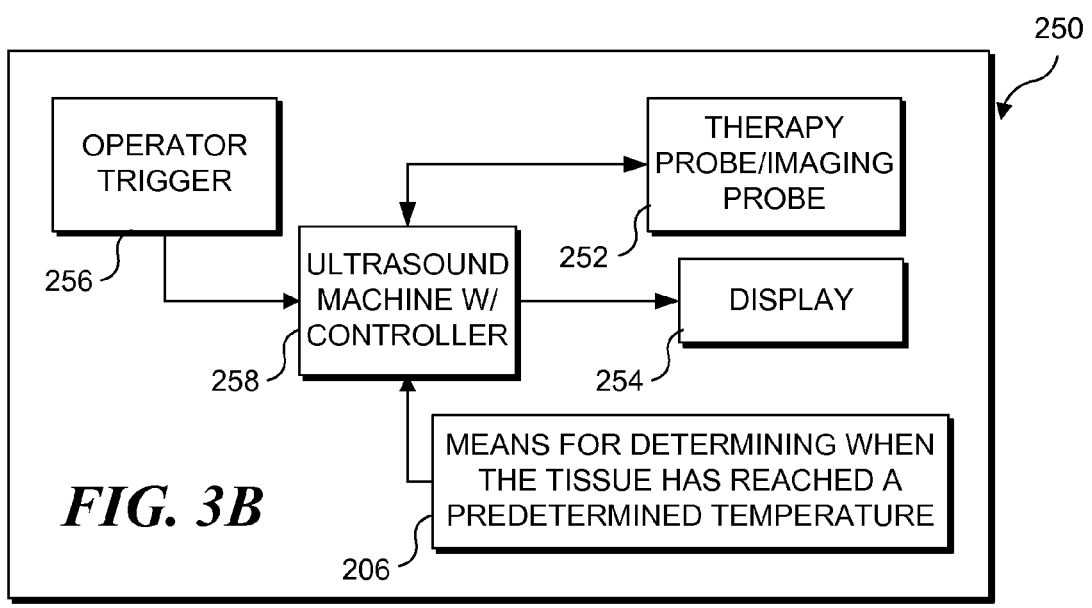
Figure 3C:
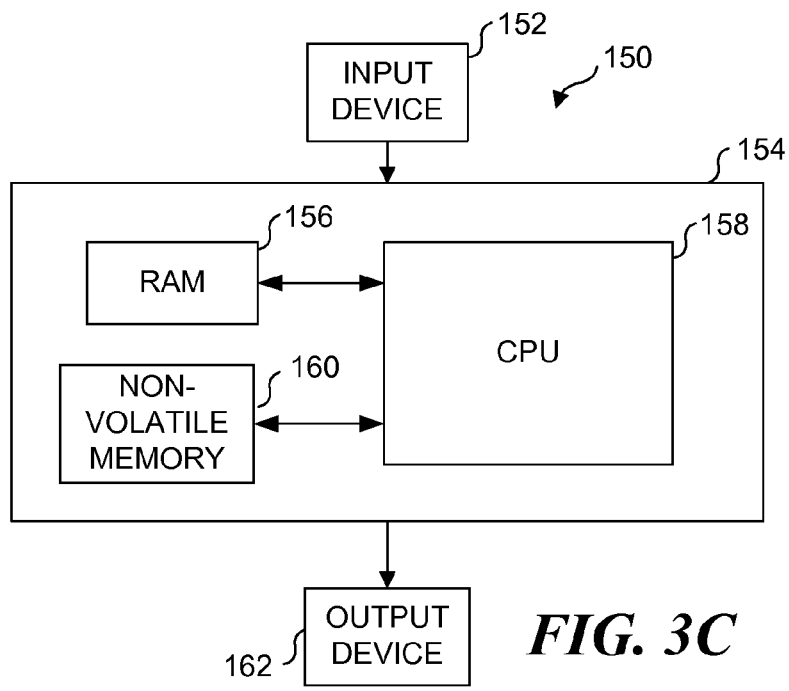
Figure 6:
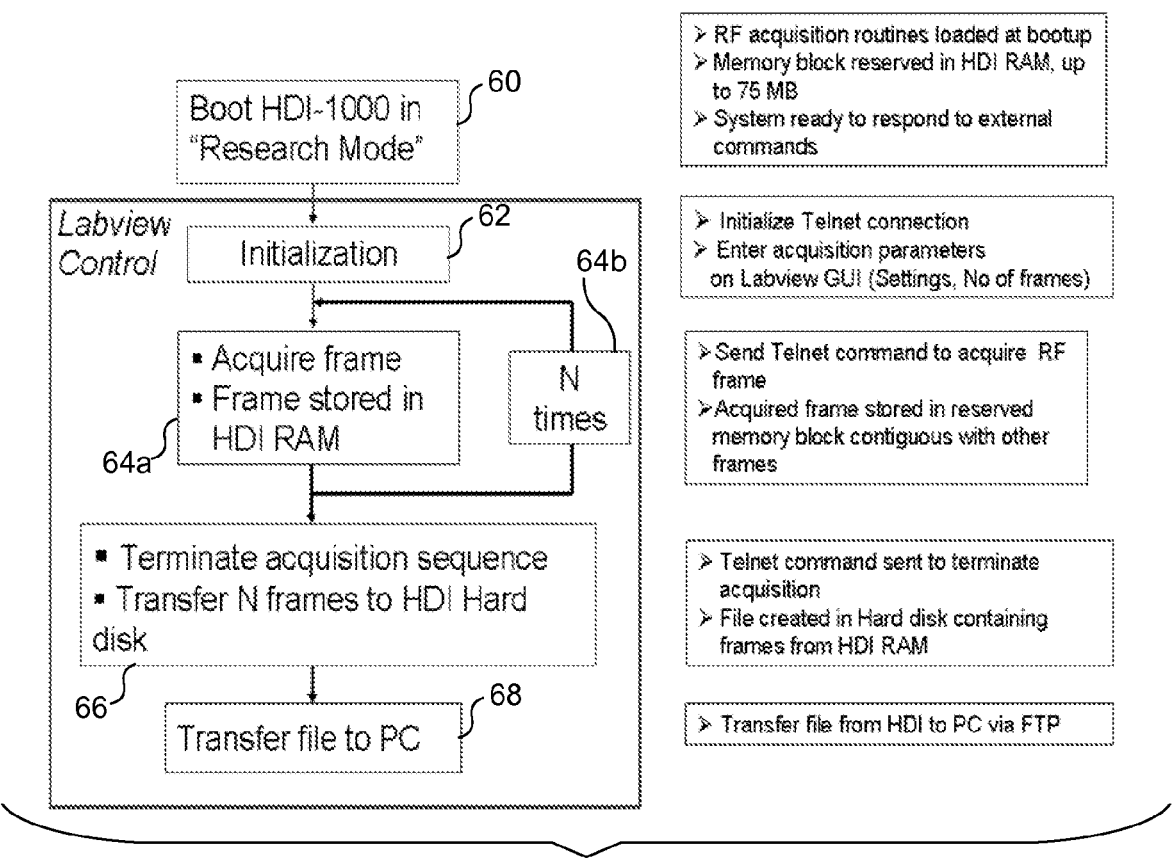
Figure 4:
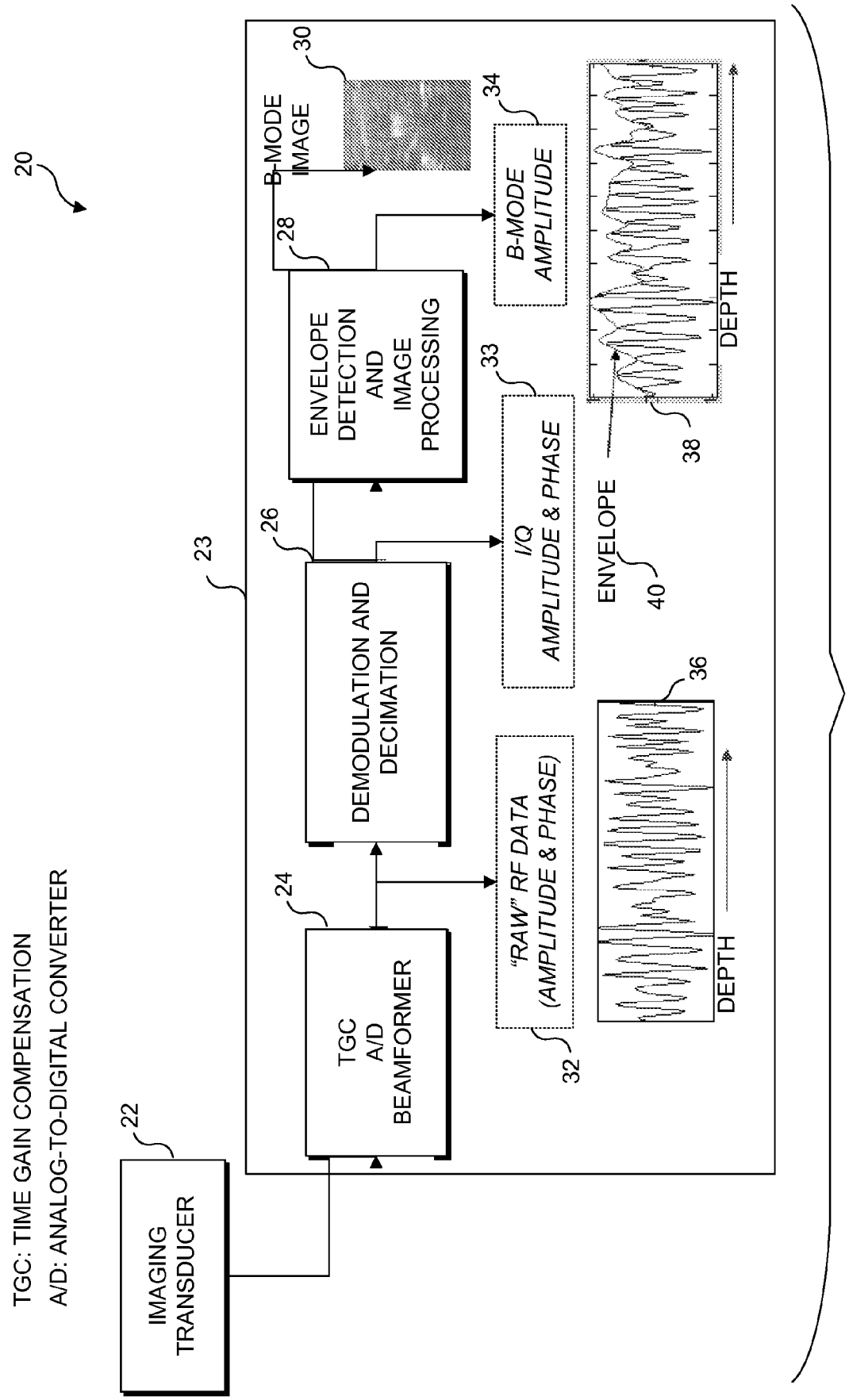
Figure 5:
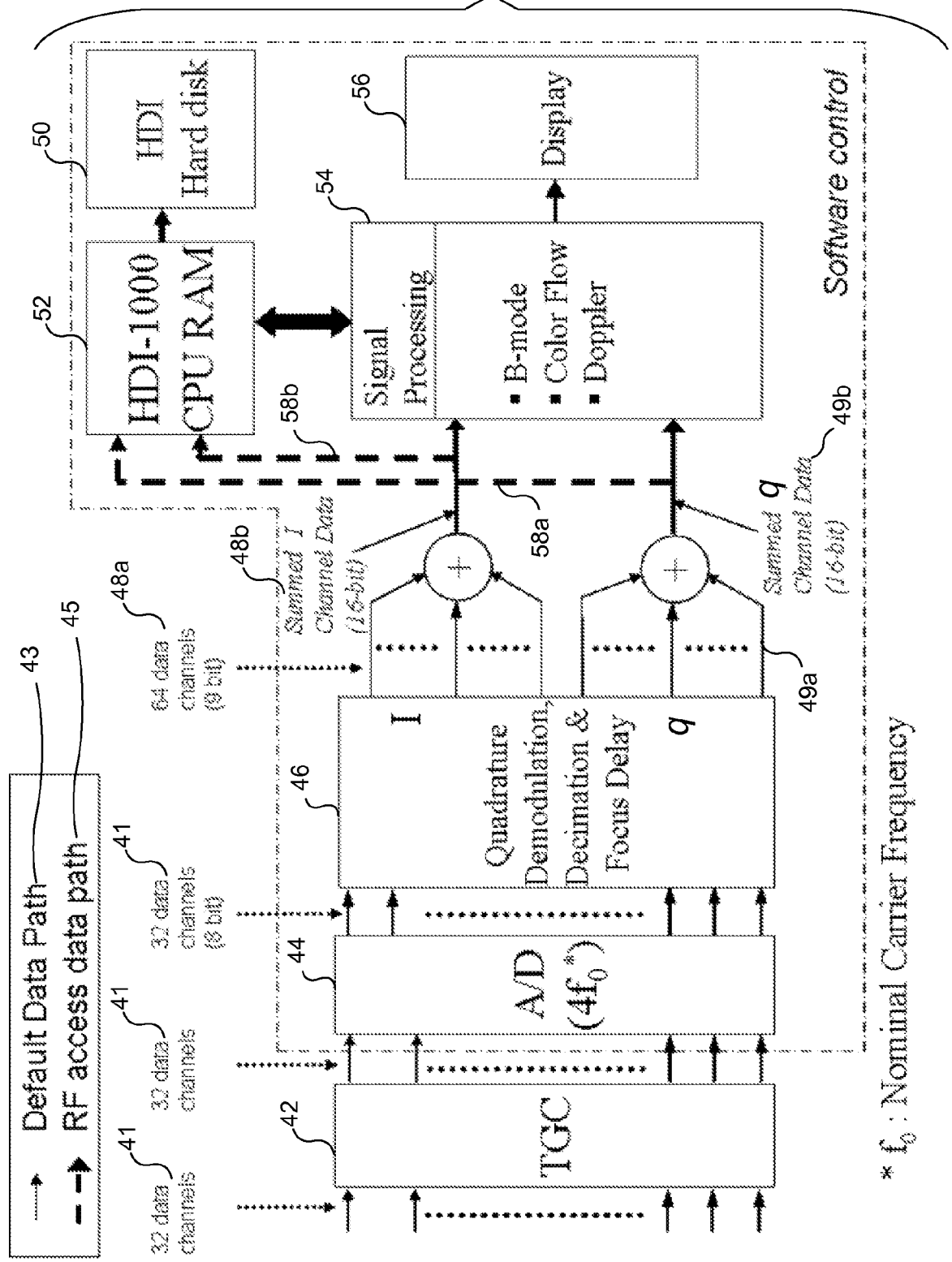
Figure 10A:
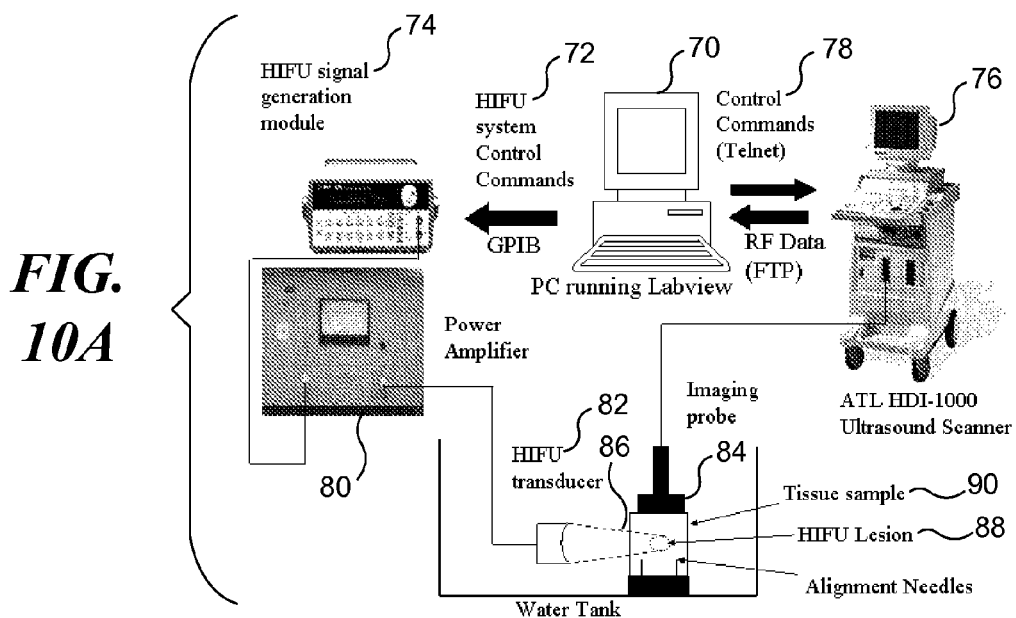
Figure 10B:
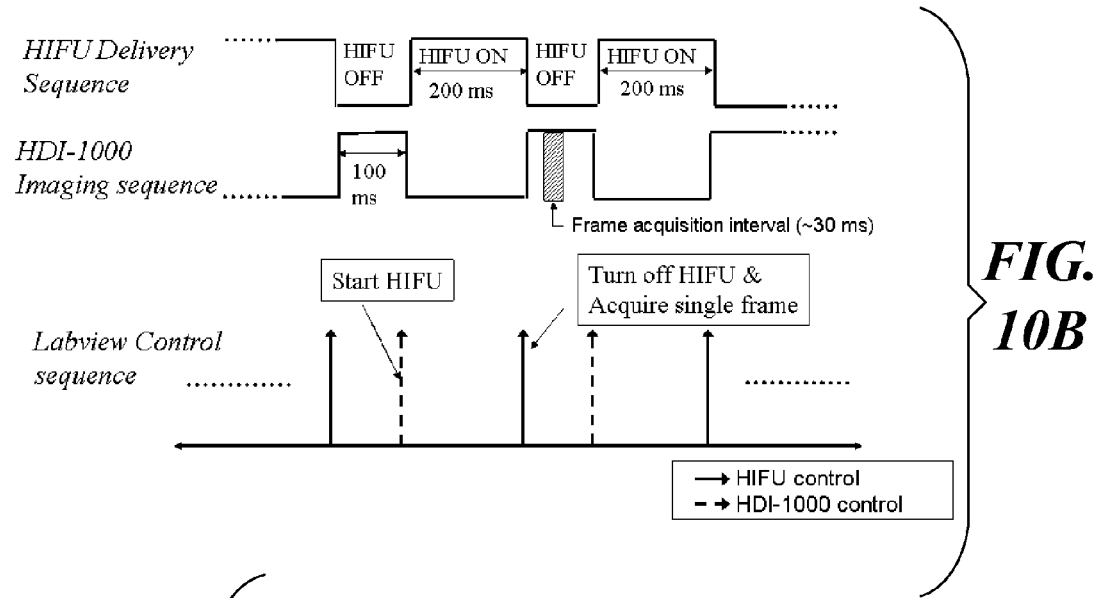
Figures 11A, 11B, 11C:
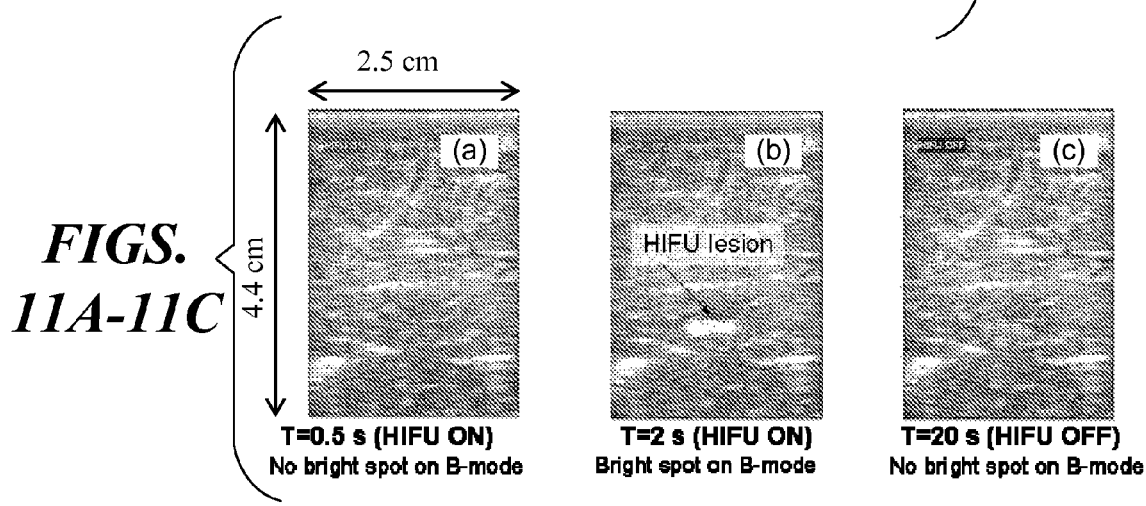
Figure 12:
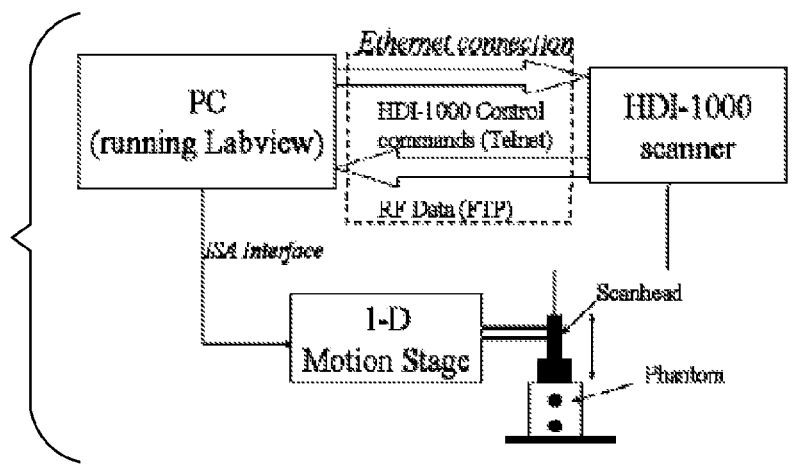
Figures 13A, 13B, 13C:
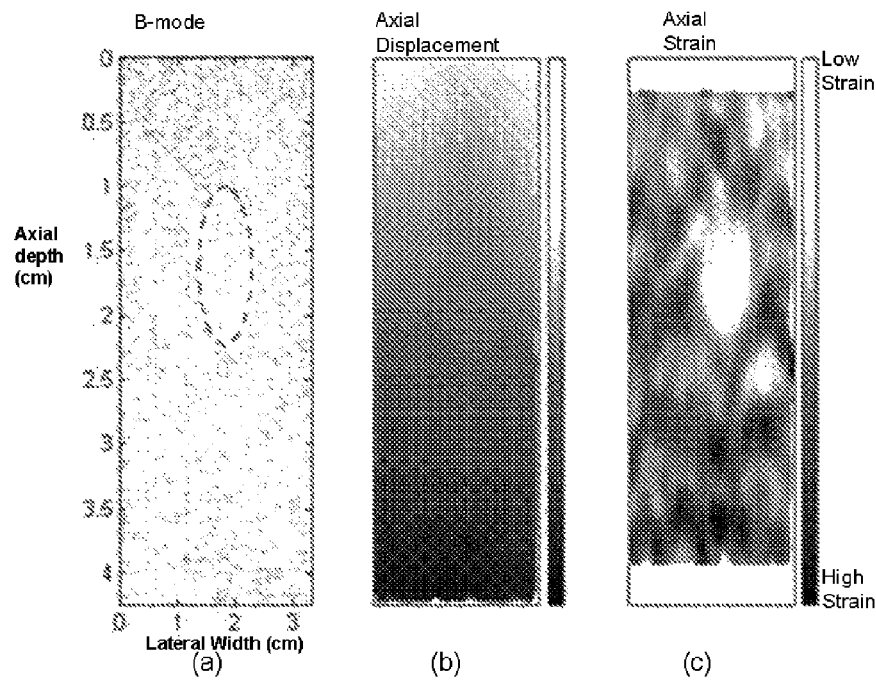
Figure 15:
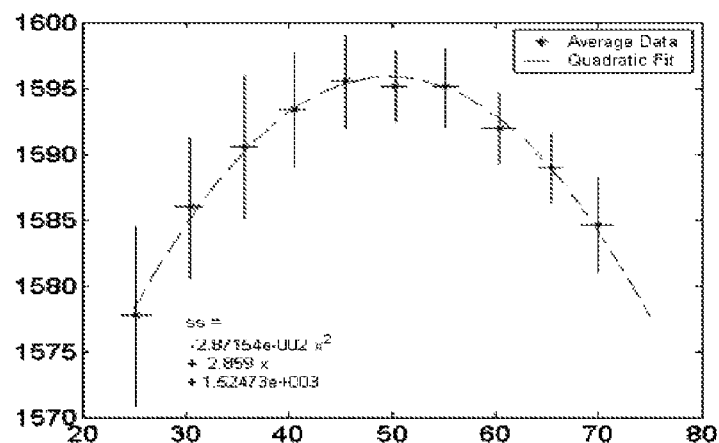
Figure 23:
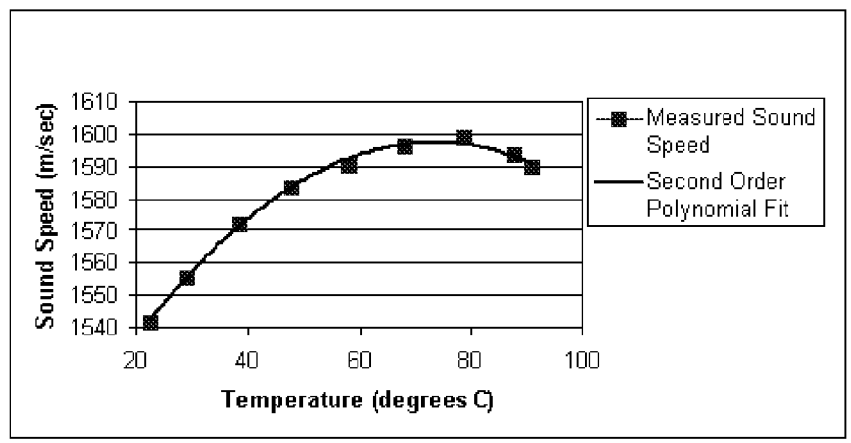
Figure 24:
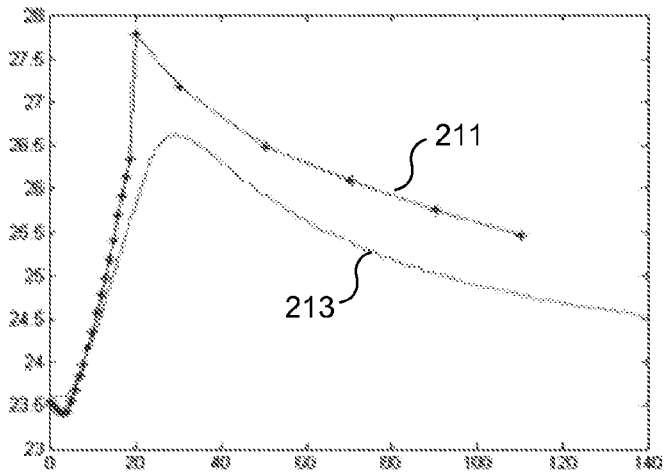
Figure 25:
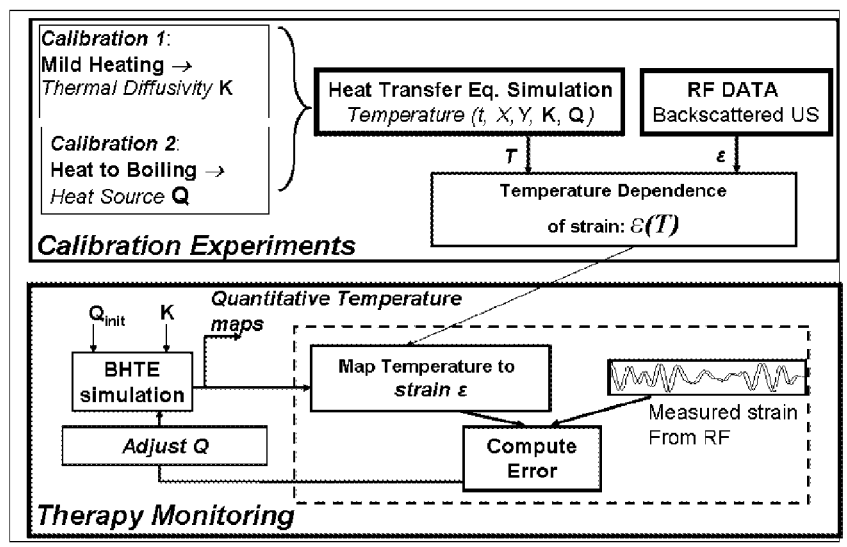
Figures 26A, 26B, 26C:
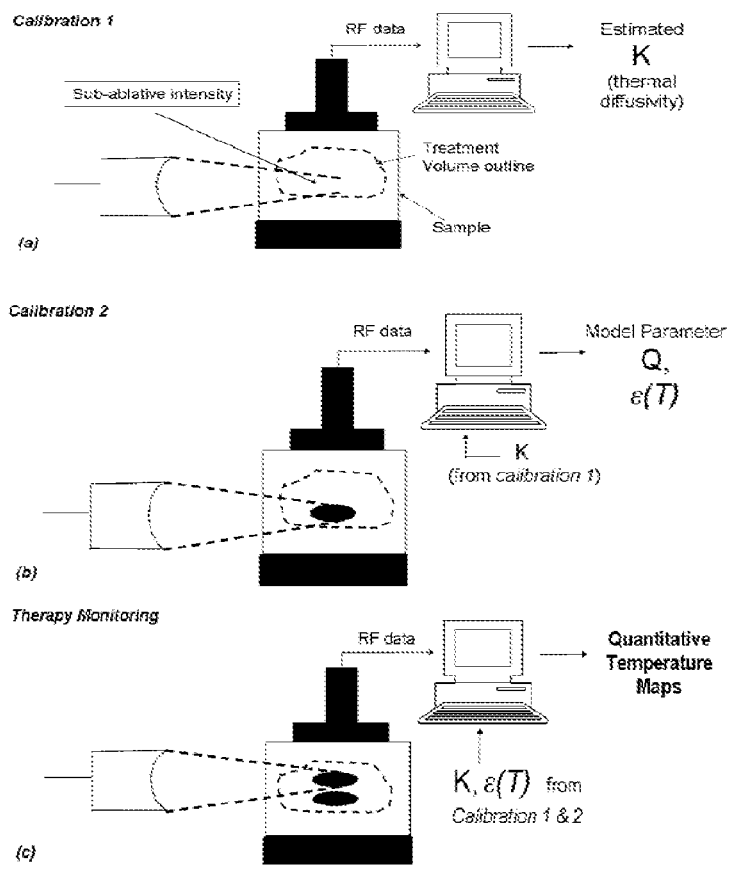
Figure 27:
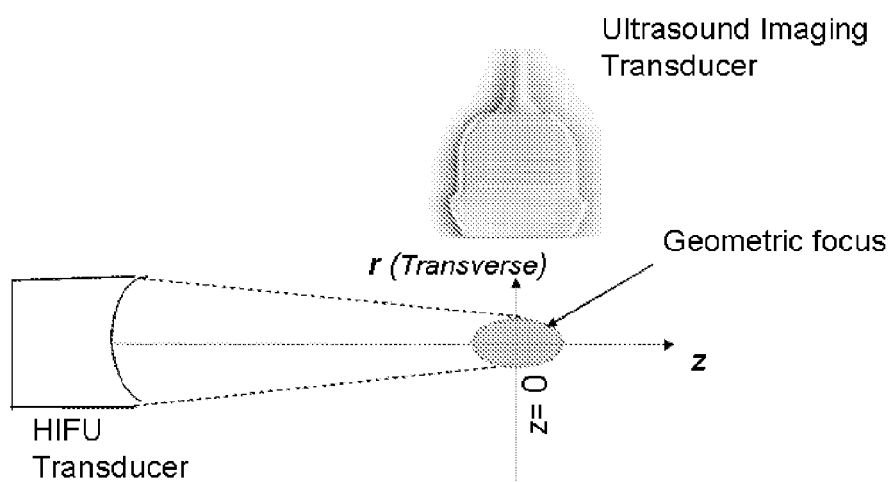
Figure 28:
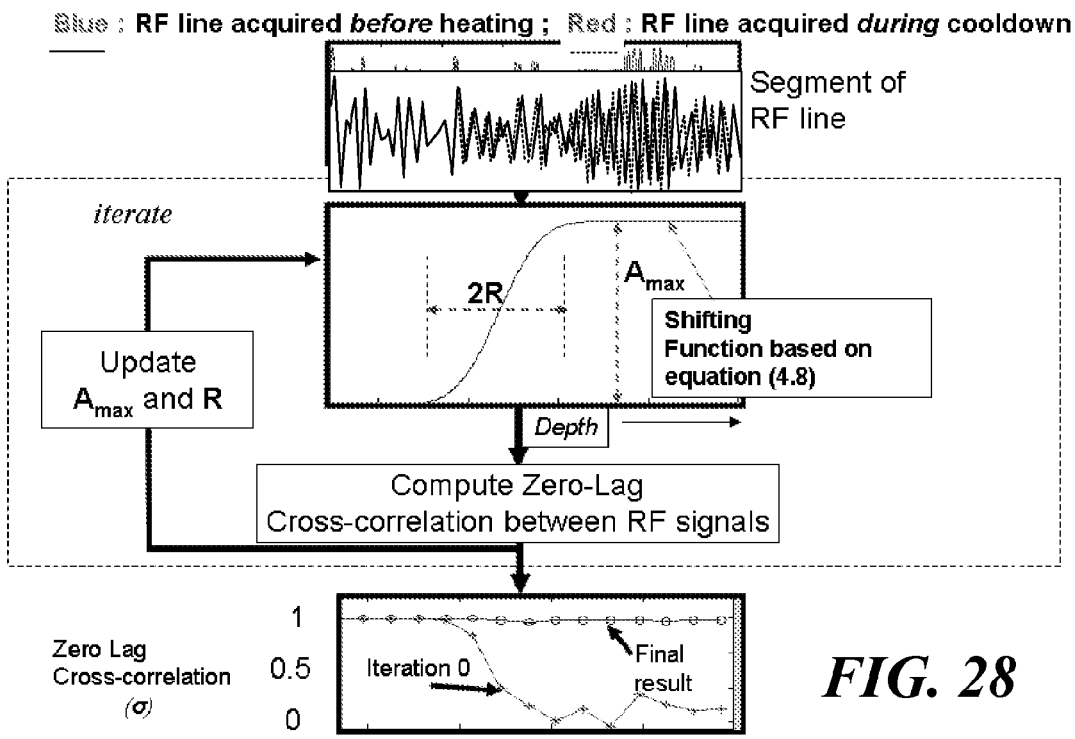
Figures 29A, 29B:
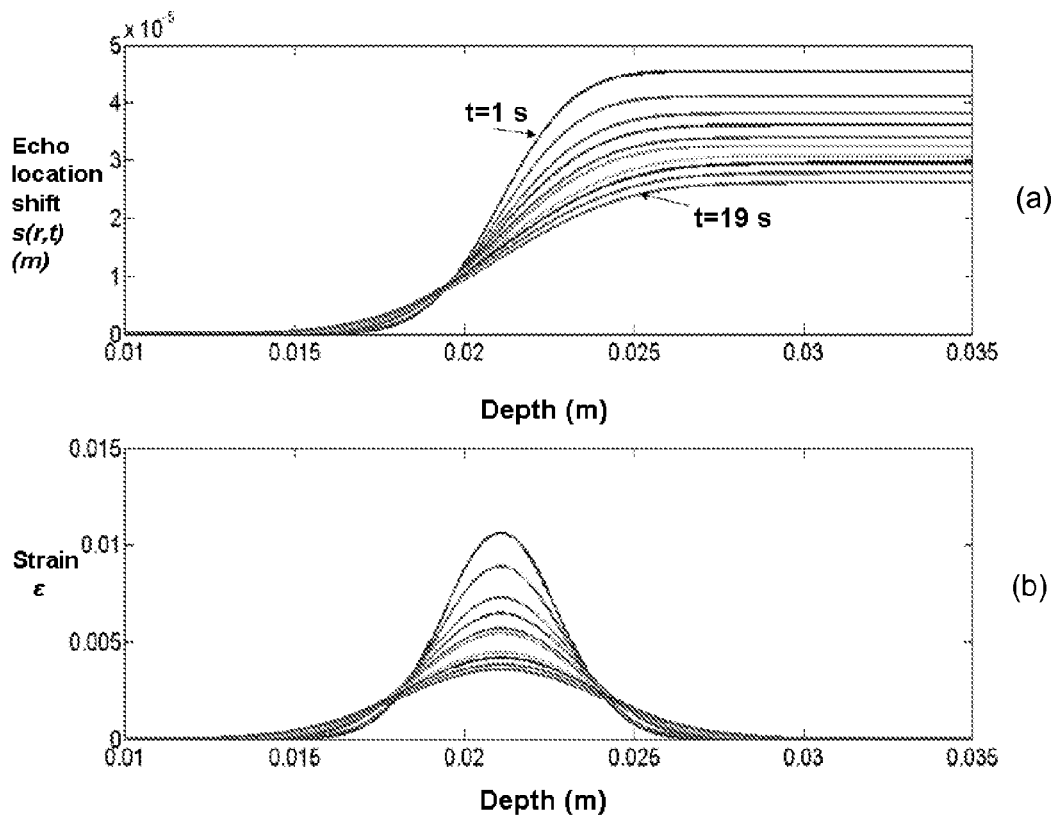
Figure 29C:
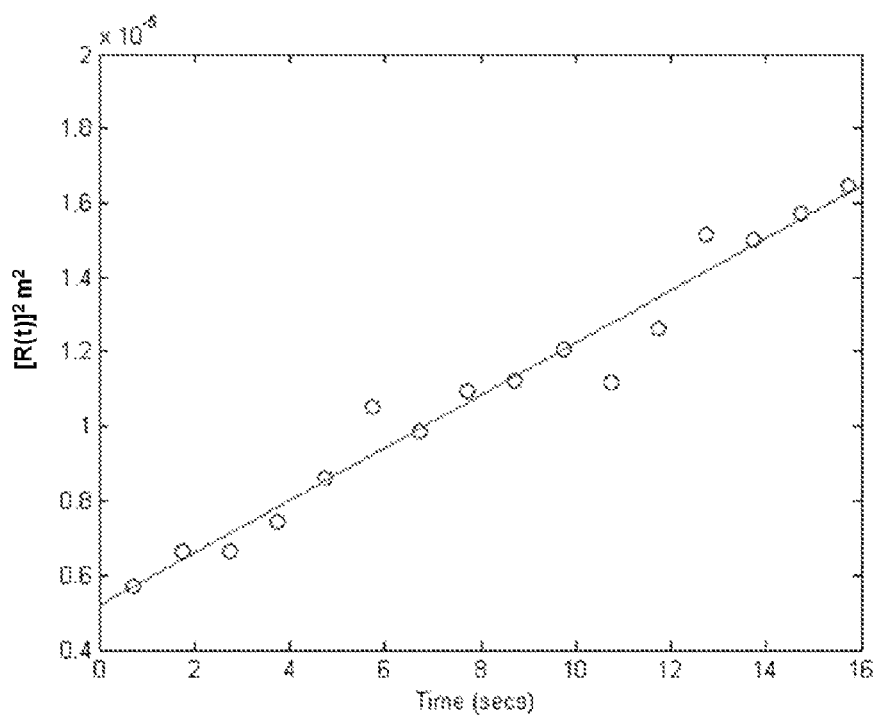
Figures 29D, 29E:
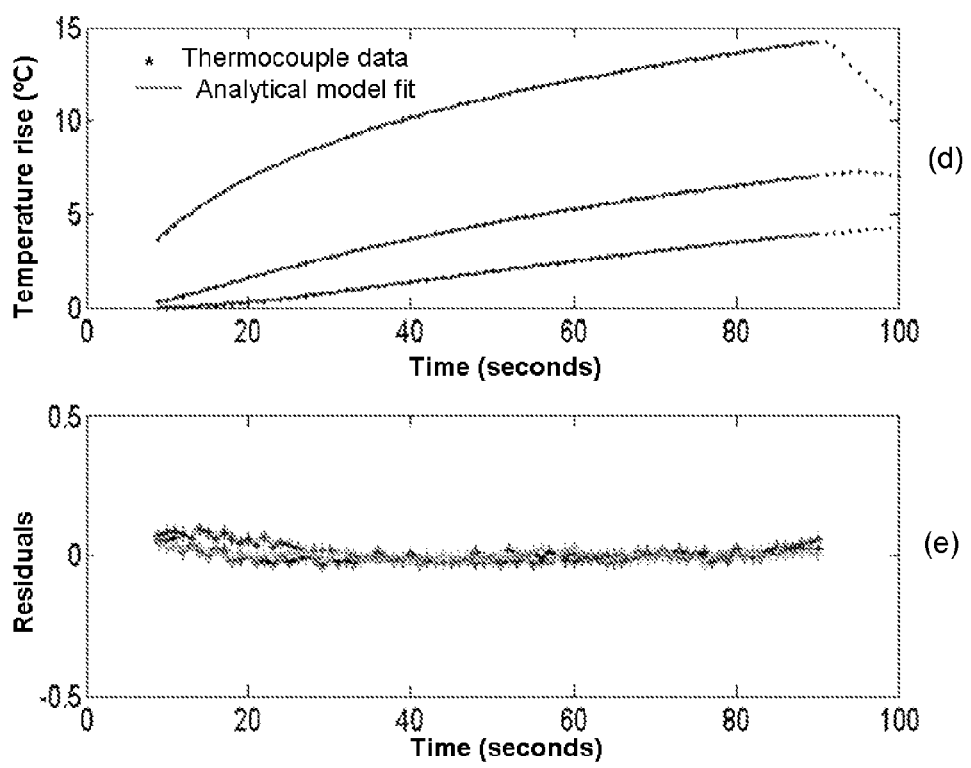
Figure 30A:
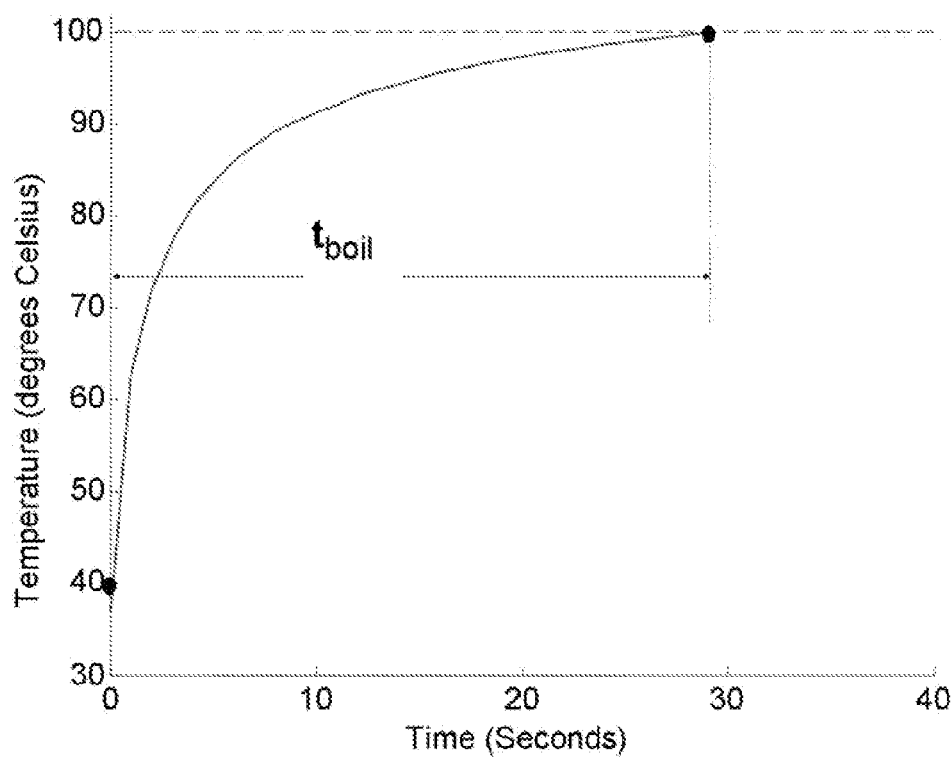
Figures 30B, 30C, 30D:
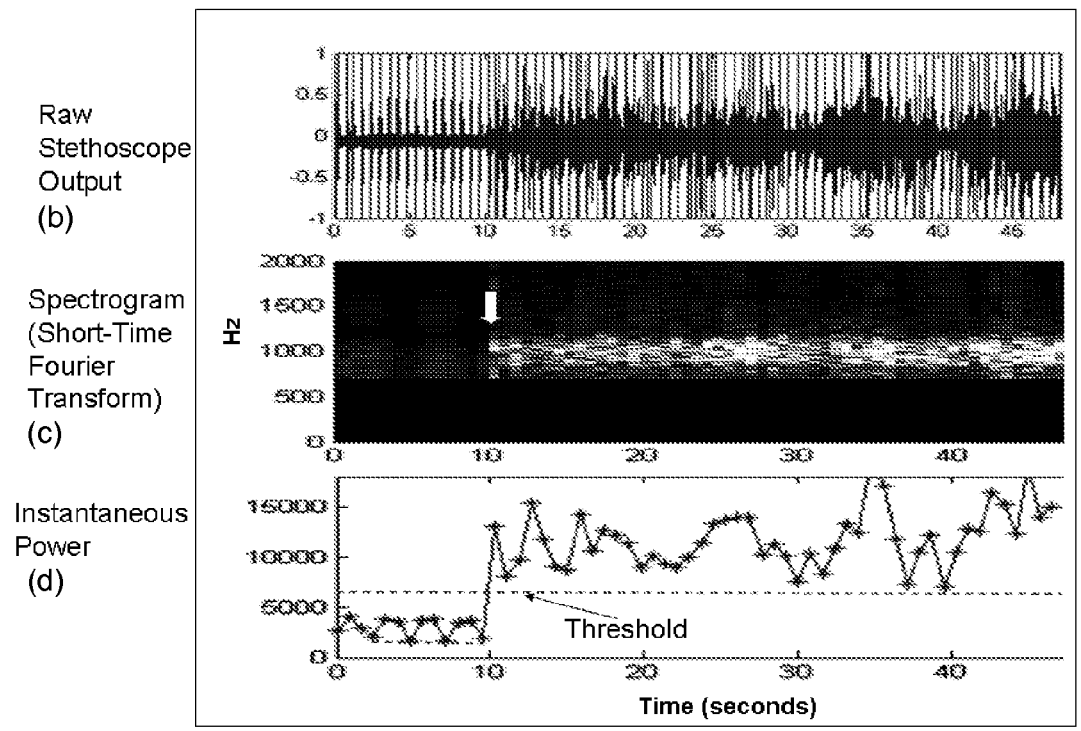
Figure 30E:
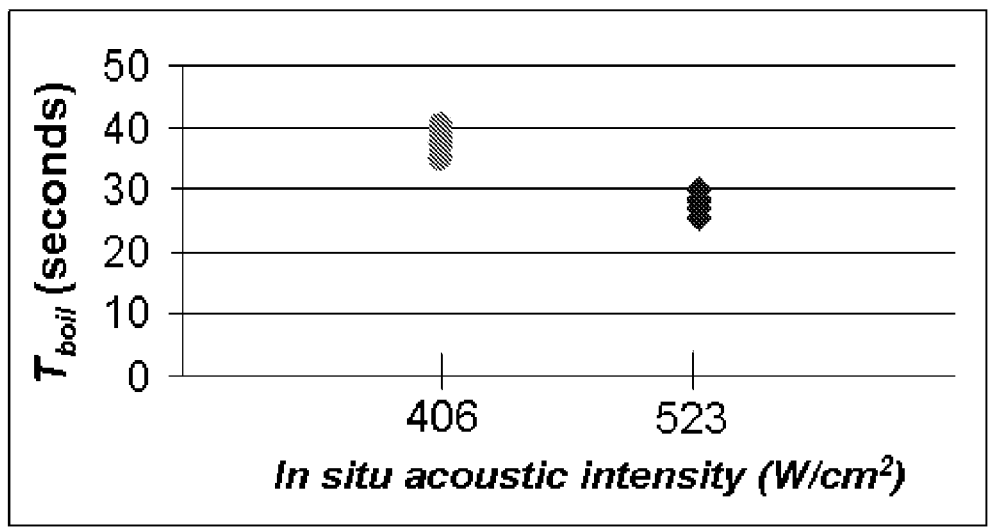
Figure 30F:
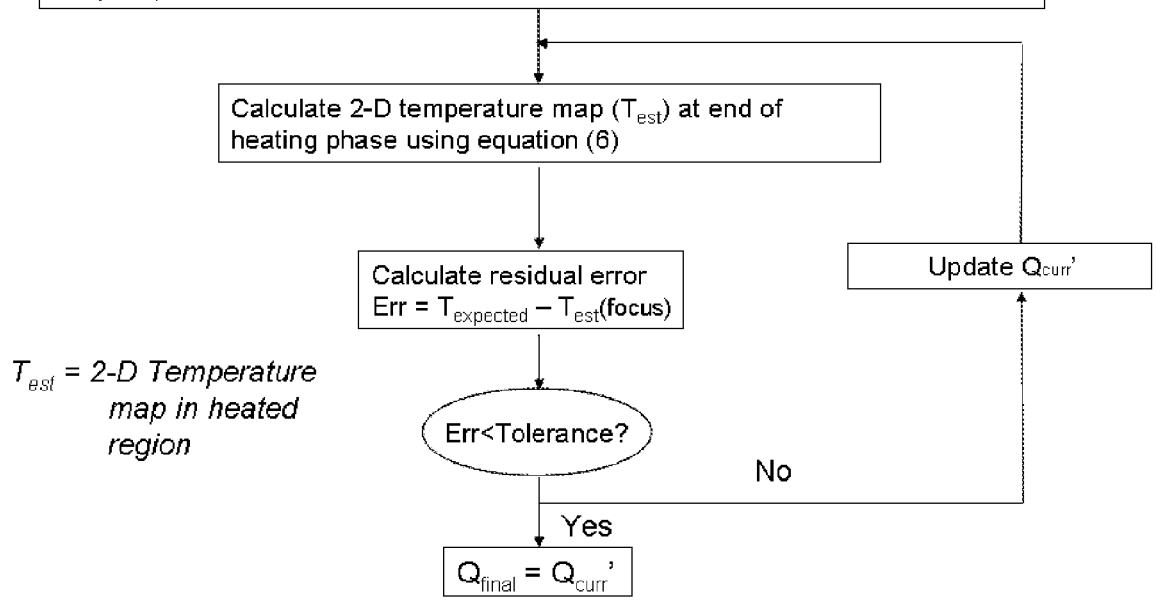
Figure 31A:
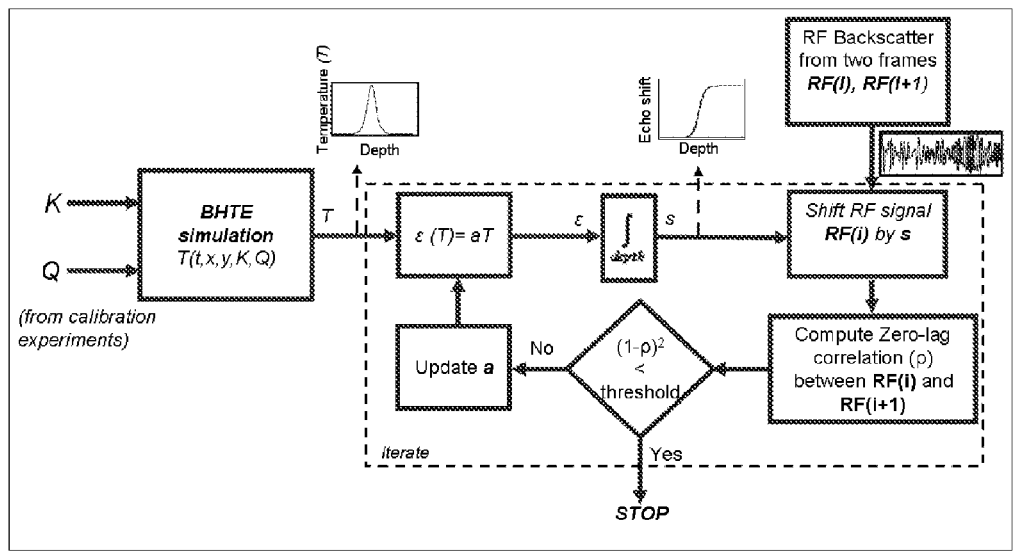
Figure 31B:
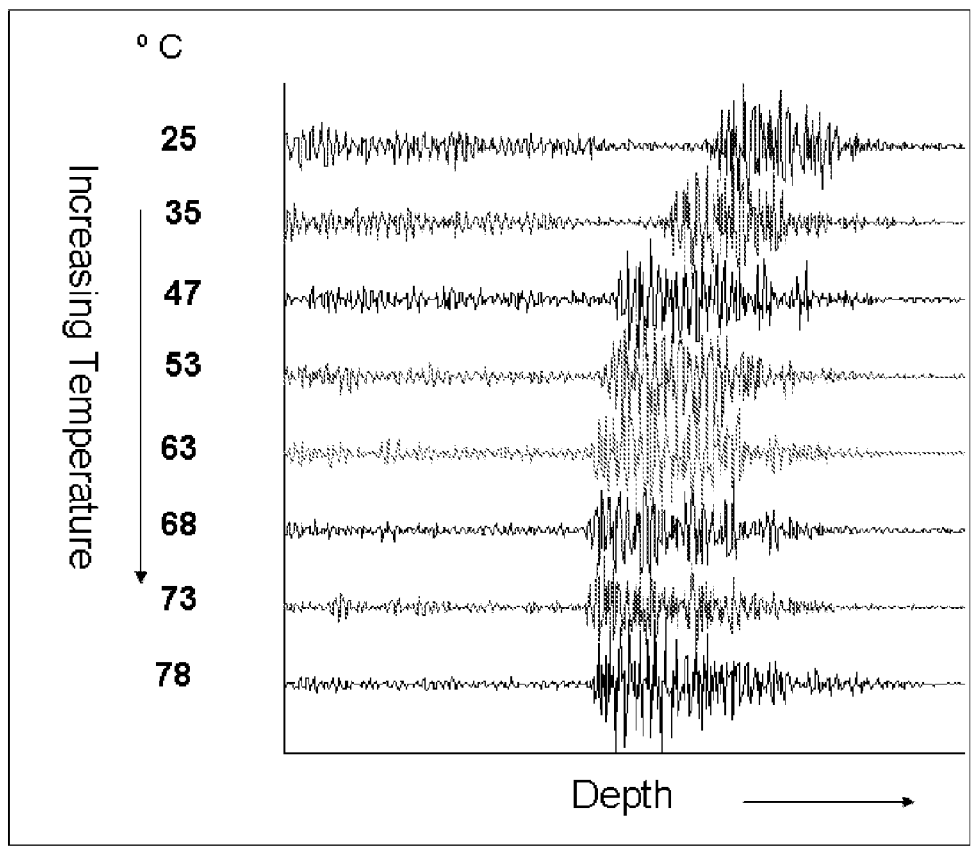
Figure 31C:
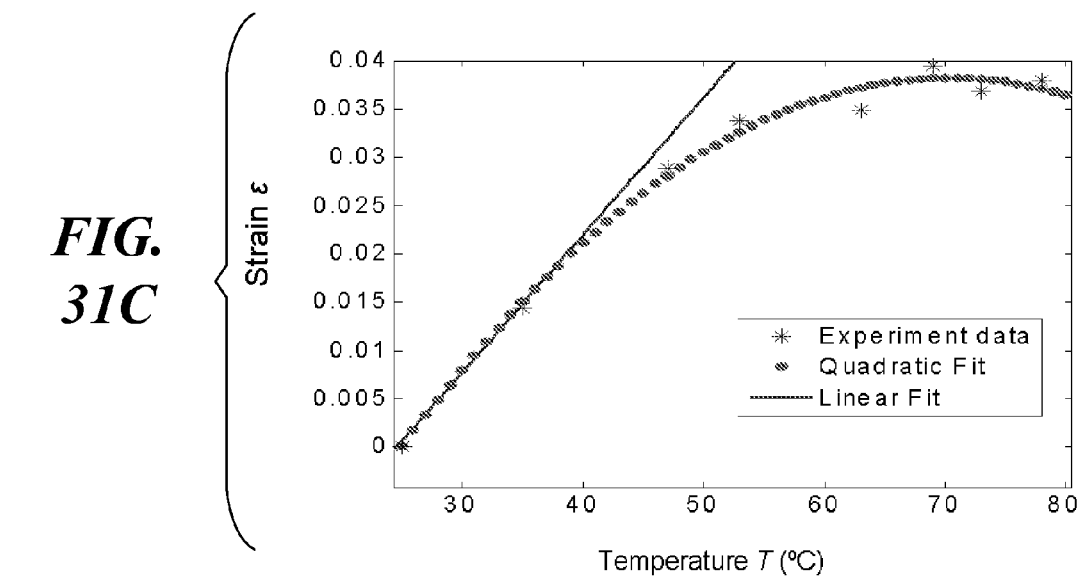
Figure 31D:
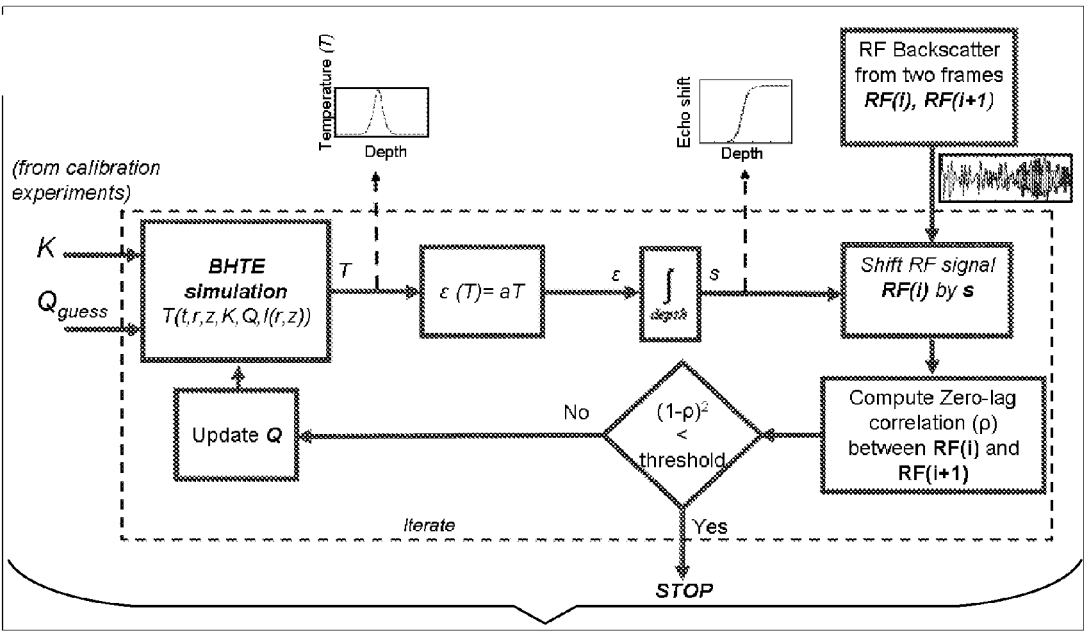
Figure 31F:
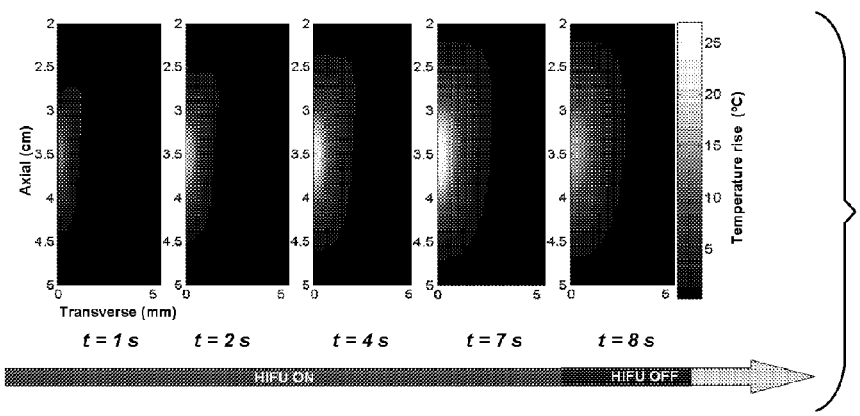
Figure 31E:
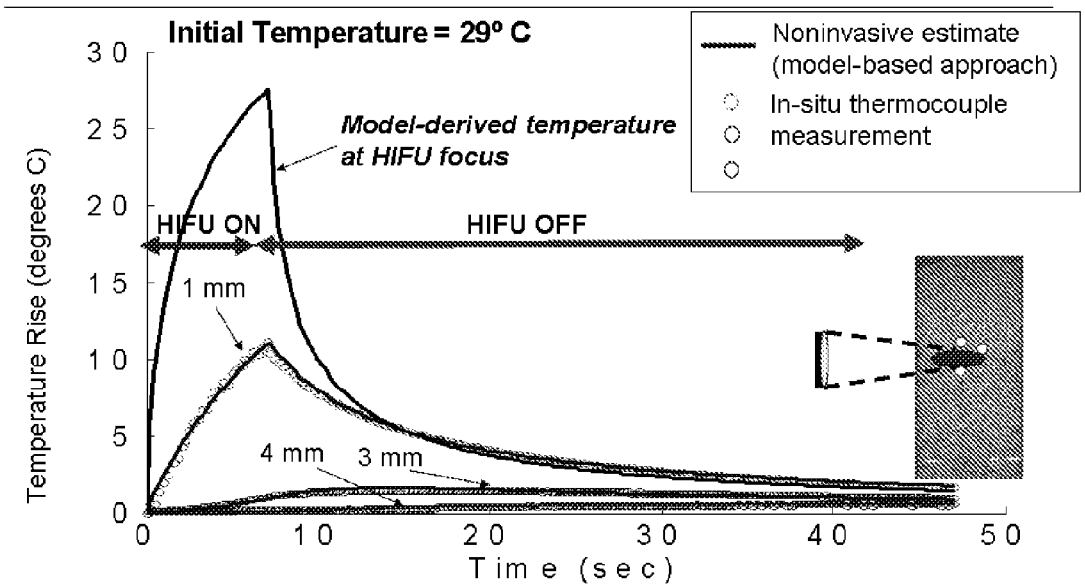
Figure 31G:
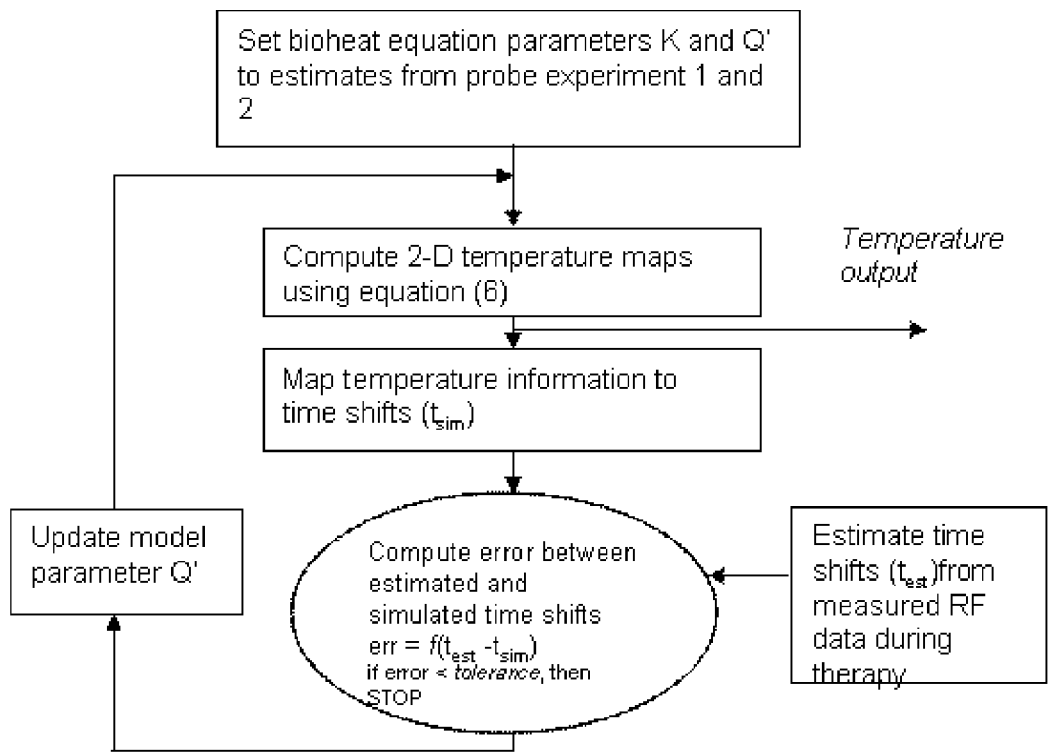

FIGS. 2A-2C graphically illustrate exemplary temperature dependence curves, $c(T)$, $\delta(T)$, and $\epsilon(T)$, respectively, which can be obtained using the method of FIG. 1A;

FIG. 2D schematically illustrates an exemplary spatio-temporal temperature map that can be obtained from the calibrated thermal model obtained using the method of FIG. 1A;

FIG. 3A is a block diagram schematically illustrating the functional elements in an exemplary system for implementing the method of FIG. 1A;

FIG. 3B is a block diagram schematically illustrating the basic elements in an exemplary system based on that of FIG. 3A, in which the thermal source is an ultrasound transducer;

FIG. 3C is a block diagram schematically illustrating the basic elements in an exemplary computing device that can be used as a controller for the systems of FIGS. 3A and 3B;

FIG. 4 is a functional block diagram schematically illustrating exemplary signal processing in an ultrasound imaging system (e.g., the ATL HDI 1000™) utilized in empirical studies;

FIG. 5 is a functional block diagram schematically illustrating additional details and functionalities of the ultrasound imaging system (the ATL HDI 1000™) utilized in empirical studies used to validate the concepts disclosed herein;

FIG. 6 is yet another functional block diagram illustrating operation of the ultrasound imaging system (the ATL HDI 1000™) employed in the empirical studies;

FIG. 7A schematically illustrates a B-mode image obtained using a full lateral width scan;

FIG. 7B schematically illustrates a B-mode image obtained using a reduced sector width scan;

FIG. 7C graphically illustrates a relationship between a number of frames of ultrasound data acquired per second and sector scan width;

FIG. 8A schematically illustrates a B-mode image obtained using a default scan-line spacing;

FIG. 8B schematically illustrates a B-mode image obtained using sparse scan-line acquisition;

FIG. 9 schematically illustrates an exemplary B-mode image reconstructed from RF data acquired during HIFU, showing some interference due to the HIFU beam;

FIG. 10A schematically illustrates an exemplary empirical system employed to validate the concepts disclosed herein;

FIG. 10B schematically illustrates an exemplary timing diagram enabling HIFU and imaging ultrasound to be synchronized to avoid the interference illustrated in FIG. 9;

FIGS. 11A-11C are exemplary B-mode images, illustrating the visualization of a bright hyperechoic spot at the focal point of the HIFU beam during HIFU therapy;

FIG. 12 schematically illustrates a modification of the empirical ultrasound system to perform elastographic measurements;

FIGS. 13A-13C graphically illustrate exemplary data obtained using the modified system of FIG. 12;

FIGS. 14A-14D schematically illustrate exemplary temperature related echo shifts;

FIG. 15 graphically illustrates an empirically measured c(T) temperature dependence curve, similar to that shown in FIG. 2A;

FIG. 16A schematically illustrates an exemplary configuration of an imaging transducer and an image acquisition plane employed to collect RF data to facilitate non-invasive temperature estimates;

FIG. 16B schematically illustrates an exemplary organization of the RF data set collected using the configuration of FIG. 16A;

FIG. 16C is a block diagram representing an exemplary processing scheme for the RF data set of FIG. 16B;

FIG. 17 is a composite image schematically illustrating empirical testing of the concepts disclosed herein using a bovine liver;

FIG. 18 schematically illustrates the relative orientations of a HIFU transducer, an imaging transducer, and a plane of lesion formation implemented in an exemplary scanned lesion protocol;

FIG. 19A is an exemplary series of B-mode images acquired at different times;

FIG. 19B is a series of strain (C) maps corresponding to the B-mode images of FIG. 19A;

FIG. 20 graphically illustrates a relationship between a Gaussian radius and time for a one-dimensional (1-D) strain profile measured during HIFU therapy;

FIG. 21 graphically illustrates a relationship between a strain amplitude and time for a 1-D strain profile measured during HIFU therapy;

FIG. 22 schematically illustrates an exemplary empirical system employed to obtain independent estimates of the c(T) curve for validation purposes;

FIG. 23 graphically illustrates the c(T) curve measured for a gel phantom using the system of FIG. 21A;

FIG. 24 graphically illustrates temperature readings measured using thermocouples for comparison to temperatures estimated using RF data;

FIG. 25 is a functional block diagram of exemplary steps employed to estimate parameters K and Q', and non-invasively estimate temperature during HIFU therapy (such steps being generally consistent with the flowcharts of FIG. 1A-1C);

FIGS. 26A-26C schematically illustrate how the non-invasive model-based temperature estimation approach disclosed herein can be implemented in a clinical setting for therapy monitoring;

FIG. 27 schematically illustrates an exemplary orientation of a HIFU transducer, an ultrasound imaging probe and a geometric focus of the HIFU beam for implementing the concepts disclosed herein;

FIG. 28 is a functional block diagram illustrating exemplary steps for estimating the K parameter;

FIGS. 29A and 29B graphically illustrate model-derived $s(r,t)$ and $\epsilon(r,t)$ curves at various times after a HIFU heating pulse has been turned off, for an RF data set acquired in an alginate phantom;

FIG. 29C graphically illustrates estimated R(t) values as a function of time, with a least squares linear fit to the data points;

FIG. 29D graphically represents typical thermocouple profiles obtained during transient hot wire experiments, with superimposed analytical model data;

FIG. 29E graphically illustrates a residual error between the thermocouple data and the model data of FIG. 29D;

FIG. 30A graphically illustrates a typical temperature versus time relationship for temperature evolution at the geometric focus of a HIFU transducer;

FIG. 30B graphically illustrates a typical time domain output for acoustic data collected by an acoustic sensor while boiling is induced by a HIFU transducer;

FIG. 30C graphically illustrates the data from FIG. 30B after the data have been processed using a short-time Fourier transform (STFT);

FIG. 30D graphically illustrates power levels per unit time computed from the spectrum of FIG. 30C;

FIG. 30E graphically illustrates estimated boiling onset times for five independent exposures using two different HIFU intensities, indicating a good reproducibility in the boiling times for each of the intensities;

FIG. 30F is a flowchart illustrating exemplary steps of an iterative algorithm for estimating Q' by detecting noise associated with the onset of boiling;

FIG. 31A is a flowchart illustrating exemplary steps for estimating a strain curve (i.e., $\epsilon(T)$) using RF data;

FIG. 31B graphically illustrates RF echoes over an axial distance for a single scan-line, clearly showing echo shifts;

FIG. 31C graphically illustrates a strain and temperature relationship (i.e., an $\epsilon(T)$ curve) developed from echo shifts identified in RF data;

FIG. 31D is a functional block diagram illustrating exemplary steps for iteratively optimizing the value of Q' during therapy;

FIG. 31E graphically illustrates a comparison of non-invasively estimated temperatures and temperature measured using implanted thermocouples;

FIG. 31F is a composite image of a plurality of spatial maps of the temperature evolution around a HIFU focus; and FIG. 31G is a flowchart illustrating exemplary steps for adaptively changing Q' using backscatter data acquired during the therapy, to enhance an accuracy of temperature estimations derived from RF data during HIFU therapy.

DESCRIPTION

Figures and Disclosed Embodiments Are Not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

The following definitions should be used to interpret the disclosure and claims that follow. The term "temperature dependence curve" is intended to refer to a relationship between some determinable parameter (the speed of sound in tissue, the change in the speed of sound in tissue, or strain, as will be discussed in greater detail below) and the temperature of the tissue. FIGS. 2A-2C graphically illustrate various temperature dependence curves. The term "spatio-temporal temperature map" is intended to refer to a map of a region of tissue showing temperatures of the tissue at specific times. FIG. 2D schematically illustrates an exemplary spatio-temporal temperature map.

The Description is organized as follows. First, several high level flow charts describing the overall concepts encompassed herein are described.

Second, high level functional block diagrams of exemplary apparatus that can be used to implement the techniques disclosed herein will be provided.

Third, a detailed description of an empirical system used to develop the disclosed techniques is provided. The operation of the system is discussed along with a description of exemplary operating modes and exemplary performance specifications. The empirical system was used in all subsequently described experiments.

Fourth, a mathematical model defining the relationship between temperature and ultrasound backscatter related to changes in speed of sound and thermal expansion is presented. Two signal processing-based algorithms designed to extract information from the ultrasound backscatter related to change in tissue properties associated with therapy are described. Results obtained by applying these non-invasive techniques to in vitro tissue-mimicking phantoms and animal tissue experiments are presented.

Fifth, exemplary non-invasive quantitative temperature estimation techniques based on using calibration experiments and the BHTE are described in detail. The calibration procedures designed to non-invasively estimate local thermal parameters, specifically, thermal diffusivity (K) and heating rate (Q') in situ during HIFU exposures are described, followed by empirical results from validation experiments performed in tissue-mimicking phantom experiments.

Sixth, the use of the K and Q' parameters in calibrating a temperature dependence curve, and temperature monitoring during therapy, are presented.

High Level Flowcharts: FIG. 1A is a flowchart schematically illustrating steps of an exemplary method for calibrating a thermal model to a specific mass of tissue and a specific heat source. The calibrated model can then be used to predict tissue temperatures after specific periods of treatment, facilitating pre-therapy planning and the calculation of a desired thermal dose. The calibrated model and non-invasively collected ultrasound data can be used to estimate tissue temperatures during treatment. Generally, the therapy will be thermal ablation, which can be implemented using HIFU, although it should be recognized that the method can be used to estimate tissue temperature during cryogenic-based therapy as well (and also for other thermal therapies). In a block 2, calibration experiments are performed (before therapy is initiated) to determine empirical values for parameters employed in a generic thermal model. The purpose of the calibration experiments is to provide empirical values unique to a particular mass of tissue and a particular thermal source. Thus, the generic thermal model is customized (i.e., calibrated) for the particular tissue mass and the particular thermal source that will be employed. The generic thermal model can be based on the bio-heat transfer equation (BHTE, which is described below in greater detail). A first empirically determined parameter is the thermal diffusivity (K) of the tissue mass, and a second empirically determined parameter is a magnitude of the thermal source (Q'). As described in greater detail below, Q' is unique not only to each different thermal source, but to each tissue mass as well, because a portion of Q' relates to how each unique tissue mass attenuates the propagation of thermal energy from the thermal source to the target tissue. This aspect of Q' is particularly pronounced where the thermal source is a HIFU transducer, since tissue disposed between the treatment site and the transducer will affect the magnitude of thermal energy delivered to the treatment site. The region or mass of tissue to be treated can be part of an organ, part of a tumor, or part of some other anatomical structure. Preferably, the tissue is reasonably uniform, such that the thermal diffusivity of the tissue mass exhibits little variation throughout the tissue mass.

In a block 3, the empirical values determined in the calibration experiments are used along with the generic thermal model to calibrate the thermal model to the specific mass of tissue and the specific thermal source. In a block 4, the calibrated thermal model and ultrasound data collected during the calibration experiments are used to generate a temperature dependence curve unique to the specific mass of tissue and the specific thermal source. Note that blocks 2, 3, and 4 are encompassed in a block 8, because once the thermal model is calibrated and the temperature dependence curve is determined, the calibrated model and temperature dependence curve can be used for several different purposes. The calibrated thermal model/temperature dependence curve can be used to generate spatio-temporal temperature maps for pre-therapy planning and can also be used to calculate the time required for the thermal source to deliver a desired thermal dose to the mass of tissue, as indicated in an optional block 5.

In a block 6, the thermal source is used to deliver therapy to the mass of tissue, while ultrasound data are collected. The ultrasound data collected during therapy are used along with the calibrated temperature dependence curve to estimate the temperature of the mass of tissue while the therapy is in progress. In a block 7, the calibrated thermal model, the ultrasound data collected during therapy, and the thermal diffusivity (K) of the tissue mass are used to determine if the magnitude of the thermal source (Q') has changed. If so, the revised value for Q' is used to revise the temperature dependence curve. The revised temperature dependence curve can then be used to provide a more accurate temperature estimation during therapy, and/or to determine what effect the revised temperature dependence curve has on the time required to achieve the desired thermal dose.

FIG. 1B is a high-level flowchart schematically illustrating steps employed to perform the exemplary calibration experiment to estimate the thermal diffusivity (K) of the tissue mass. In a block 9, the thermal source is used to change the temperature of the tissue mass by a relatively small amount (i.e., a change of about 5° C. to about 15° C. relative to an ambient (pre-existing) temperature of the tissue mass), and ultrasound data are collected from the tissue mass while the tissue mass returns to its ambient temperature. In a block 10, the ultrasound data are used to estimate a spatial width of the temperature distribution as a function of time, to estimate the thermal diffusivity (K) of the tissue mass.

FIG. 1C is a high-level flowchart schematically illustrating exemplary steps employed to perform the calibration experiment configured to estimate the magnitude of the thermal source (Q'). In a block 12, the thermal source is used to change the temperature of the tissue mass to a predetermined value, while collecting ultrasound data from the tissue mass, and measuring the time required for the tissue mass to reach the predetermined temperature value. In a block 14, the thermal model, the measured time, the thermal diffusivity (K), and the ultrasound data collected while the thermal source was used to change the temperature of the tissue mass to the predetermined value are used to solve for the magnitude of the thermal source (Q'). As discussed below in greater detail, determining when the tissue mass has reached the predetermined value can be performed invasively or non-invasively. A temperature sensor can be invasively inserted into the tissue mass to enable the temperature of the tissue mass to be directly measured. In at least one exemplary embodiment, non-invasive techniques for determining when the tissue mass has reached the predetermined value are employed. The non-invasive techniques can be used if some phenomenon associated with the tissue mass reaching the predetermined temperature can be detected indirectly (i.e., without inserting a physical device into the tissue). If the predetermined temperature value corresponds to the boiling point of water, the onset of boiling in the tissue mass can be detected non-invasively using an acoustic sensor, such as a hydrophone, to listen for popping sounds, which can be detected when the boiling point has been reached. Alternatively, ultrasound imaging can be used to detect the onset of boiling, since a bright hyperechoic spot appears in the ultrasound image once the boiling point has been reached.

FIGS. 2A-2C graphically illustrate different types of temperature dependence curves. Note that portions 16a and 16b of the temperature dependence curves are relatively linear. However, portions 17 of the temperature dependence curves are not linear at all. While the concept of a temperature dependence curve is not new, what is newly disclosed herein is a technique for calibrating a temperature dependence curve for a specific mass of tissue and a specific thermal source, as well as techniques for calibrating the temperature dependence curve and thermal model using ultrasound data obtained non-invasively.

Note that FIG. 2A is a c(T) curve, showing an exemplary relationship between the speed of sound in tissue and the temperature of the tissue. FIG. 2B is a $\delta(T)$ curve, showing an exemplary relationship between the change in the speed of sound in tissue and temperature. FIG. 2C is a $\epsilon(T)$ curve, showing an exemplary relationship between strain (a concept described in greater detail below) and temperature. Any of these curves, once determined, can be used to estimate temperature. The type of data collected will determine which temperature dependence curve is most appropriate for estimating temperature. In an exemplary embodiment, discussed in detail below, the $\epsilon(T)$ curve is determined using RF data. In another exemplary embodiment, also discussed in detail below, the $\delta(T)$ curve is determined using RF data (essentially the same RF data can be used to determine the $\delta(T)$ curve and the $\epsilon(T)$ curve). In the claims that follow, it should be recognized that the term "temperature dependence curve" encompasses any type of tissue temperature curve discussed herein, including the c(T) curve, the $\delta(T)$ curve, and the $\epsilon(T)$ curve. Generally, c(T) curves are measured using transmission measurements (i.e., not backscattered RF data). Once RF data has been used to determine the $\delta(T)$ curve or the $\epsilon(T)$ curve, the other temperature curves (including c(T)) can be computationally derived.

FIG. 2D schematically illustrates an exemplary spatio-temporal temperature map 18 of a mass of tissue, where the thermal source is a HIFU transducer. A characteristic of HIFU transducers is that the thermal energy delivered by the HIFU transducer is concentrated at a relatively small, generally elliptical, focal point. As the therapy progresses, a temperature at an area T1 will be greater than a temperature at a larger area T2, which is greater than a temperature at a still larger area T3 (as the energy delivered to the focal point propagates outwardly into the tissue). With respect to HIFU therapy, a goal is to deliver sufficient thermal energy to target tissue so as to cause necrosis of undesired or unwanted tissue. The exemplary spatio-temporal temperature map enables temperatures at various locations within a mass of tissue to be estimated during HIFU therapy. HIFU therapy can be controlled so that whenever the temperature of a specific area corresponding to non-target tissue approaches necrotic levels, therapy can be discontinued to avoid damaging the non-target tissue. It should be recognized that spatio-temporal temperature maps are not new. The disclosure provided herein describes new techniques for non-invasively generating accurate spatio-temporal temperature maps. As discussed in greater detail below, such spatio-temporal temperature maps can be generated using a calibrated temperature dependence curve, to facilitate pre-therapy planning. Spatio-temporal temperature maps can also be generated in real-time during therapy, to enable temperature conditions in the tissue mass to be evaluated in real-time. Those of ordinary skill in the art will readily recognize that such spatio-temporal temperature maps can be readily overlaid over ultrasound images.

Exemplary Apparatus: FIG. 3A is a block diagram schematically illustrating the basic elements of a system 200 that includes a thermal source 202, an ultrasound imaging probe 204 (as well as a display for displaying ultrasound image data, and a processor for processing the ultrasound data to generate the ultrasound image, neither of which are separately shown), means 206 for determining when the tissue mass reaches the predetermined temperature, and a controller 208 (generally configured to implement the exemplary method steps of FIGS. 1A, 1B, and 1C, as described above). It should be recognized that controller 208 can be configured to process the ultrasound data to generate an ultrasound image, or a separate processor dedicated to generating ultrasound images can be employed.

FIG. 3B is a block diagram schematically illustrating the basic elements of a system 250 that includes a HIFU therapy transducer as the thermal source. System 250 includes a HIFU therapy probe 252 logically coupled with an ultrasound machine 258 (including a controller), a display 254 logically coupled with ultrasound machine 258, and a trigger 256 (enabling an operator to selectively energize the transducers in the therapy probe, or to engage a program stored in ultrasound machine 258 for controlling the therapy probe), is also logically coupled to ultrasound machine 258. It should be recognized that therapy probe 252 can be configured to be used internally or externally. While not separately shown, system 250 includes ultrasound transducers configured for imaging functions, as well as therapeutic functions. Those of ordinary skill in the art will readily recognize that system 250 can be configured to incorporate ultrasound imaging functionality in a variety of different ways. Some ultrasound transducers configured for HIFU therapy can also be used for imaging purposes, so long as the imaging and therapeutic pulses are properly synchronized. Thus, in some exemplary embodiments, therapy probe 252 incorporates transducers for ultrasound imaging, as well as for HIFU therapy. In other exemplary embodiments, therapy probe 252 includes one or more transducers specifically configured for HIFU therapy, and one or more additional transducers specifically configured for ultrasound imaging. In still other exemplary embodiments, separate therapy probes and imaging probes are used. The therapy and imaging transducers can be implemented on a single probe, such that the imaging plane associated with the imaging transducer is properly oriented with respect to the therapy transducer, and so that the region of tissue being treated by the transducer automatically lies within the imaging plane of the imaging transducer. If separate therapy and imaging probes are employed, care must be taken to ensure that the imaging probe is properly oriented with respect to the therapy probe, so that the tissue being treated by the therapy probe lies within the imaging plane of the imaging probe.

Significantly, the ultrasound machine is configured to utilize backscattered ultrasound collected during therapy and the calibrated thermal model/temperature dependence curve to estimate tissue temperature during therapy. The estimated tissue temperature can be output and presented to a user on display 254. In at least one exemplary embodiment, the estimated tissue temperature is integrated into an ultrasound image provided to the user on the display. In other exemplary embodiments, separate displays are employed to provide ultrasound images and temperature estimations to the user. It should be noted that means 206 sometimes requires input from an operator. Where means 206 comprises a thermal sensor, the sensor can be logically coupled to the controller to automatically indicate that the predetermined temperature has been reached. Where means 206 comprises an audio sensor configured to detect the popping sounds associated with boiling, the audio sensor can be logically coupled to the controller to automatically indicate when the predetermined temperature has been reached (the controller monitors the audio sensor to determine that an increase in an ambient sound level indicates the onset of boiling). In other exemplary embodiments, the audio sensor can be monitored by the operator, such that the operator actuates a trigger or other user input (such as a switch, a button, or a key on a keyboard or numeric keypad, where such elements are logically coupled to the controller) to indicate to the controller that the predetermined temperature value has been reached. Where means 206 corresponds to a bright hyperechoic spot in an ultrasound image, the operator will generally monitor the ultrasound image, and actuate such a trigger or switch to indicate to the controller that the predetermined temperature value has been reached. It should further be recognized that such user inputs can be considered to be part of the controller, where the controller is implemented using a computing device, as described below in greater detail.

FIG. 3C is a block diagram schematically illustrating the basic elements in a computing device that can be beneficially incorporated into the systems of FIGS. 3A and 3B. It should be recognized that the controller incorporated into ultrasound machine 258 can be implemented as hardware (such as an application-specific integrated circuit or ASIC), although generally, any computing device having a processor and a memory in which machine language instructions are stored and executed by the processor for controlling the process can also be employed as the controller. FIG. 3C and the following related discussion are intended to provide a brief, general description of a suitable computing environment, where the ultrasound machine incorporates a computing device.

Where a method or apparatus described herein requires means or elements for determining an empirical value for any of the parameters employed in the thermal models discussed herein, for calibrating a thermal model and determining a calibrated temperature dependence curve unique to a particular tissue mass and a particular thermal source, to use data collected during therapy and the calibrated temperature dependence curve to estimate tissue temperature during therapy, or to update the empirical value of the magnitude of the thermal source (Q') and use the updated empirical value to modify the temperature dependence curve during therapy (to increase an accuracy of the temperature estimations), it will be understood that such means or elements will typically require processing and manipulation of ultrasound data, which can be carried out using hardware (such as an ASIC, as discussed above) or a computing device, such as illustrated in FIG. 3C. In general, the processor can be incorporated into an ultrasound machine used in connection with the therapy probe. In some cases, a processor can be incorporated into a therapy probe; however, such an embodiment would likely undesirably increase the cost of the therapy probe. Since most ultrasound machines have processing capability, the required processing can normally be performed by the ultrasound machine. Furthermore, it should be recognized that if a particular ultrasound machine cannot be modified to perform the required processing, a separate computing device can be used for this purpose. Use of such a computing device does not represent much of a burden, since computing devices are now readily available and at relatively low cost.

An exemplary computing system 150, suitable for incorporation into the ultrasound machine (or use as a separate device), includes a processing unit 154 that is functionally coupled to an input device 152, and an output device 162, e.g., a display or monitor. Processing unit 154 can include a central processing unit (CPU 158) that executes machine instructions comprising a signal processing program for determining empirical values for parameters employed in the thermal model, defining a temperature dependence curve unique to the particular tissue mass and the particular thermal source, generating temperature estimates based on ultrasound data collected during therapy and the unique temperature dependence curve, and updating the magnitude of the thermal source parameter for the thermal model based on data collected during therapy, as generally described above. In at least one exemplary embodiment, the machine instructions implement all of these functions, although as noted above, the concept discussed herein also encompasses exemplary embodiments in which no updating of the parameters is performed during therapy. Additional signal processing can enable either an ultrasound image, a thermal map of the tissue, and/or some combination thereof to be displayed to a user. CPUs suitable for this purpose are available, for example, from Intel Corporation, AMD Corporation, Motorola Corporation, and from other sources, as will be know to those of ordinary skill in this art.

Also included in processing unit 154 are a random access memory (RAM) 156 and non-volatile memory 160, which typically includes read only memory (ROM) and some form of memory storage, such as a hard drive, an optical drive, a floppy drive, etc. These memory storage devices are bi-directionally coupled to CPU 158. Such memory storage devices are well known in the art. Machine instructions and data are temporarily loaded into RAM 156 from non-volatile memory 160. Also stored in memory are the operating system software and ancillary software. While not separately shown, it will be understood that a generally conventional power supply will be included to provide the electrical power needed to energize computing system 150.

Input device 152 can be any device or mechanism that facilitates user input into the operating system, and into application programs running under the operating system, including, but not limited to, a mouse or other pointing device, a keyboard, a microphone, a modem, or other device to receive and respond to a user input. In general, the input device will be used to initially configure computing system 150, to achieve the desired signal processing, and for input of control decisions by the user. While not specifically shown in FIG. 3C, it should be understood that computing system 150 is logically coupled to the therapy probe, display, and operator trigger of FIG. 3B. Configuration of computing system 150 to achieve the desired signal processing includes the steps of loading appropriate signal processing software (i.e., machine executable instructions) into non-volatile memory 160, and launching the signal processing application (i.e., loading the signal processing software into RAM 156) so that the signal processing application is ready for use. Output device 162 generally includes any device that produces output information, but will most typically comprise a monitor or computer display designed for human visual perception of output. Accordingly, a conventional computer keyboard and computer display used in connection with the computing device should be considered as exemplary, rather than as limiting on the scope of this embodiment.

Having discussed the exemplary techniques and apparatus in broad terms, a more detailed disclosure follows, beginning with a detailed description of the empirical apparatus employed to develop the concepts disclosed herein. The operation of the empirical system is discussed, along with a description of exemplary operating modes and exemplary performance specifications. The empirical system was used in all subsequently described experiments. Note that while the empirical system employs a HIFU transducer as a thermal source, it should be recognized that the concepts disclosed herein are not limited to temperature estimations of HIFU thermal sources, but other thermal sources as well.

Empirical Apparatus (the ATL HDI 1000™): It has been recognized that ultrasound data signal processing can greatly benefit from the ability to apply processing algorithms directly to beam-formed but otherwise unprocessed ultrasound backscatter data (commonly referred to as the "RF" data) that contain amplitude information, as well as phase information. FIG. 4 is a functional block diagram 20 representing an exemplary data signal flow in a receiver portion of an ultrasound scanner for the generation of B-mode image data (i.e., imaging ultrasound data). Backscatter ultrasound is collected by an imaging transducer 22 (acting as a receiver), and is directed to ultrasound machine 23. This signal is first processed using time gain compensation and analog-to-digital (A-D) conversion, as indicated by block 24. Raw RF data is then demodulated and decimated, as indicated by a block 26. Envelope detection and image processing are then performed, as indicated by a block 28, enabling a B-mode image 30 to be displayed. Note that after envelope detection and image processing, the signal data preserve amplitude data, as indicated by a block 34, but the instantaneous phase of the signal is discarded, as indicated by blocks 32 and 33. To facilitate differential signal processing techniques, it is desirable for the frames being compared to be acquired with a minimal inter-frame delay, to minimize de-correlation artifacts. Furthermore, it is also desirable to enable greater flexibility and control over data acquisition frame rates than is normally available for ultrasound imaging.

To achieve the signal processing required to implement the concepts disclosed herein, a commercially available ATL HDI 1000™ ultrasound machine (available from Philips Medical Systems, Bothell, Wash.) was modified to enable its software to do the required signal processing. The modifications enabled access to demodulated RF data (see block 33) at relatively high frame rates. Such data are useful for tracking the rapid yet subtle changes in tissue during thermal treatment. Custom modes of operation enabled trade-off of acquisition frame rate and lateral image widths, as described below. All of the algorithms described below were performed using this exemplary system on ultrasound data collected with the system during HIFU experiments.

The ATL HDI 1000™ diagnostic ultrasound scanner system, schematically illustrated in FIG. 5, was introduced commercially in 1997, and was one of the first ultrasound scanner systems implementing a dominantly software-based architecture. The ATL HDI 1000™'s beam-former includes 64 transmit and 32 physical receive channels 41, which can be multiplexed to provide 64/64 transmit/receive synthetic aperture acquisitions. The ATL HDI 1000™ can be used in synthetic aperture mode (64 channels) or in physical aperture mode (32 channels only). As indicated by a block 42, an analog Time Gain Control (TGC) is applied to each receive channel. An A-D converter samples the input on each channel (as indicated by a block 44) at four times the nominal center frequency ($f_o$), which is typically set to be close to the center frequency of the received echo signal, taking into account the effects of attenuation occurring along the imaging beam path. Digitization is performed with 8-bit precision. FIG. 5 indicates both the internal data path in a default mode 43, and in a custom-developed RF data access mode 45, employed to implement the temperature estimation and calibration methods disclosed herein. The digitized signal on each channel is then quadrature demodulated, as indicated by a block 46, to obtain base-band in-phase (I) and quadrature (q) data (note that Q is usually used to note quadrature data, but since Q has been used herein to denote the magnitude of thermal source, q is employed herein to denote quadrature data, to avoid confusion). The I and q data on the individual channels are delayed for dynamic focus, and summed to obtain base-band summed quadrature data, and the summed quadrature data are beam-formed along a particular scan-line. The focusing delays are applied to generate 32 channels each of I data 48a and q data 49a (each with 9-bit precision). Individual I and q data channels are then summed to obtain 16-bit beam-formed quadrature demodulated data (see I data 48b and q data 49b), which is routed, for example, either to ATL HDI 1000™ CPU RAM 52 or ATL HDI 1000™ hard disk 50, or to a signal processing function 54 and display function 56, depending on whether the default mode or the custom mode is selected.

In the default mode of operation, I and q channels are processed by signal processing block 54 to obtain B-mode, Color flow or Doppler data, depending on the acquisition mode selected by the user. When RF data access is desired, the summed quadrature base-band data follows the path indicated by dotted lines 58a and 58b. The data are temporarily stored in a pre-allocated memory block within volatile RAM on the system computer (e.g., on ATL HDI 1000™ CPU RAM 52). After the desired number of frames have been acquired and stored, the frames are copied as a binary file to hard disk 50, with additional fields containing information about the acquisition parameters necessary to interpret the RF data during offline processing. Since most of the system operation is controlled by software, modifications to meet data acquisition requirements for research purposes can be made relatively easily. In an exemplary implementation, RF data access was supported for standard echo imaging (i.e., the same transmitter configuration as for B-mode imaging), but modifications of the software to store RF data for Doppler and M-mode can be achieved with modest additional effort.

The maximum size of the memory block reserved in the ATL HDI 1000™ CPU RAM for storing the acquired frames temporarily is 75 MB. The memory block used in this device is based on a circular addressing scheme. Hence, once the entire memory block is full after a series of sequential frame writes, the address counter is reset, causing the buffer to wrap around, and any frames acquired thereafter replace those stored earlier, starting from the first in the current acquisition sequence. For a given set of acquisition parameters, the total number of frames that can be stored in the allocated memory block can be approximately calculated using the following formula, which takes into account the dependence of acquisition depth and frequency on frame size:

$$\text{Total number of frames } (N_{max}) = \frac{M \times k}{D \times f} \qquad (2)$$

where M=Allocated memory block (maximum 75 MB), D=Acquisition depth, f=Center Frequency of transducer, and k=scaling constant to be determined through a calibration test. For an acquisition depth of 4.5 cm with the ATL CL 10-5™ (available from Philips Medical Systems, Bothell, Wash.) linear scan-head, approximately 300 frames can be temporarily stored in the ATL HDI 1000™ CPU RAM.

The ATL HDI 1000™ system is based on a processor running a UNIX-like operating system (actually based on the Commodore Amiga computer operating system software). The software-dominant architecture on which the ATL HDI 1000™ is built allows for extensive external control of its operation, including front panel controlled acquisition parameters (imaging depth, focus positions, number of foci, TGC, etc). In addition, the start of RF frame acquisition can be initiated from an external source, with latency and jitter times on the order of a few milliseconds. Thus, RF data acquisition can be well synchronized with other instruments that are part of an experimental setup. Control commands from another computer can be issued via Telnet, and acquired RF data can be transferred via file transfer protocol (FTP) to another computing device for off-line processing. A software master control program using LabVIEW™ (available from National Instruments, Austin, Tex.) was employed to control the ATL HDI 1000™ system, as well as other devices and instruments. FIG. 6 shows a flow chart for the LabVIEW™ master control program, which can be configured to interleave HDI frame acquisitions with a variety of external events, such as robotic motion, therapeutic energy delivery, or other actuation and sensing functions.

Referring to FIG. 6, in a block 60 the ATL HDI 1000™ system is booted in the research mode. This configuration is selected at power-up time, using a floppy disk, to modify the boot sequence. Normal imaging operation, defined by the manufacturer, is the default startup mode (i.e., without the boot floppy disk), but insertion of a "research mode" boot floppy disk prior to startup forces a customized initialization based on special scripts residing on the floppy disk. The bulleted list on the right of the Figure summarizes the action of each block. This flexibility allows the ATL HDI 1000™ system to function both as a clinically approved ultrasound imaging scanner, and as a RF data acquisition system for research use. The scripts allocate a buffer in the ATL HDI 1000™ RAM (see FIG. 5), where acquired RF data frames are first stored, initialize directory paths and other acquisition control scripts for the research mode, and launch the Telnet communications program, as indicated in a block 62. The master control program, running on an external computing device (e.g., a computing device functionally similar to that shown in FIG. 3C), which is connected to the ATL HDI 1000™ via a network connection, then takes over imaging system operation. Specific acquisition settings for the current experiment are sent to the ATL HDI 1000™. In the simplest data acquisition mode, the control program periodically sends very brief commands to initiate each frame acquisition, based on user-specified settings for total number of frames to be acquired (N) and the desired frame rate, as indicated in blocks 64*a* and 64*b*. Each acquired frame is stored in contiguous blocks in the ATL HDI 1000™ RAM. Once the entire frame acquisition sequence is complete, in response to a final control command, the set of frames residing in RAM are transferred to the ATL HDI computer's hard disk and are stored as a binary data file, as indicated in a block 66. Then, the data file is transferred to the external computer via the network connection, as indicated in a block 68. The master control sequence used to simultaneously control the HIFU signal generation circuitry is described below.

The performance of algorithms used for motion and velocity estimation are greatly improved by acquiring data at high frame rates. In addition, high frame rate data acquisition allows speckle noise to be reduced, by employing temporal averaging, without compromising temporal resolution. Typically, there is a trade-off between the number of scan lines per frame (the default in this exemplary system is maximum of 128 scan lines, corresponding to a lateral width of 2.5 cm for the CL10-5™ compact linear probe, which is available from Philips Medical Systems, Bothell, Wash.) and the frame rate (the latter also depends on the maximum depth of the image). Two data acquisition schemes for increasing the frame rate, using a reduced number of scan lines per frame, have been empirically implemented. These schemes are referred to as: (1) reduced sector width mode; and, (2) sparse scan-line mode. Considerable improvements in frame rate are achieved in each of these modes, by controlling the beam-former firing sequence, to capture only the desired number of lines, thus reducing the amount of data processing within the system.

In reduced sector width mode, a contiguous subset of the 128 lines making up the complete image is used to form a narrower 2-D image. FIG. 7A is a monochromatic image based on a B-mode image of the carotid artery reconstructed from the RF signals collected for a full lateral width of 2.5 cm (default). FIG. 7B is a monochromatic image based on a B-mode image of the carotid artery reconstructed from the RF signals collected for a reduced sector width mode scan, with lateral width set to 0.6 cm (32 scan lines). Both images were acquired using the compact linear probe (CL10-5™) and ATL HDI 1000™. For the CL10-5™ probe, the nominal center frequency ($f_0$) is 6.15 MHz, and the sampling rate is 24.6 MHz (4 times $f_0$).

FIG. 7C graphically illustrates the frame rates obtained in the default mode with a full sector width (128 scan lines), and in the reduced sector width mode (lateral width of 0.6 cm and 1.25 cm), for an acquisition depth of 2.2, 4.5, and 8.2 cm, using the CL10-5™ scan-head. Corresponding to the axial depths of 2.2, 4.5, and 8.2 cm, there are 176, 360 and 656 I/q data points per scan-line, respectively. The lateral widths of 0.6, 1.25, and 2.5 cm correspond to 32, 64, and 128 contiguous scan-lines, respectively. The frame rate is essentially inversely proportional to the lateral image width. This mode of operation is useful when data acquisition at high frame rates is desired, and the lateral field of view can acceptably be compromised.

In the sparse scan-line mode, the total lateral field of view is the same as for the default mode. However, a sparse subset of the total 128 scan-lines is used to acquire the frame, with inter-scan-line spacing set to 2, 4, or 8 line widths. FIG. 8A is a monochromatic image based on a B-mode image of the carotid artery (the same region shown in FIG. 7A), obtained using a default scan-line spacing of 1 (i.e., all 128 scan-lines active). FIG. 8B is a monochromatic image based on a reconstructed B-mode image with the system setup for sparse scan-line mode acquisition, with an inter-scan-line spacing of 4. This sparse scan-line mode is well-suited for applications in which high frame rates are desired with full sector width, and a decrease in lateral resolution is acceptable. FIG. 8C graphically illustrates the frame rates obtained in the default mode (128 scan lines) and the sparse scan-line mode for an acquisition depth of 2.2, 4.5, and 8.2 cm. A line spacing of 1 represents the default acquisition mode with 128 scan-lines. The inter-scan-line spacing of 2, 4, and 8, correspond to 64, 32, and 16 scan-lines of data, respectively.

While the concepts presented herein can be used to non-invasively estimate tissue temperature using ultrasound during thermal therapy implemented using a wide variety of heat sources, as noted above, HIFU therapy represents a particularly useful type of thermal based therapy. One of the important requirements of an ultrasound RF data acquisition system for use in HIFU therapy monitoring is proper synchronization between HIFU therapy ON times and RF data acquisition, since interference between the HIFU beam and the imaging system would otherwise degrade the RF data quality significantly. A monochromatic version of a B-mode image reconstructed from the RF data acquired during HIFU is shown in FIG. 9, dramatically illustrating how overwhelming HIFU interference can be when imaging and HIFU are not properly synchronized. This interference occurs due to saturation of the receiver electronics in the front end of the imaging scanner by the HIFU. This problem can be minimized by triggering a gate signal on the HIFU therapy control unit with the excitation pulse of one of the elements of the imaging probe. As a result, the HIFU interference pattern is relegated to a section of the image frame outside the zone of lesion formation (that is, the interference can be shifted to a portion of the image away from the area in which the thermal lesion is forming, such as an edge of the image). However, this setup does not support simultaneous RF data acquisition, which is desirable for off-line algorithm development. The modifications to the ATL HDI 1000™ ultrasound scanner (i.e., the master control program written in LabVIEW™), makes interleaving RF data acquisition with HIFU therapy delivery straightforward. Moreover, integrated control of therapy delivery and imaging from the same master controller (i.e., the remote computer implementing the master control program written in LabVIEW™) ensures proper synchronization, which is essential for quantitative imaging applications. A detailed description of such synchronization is presented below.

The RF data acquisition system based on the modified HDI 1000™ was first tested during an in vitro experiment to study the formation of HIFU-induced lesions in bovine liver tissue. The schematic diagram for the in vitro experiments is presented in FIG. 10A. An external computer 70 running the master control software program sends control signals 72 to HIFU signal generation circuitry 74 (HP-33120 function generator, available from Hewlett Packard, Palo Alto, Calif.) via GPIB, and to an ATL HDI 1000™ ultrasound system 76 via a Telnet connection 78. The control sequence begins with a software command sent by the program to turn on the HIFU source (power amplifier 80 and HIFU transducer 82). After a programmable ON-time has elapsed (50 ms-200 ms), the HIFU is turned off (via GPIB), and a command dispatched to the ATL HDI 1000™ to acquire an RF frame using imaging probe 84, while the HIFU is off. Note that imaging probe 84 is aligned such that it scans along a longitudinal axis of a therapy beam 86 in a plane with a HIFU lesion 88 forming in tissue 90. The software program then waits for 100 ms (programmable) for the ATL HDI 1000™ to complete acquisition (transmit-receive-store) before turning the HIFU on again for another exposure-image cycle. The above sequence is repeated with the master program alternating or interleaving HIFU pulses with RF data frame acquisitions. An exemplary timing diagram representing this synchronization scheme is illustrated in FIG. 10B. Note that ultrasound image data are obtained only when the HIFU is off. The total therapy delivery time was 2 seconds, while post-therapy acquisition of RF data frames continued for an additional 40 seconds, in this example.

A compact linear scan-head (CL 10-5™, available from Philips Medical Systems, Bothell, Wash.) was used for imaging, along with a single PZT element HIFU transducer (Model SU107, available from Sonic Concepts, Woodinville, Wash.), nominally operating at 3.5 MHz, with an aperture diameter of 33 mm, and a focal depth (radius of curvature) of 35 mm. The ATL HDI 1000™ was set to acquire the full lateral width of 2.5 cm (128 scan-lines). As shown in FIG. 10A, the HIFU transducer was driven by a power amplifier (A150™, available from ENI, Rochester, N.Y.), connected to a signal generator emitting a gated sine wave. In this arrangement, the frame rate of the ATL HDI 1000™ is about 10 fps, but the HIFU duty cycle was chosen to be 66% (200 ms ON, 100 ms OFF), and the ATL HDI 1000™ is in a frozen state between frame acquisitions. No HIFU interference is observed in the RF data; indeed, the actual ultrasound acquisition time is significantly shorter than the 100 ms allotted. The timing parameters shown in FIG. 10B were used for an in vitro HIFU experiment (HIFU ON: 200 ms, RF acquisition: 100 ms). Note that although actual frame acquisition lasts only about 30 ms, additional delay is incorporated to account for internal data transfer and system latencies.

The results of these initial HIFU experiments, shown in the B-mode images of FIG. 11A-11C, indicate that hyperechogenic regions forming in the neighborhood of the HIFU beam focal zone can appear (and disappear) very rapidly, and aside from a subtle scintillation of the speckle pattern in the focal zone prior to the echogenicity, little change to the image is visible. Conversely, processing of the full wave signal (RF) indicate that progressive changes in the speed of sound of the medium, and in scattering characteristics of the tissue, are almost immediately detectable upon initiation of HIFU exposure, well before a lesion is formed. Differential processing of backscattered RF ultrasound can thus provide quantitative measures of lesion evolution, and forms the basis for many of the concepts disclosed herein.

As noted above, a software-based system was employed to synchronize the RF data acquisition with the HIFU therapy delivery. To quantify the software timing latency between issuing a control command from the master control program and observing the instrument response, a timing analysis was performed. Specifically, the latency in the frame acquisition after a control command has been issued from the PC was experimentally measured. The ATL HDI 1000™ ultrasound scanner was controlled over the Telnet port from the master-controller PC. At the same instant that a software control command to initiate RF frame acquisition was sent to the ultrasound scanner, a TTL high signal (+5 V) was output on the parallel port of the PC, and recorded on the oscilloscope on Channel 1. After a brief delay (about 5 ms), the TTL pulse was set low. The transmit pulse recorded by a needle hydrophone placed at the focus of the imaging transducer (indicated by the focus markers on the B-mode image) along the edge of the first scan-line was recorded on Channel 2. The time delay between the signals recorded on Channel 1 and 2 was measured to obtain an estimate of the system latency. The measured latency was approximately 17 ms. This value includes the internal PC latency in sending the control command over the Telnet port, delays along the Telnet link, and the system delay internally within the ATL HDI 1000™ associated with parsing the Telnet command, activating the beamformer, and initiating frame acquisition.

Although an exemplary application for this system is used for acquisition of RF data during HIFU experiments, the system can easily be adapted to meet the data acquisition needs for other emerging ultrasound imaging modalities requiring access to RF data, such as elastography.

A tissue-mimicking phantom with an inclusion loaded with scatterers (7% polyacrylamide was used for the background and 15% for the inclusion, making it stiffer) was subjected to external compression in the axial direction in steps of 0.1 mm using a mechanical fixture for holding the imaging probe (L11-5™, available from Philips Medical Systems, Bothell, Wash.) attached to a 1-D motion stage. The Young's modulus of the background and inclusion were measured using a mechanical indenter and were determined to be 16.3 kN/m² and 33.4 kN/m, respectively. A schematic representation of the experimental setup for this determination is shown in FIG. 12. As indicated in the Figure, an external compression is applied in the axial direction, using a mechanical fixture mounted on a 1-D motion stage. Motion of the phantom is limited to the axial and lateral direction, with constraints applied to prevent motion in the elevation direction. Movement of the motion stage and RF data acquisition using the ATL HDI 1000™ is controlled from the PC running the LabVIEW™-based master control program.

The software program for temperature estimation and thermal modeling was modified for use in this application to control the movement of the motion stage and to initiate acquisition of RF data frames, essentially replacing the HIFU system with the mechanical compression system. The acquisition sequence begins with a command sent to the ATL HDI 1000™ to acquire an RF data frame (via Telnet). After the frame has been acquired, a command is dispatched to the motion stage (via an ISA bus interface) to move the transducer to compress the phantom by 0.1 mm (out of a total phantom height of about 9 cm). The above sequence was repeated until the phantom was compressed by the desired total displacement of 10 mm, and RF data frames were collected between each displacement step, resulting in a total of 100 RF data frames. This data set permitted exploration of various algorithms and parameter choices for determining strain, and assessing the noise in the system.

FIGS. 13A-13C illustrate typical results for this type of test. The RF lines were divided into overlapping segments, and the axial displacement between segments at the same lateral position selected from frames ten time steps apart was computed using a 1-D cross-correlation algorithm. A least-squares strain estimator was used to compute the axial strain from the displacement estimates. FIG. 13A shows the B-mode image of the phantom with the external compression applied at the top of the image. By design, there is little echo contrast between the background and the inclusion. The axial displacement map is shown in FIG. 13B, and the strain elastogram appears in FIG. 13C. The region surrounding the inclusion is delineated with a dotted line on the B-mode image. Visible contrast between the background and the inclusion is seen on the strain elastogram. The acrylamide gel phantom was subject to 0.1 mm axial compression per step from the top, using an external compressor. Lighter shades (towards white) on the color tonal scale represent low relative strain, while darker shades towards black (bottom) represent higher relative strain. The total displacement resulting from the external compression was 10 mm. An estimate of the error in the displacement determination was also obtained using a "sham" measurement in which no external motion was applied. A set of 10 RF frames was acquired with no external compression, and the 1-D displacement tracking algorithm was used to estimate the axial displacement. The mean displacement error over the entire frame was 0.4 μm. The theoretical lower bound on the error in determining the displacement was about 0.25 μm.

To determine the suitability of the ATL HDI 1000™ for freehand elastography, it was assumed that choosing a minimum displacement (external compression) of five times the displacement error would provide a reasonable signal-to-noise ratio. Thus, at least 2 μm compression between frames would be desirable. Assuming a freehand acquisition frame rate of 10 frames per second, a compression rate of at least 20 μm/s would be adequate. However, to avoid speckle de-correlation as a result of large external strains, it is desirable to limit the maximum applied external compression rate to less than 10 mm/s. Consequently, freehand elasticity imaging for externally applied compressions in the range 20 μm/s to 10 mm/s on simple objects should be feasible using this exemplary system. In vivo elasticity imaging is typically much more difficult, but the results of the phantom test indicate that the ATL HDI 1000™ system is a promising tool for freehand elastographic data acquisition.

Model for Temperature and Ultrasound Backscatter: A mathematical model defining the relationship between temperature and ultrasound backscatter related to changes in speed of sound and thermal expansion is described next, along with signal processing-based algorithms designed to extract information from the ultrasound backscatter related to change in tissue properties associated with therapy. Results obtained by applying these non-invasive techniques to in vitro tissue-mimicking phantoms and in animal tissue experiments are also discussed below.

A significant milestone in developing the techniques disclosed herein was the recognition that tracking changes in the raw ultrasound backscatter (commonly referred to as "ultrasound RF") provide improved visualization of lesion formation induced by HIFU, compared to standard fundamental ultrasound B-mode images. Two signal processing approaches to track changes in the ultrasound backscatter were applied, including one designed to track temperature related information, and the other designed to detect changes in local tissue scattering properties.

When a region of tissue is heated, the backscattered ultrasound signal experiences echo location shifts. These shifts are due to changes in the effective location of the scatterers due to changes in the local speed of sound and thermal expansion. The change in the local speed of sound causes an apparent shift in the scatterer location, while the thermal expansion effect causes a physical shift. FIGS. 14A-14D schematically illustrate the change in the echo locations due to scatterer location shifts caused by local changes in temperature along the ultrasound pulse propagation path, where c is the nominal speed of sound assumed in the imaging system. The total shift in the echo at a particular depth is the cumulative sum of the local travel time changes occurring at shallower depths. FIG. 14A represents the scatterer locations along the pulse propagation path at temperature $T_0$. FIG. 14B shows the scatterer locations when the local temperature changes to $T_0$, $T_1$, and $T_n$, respectively. FIGS. 14C and 14D represent the backscattered echo corresponding to the scatterer locations shown in FIGS. 14A and 14B, respectively. The individual scatterers move a distance ($\Delta d_i$) due to a temperature change $T_i$ (FIG. 14B). The corresponding change in the round trip travel time of the ultrasound pulse to the scatterer, referred to as the local acoustic travel time change, is then given by $\Delta t_i = 2\Delta d_i/c$, where the factor 2 is due to the round trip travel, and c represents the nominal speed of sound in the medium. These local acoustic travel time changes result in cumulative shifts in the backscattered echo (FIG. 14D). The echo shift at a given depth ($\Delta t_1$, $\Delta t_1 + \Delta t_2$, $\Delta t_1 + \Delta t_2 + \ldots + \Delta t_n$ for the scatterers shown) is thus cumulative. This cumulative shift is observed in the backscattered echo signal. To compute the local acoustic travel time change (i.e., $\delta(T)$), the derivative along the depth direction is computed.

Experimentally measured speed of sound versus temperature (c(T)) curves, which are typically represented by a second order polynomial for water-based tissue media, have been reported. Specific trends can be noted in the c(T) curve for biological tissue with low fat content. Typically, for temperatures near body temperature, the speed of sound increases rapidly with temperature. The speed of sound commonly peaks at temperatures between 50 and 70 degrees C., depending on tissue type, and then decreases with further increase in temperature. FIG. 15 graphically illustrates the c(T) data for ex-vivo pork liver over the therapeutic range, fitted by a second order polynomial, with the error bars representing variation in estimates from different samples. Data for the thermal expansion coefficient (expressed in/° C.) in soft tissue is available for a limited temperature range up to 50° C. In this temperature range, it has been shown that the time shifts caused by thermal expansion are significantly less than that due to the local speed of sound changes. From FIG. 15, it can be seen that the sensitivity of the speed of sound versus temperature relationship decreases as the temperature is raised from room temperature close to the coagulation threshold, and this complicates the direct mapping of observed speed of sound changes to temperature. Thus, one aspect of the concepts disclosed herein is directed to methods for extracting the echo shifts from the ultrasound backscatter during HIFU exposures. Mapping of this information to temperature is described in the following section.

In the mathematical formalism relating the echo shifts observed on the backscattered ultrasound signals to temperature change, the model employed assumes that the effect of thermal expansion is negligible, that the relationship between speed of sound and temperature is spatially invariant, and that the initial baseline temperature is constant throughout the medium before heating commences. Note the relationship between temperature and the local acoustic travel time change (due to the speed of sound change, i.e., $\delta(T)$), is explicitly derived. The mapping between speed of sound change and temperature is assumed to be linear in this analysis.

Consider a 2-D arrangement of discrete acoustic scatterers. The sound propagates through the medium along y and x in the direction of scanning. The received echo signal is spatially sampled with a spacing $\Delta y$. The ultrasound imaging transducer that sends out the sound pulses and detects the echoes is located at y=0. The analysis below is for a fixed location x, without any loss of generality. For a uniform speed of sound at the baseline temperature of $T_0$ ° C., $c_0$, the round-trip travel time, $t_i$, to the $i^{th}$ element in depth, is:

$$t_i = \frac{2i\Delta y}{c_0} \quad (3)$$

The new round-trip travel time to a depth location l due to the temperature induced change in speed of sound is:

$$t'_k = \sum_{i=0}^{i=k} \frac{2\Delta y}{c_i} \quad (4)$$

where $c_k$ is the speed of sound value for the kth sample volume in the intervening acoustic path between the transducer and the region of tissue under consideration. Therefore, the travel time change ($\delta t_i$) of the ith tissue sample volume in the heated tissue relative to the unheated tissue is:

$$\delta t_i = t'_i - t_i = 2\Delta y \left[ \sum_{k=0}^{k=i} \frac{1}{c_k} - \frac{i}{c_0} \right] \quad (5)$$

For an imaging system that displays echo information, assuming that distance is linearly related to propagation time via an assumed uniform speed of sound, $c_{system}$, the travel time change due to local changes in speed of sound manifests as an apparent echo shift in the backscattered signal, given by:

$$\delta y_i = \frac{c_0 \delta t_i}{2} = t'_i - t_i = c_{system} \Delta y \left[ \sum_{k=0}^{k=i} \frac{1}{c_k} - \frac{i}{c_0} \right] \quad (6)$$

Eq. (6) illustrates how changes in the local speed of sound of the medium caused by local temperature rise results in shifts in the echo location in the backscattered ultrasound signal. It may be noted from Eq. (6) that merely tracking the echo shift ($\delta y_i$) does not provide unique information related to the local speed of sound change. In order to extract local changes in speed of sound that could be directly related to local change in temperature, the derivative along the depth direction must be computed. The simplest approach is to assume that the size of the 1-D window used in least squares strain estimation is 2 samples, which would be equivalent to calculating strain using the finite difference technique. Thus, from Eq. (6), the temperature induced strain $\epsilon_i$ of the $i^{th}$ pixel in the displacement image is given by:

$$\varepsilon_i = \frac{\delta y_{i+1} - \delta y_i}{\Delta y} = c_{system}\left(\frac{1}{c_{i+1}} - \frac{1}{c_0}\right) \quad (7)$$

The speed of sound $\epsilon_i$ can be expressed in terms of the change in speed of sound relative to $c_0$ as:

$$c_{i+1} = c_0 + \delta c_{i+1} \quad (8)$$

Since $\delta c_{i+1} \ll c_0$, Eq. (7) becomes:

$$\varepsilon_{i+1} = c_{system}\left(\frac{\delta c_{i+1}}{c_0^2}\right) \quad (9)$$

For a linear change in speed of sound as a function of temperature (valid in the range from room temperature to about 50° C.), the speed of sound ($c_T$) at temperature T at any spatial location can be expressed in terms of the initial speed of sound $c_0$ as:

$$\delta c = c_T - c_0 = \beta \delta T \quad (10)$$

where $\delta$ is the temperature coefficient for speed of sound, and $\delta T$ is the change in temperature relative to the initial temperature $T_0$.

Combining Eqs. (9) and (10), it can be seen that the temperature induced strain ($\epsilon$) is directly proportional to the induced temperature change:

$$\varepsilon_{i+1} = c_{system}\left(\frac{\beta \delta T_{i+1}}{c_0^2}\right) \quad (11)$$

The constants $c_{system}$, $\beta$, and $c_0$ are combined together to form a new scalar constant $\gamma$. Eq. (11) can thus be rewritten as:

$$\epsilon_{i+1} = \gamma \delta T_{i+1} \quad (12)$$

Eq. (12) shows that to convert the temperature induced strain values computed from the backscatter data to quantitative temperature change, accurate knowledge of the scalar constant $\gamma$ is required. This quantity, however, is highly tissue dependent, since it depends on the relative proportion of tissue constituents such as fat, collagen, and water. If accurate knowledge of this parameter is available, the strain estimates derived by processing the ultrasound backscatter can be mapped to temperature.

To estimate the echo shifts and temperature induced strain ($\epsilon$) from backscattered ultrasound data collected during HIFU therapy, a time domain cross-correlation based algorithm was developed. The algorithm operates on pairs of RF data frames acquired sequentially during the HIFU exposure experiment. The organization of the RF data set collected using the ATL HDI 1000™ ultrasound scanner is illustrated in FIGS. 16A and 16B, with FIG. 16A illustrating the orientation of the imaging transducer and the image acquisition plane, and FIG. 16B illustrating the organization of the RF data set. A block diagram representation of the processing scheme is shown in FIG. 16C. The computations are performed over segments selected along the axial direction at a single lateral location on two adjacent frames, and repeated for each column along the lateral direction, for a pair of RF frames i and i+1 that are collected at an experiment times (slow time) t and t+$\Delta$T. For a given segment, this operation can be mathematically represented by the following equation:

$$c(j) = \max_{j} \sum_{k=0}^{k=m-1} s_i(k) s_{i+1}(k+j) \quad -n/2 < j < n/2 \quad (13)$$

where $s_i$ represents a RF segment on line i, $s_{i+1}$ represents a RF line segment on line i+1, j represents the time shift between $s_i$ and $s_{i+1}$, m represents the window length, n represents the search range on line i+1 and c represents the cross-correlation coefficient. The segments $s_{i+1}$ and $s_i$ are normalized to unit energy. In this case, c represents the normalized cross-correlation coefficient, with values ranging from −1 to 1.

The RF lines (typically 128 in number) in each frame are divided into a series of segments of 1 mm in length with a 20% overlap. For each segment in a given frame (i), a search region is defined around the same spatial location on a temporally adjacent frame (i+1). The segment selected in frame i (say $s_i$) is multiplied by a window at the top of the search region ($s_{i+1}$) in frame i+1 point-by-point, summed, and the value stored as a variable c. This operation is repeated until the end of the search region is reached, keeping $s_i$ the same but choosing a new segment $s_{i+1}$ in each iteration, each iteration beginning one sample below the previous choice of $s_{i+1}$. The time shift j between $s_i$ and the window choice $s_{i+1}$ that maximizes c is the estimated shift, and j is converted to seconds by multiplying by the RF sampling period, to obtain travel time change between adjacent frames, $\delta t_{adjacent}$. This operation is repeated for all the overlapping segments defined in frame i to generate a $\delta t_{adjacent}$, 2-D matrix corresponding to frame $s_i$ and is then repeated for all of the frames, taking 2 frames at a time and computing a $\delta t_{adjacent}$ matrix for each set of frames. A 3-D matrix of $\delta t_{adjacent}$ of size N−1 (where N is the total number of acquired RF data frames) is thus obtained. A cumulative sum of the time shifts ($\delta t_{adjacent}$) is computed along the temporal direction (slow time) to obtain the cumulative travel time change map ($\delta t$) that represents the time shift change with reference to the initial frame before therapy commenced (i.e., before the ultrasound data are acquired). Computing $\delta t_{adjacent}$ between adjacent frames and then summing these results to obtain the cumulative change has been shown to reduce errors due to de-correlation. These estimates of $\delta t$ are an integrated quantity in that travel time changes detected at a particular depth are influenced by changes along the acoustic path shallower than that depth. Thus, to obtain the estimates of local travel time change, $\delta t$ is differentiated axially to obtain a map of $\epsilon$. The differentiation is performed by fitting a straight line on the $\delta t$ estimates over a length of 4 mm. The slope of the fitted line gives $\epsilon$ locally.

The magnitude of the time-shifts $\delta t_{adjacent}$ is typically very small. It varies from $1/10^{th}$ of the RF data sampling interval to a few samples, which necessitates employing accurate sub-sample estimators that are capable of estimating time shifts equal to a fraction of an RF sampling period, to obtain the desired accuracy. The sub-sample estimator employed in this algorithm is based on a parabolic interpolation technique. The peak of the interpolation function is fitted to a parabola, and the maximum point on the parabola is estimated. This approach enables time-shifts less than a RF sampling period to be estimated. The parabolic interpolation technique does result in biased estimates, depending on the true value of the time shift, and the bias error function has a characteristic shape of a sine function. The maximum sub-sample estimate error occurs at time shifts 0.25-0.3 samples away from integer shifts, while zero bias error occurs at a time shift of 0.5 samples.

In vitro experiments were performed in a bovine liver and in tissue-mimicking phantoms to demonstrate that temperature-related changes during HIFU therapy can be visualized by tracking the temperature induced strain ($\epsilon$) measured from the ultrasound backscatter data. Details of these experiments and the results obtained are provided below.

Experimental Therapy Protocols: Two clinically applicable experimental therapy protocols were employed. In the first protocol, point lesions were created by holding the HIFU transducer stationary while therapy was being delivered. The typical size of the lesion in this case was close to the physical dimensions of the focus of the HIFU therapy transducer employed in the tests (e.g., 5 mm along the HIFU beam propagation path, and 0.5 mm transverse to that path). The second experimental protocol is referred to as the scanned lesion protocol. In this approach, the therapy transducer was translated along the circumference of a circle of a radius of 7.5 mm, while emitting the acoustic beam at a fixed intensity. The lesion extends over the entire circumference of the circle. These protocols require synchronization between HIFU therapy delivery, the ATL HDI 1000™ and the transducer scanning to ensure that HIFU interference-free RF data are obtained.

The experimental setup of FIG. 10A was employed. A 3.5 MHz HIFU therapy transducer (SU-107™, available from Sonic Concepts, Woodinville, Wash.) with an aperture diameter of 33 mm, and a focal depth of 35 mm, was utilized for delivering the HIFU therapy dose. The therapy transducer included an air-backed, concave, single PZT element. The driving electronics for the HIFU transducer utilized a signal generator (HP 33120™, available from Hewlett Packard, Palo Alto, Calif.) driving a power amplifier (A300™, available from ENI, Rochester, N.Y.). The imaging probe was the ATL CL10-5™ (available from Philips Medical Systems, Bothell, Wash.) with a frequency range of 5 MHz to 10 MHz. RF data frames were acquired between HIFU exposures, at a rate of about 5 Hz, with the HIFU completely off during the acquisition to avoid interference from the HIFU beam. The RF data acquisition was controlled as described above. Alignment needles mounted at the base of the sample holders were used to ensure that the imaging plane of the ultrasound scanner coincided with the plane of HIFU beam propagation. As part of the experiment setup, before the therapy session commenced, the HIFU transducer was first translated in a 3-D plane until the reflected signal from the near end alignment needle received using a pulse-echo technique was maximized. This approach ensured that the focus of the HIFU transducer was aligned with the needle. The ultrasound imaging probe was mounted on a specially-designed fixture attached to the sample holder, so that the imaging plane also coincided with the needles. This alignment was confirmed by ensuring that the needles were visible on the B-mode images. The RF data collected were transferred to the PC at the end of the experiment, for offline processing.

Fresh whole beef liver was obtained on the day of the experiment and chilled in phosphate buffered saline (PBS) solution. Pieces of liver were carefully cut to select nearly homogenous tissue by avoiding large blood vessels. The pieces were sized to fill specially-designed tissue holders that enable the imaging and therapy transducers to be registered to the tissue block, and oriented such that the longitudinal axis of the therapy beam was in the plane of the imaging probe and perpendicular to it. The liver samples were degassed in PBS, and warmed to 37° C. in a water tank filled with degassed PBS. The in situ therapeutic intensity ($I_{SAL}$) used was calculated to be 1250 W/cm$^2$, based on measurements made in water using a radiation force balance, and assuming an attenuation coefficient of 0.7 dB/cm/MHz for liver. For the results presented in this section, the total integrated HIFU exposure time was 2 seconds. The intensity and duration of exposure to HIFU were determined based on comprehensive dosimetry studies conducted in-house to observe the bioeffects under well controlled conditions for a range of experimental parameters. RF frames (each RF frame being a collection of A-lines over a lateral extent of 2.5 cm and with a lateral spacing of ~0.2 mm) were collected every 0.2 s during a 0.1 s interruption of HIFU delivery. A single frame was acquired before HIFU therapy commenced to serve as the reference frame. After HIFU exposure, RF data frames were acquired at intervals of 10 seconds for 2 minutes to visualize the cool down period.

FIG. 17 is a composite image schematically illustrating the bovine liver experiment and the results. Travel time change maps are expressed as apparent displacement in microns in the middle row. Temperature induced strain maps for the in vitro bovine liver experiment are provided in the bottom row. The top row shows the corresponding B-mode images recorded at different time intervals during the experiment. In the middle row, the travel time change maps ($\delta t_{adjent}$) are scaled by a nominal value of 1540 m/sec (speed of sound assumed on the ATL HDI 1000™) and are represented as apparent displacements in microns. The HIFU transducer is to the left and the imaging probe is disposed at the top of the images. The timer represents the temporal location of the current frame with respect to the first frame acquired before HIFU therapy commenced. The grey scale (the actual results were displayed in color) is bi-polar, where apparent displacement towards and away from the imaging transducer is presented in shades of grey (red and blue, respectively, in the original image). The displacement maps are further modulated by the correlation coefficient (c in Eq. (13)) between RF segments used in the displacement estimation, with lighter shades of gray representing estimates with lower confidence.

These results indicate that very soon after the HIFU was turned on (0<t<0.4 seconds), apparent motion towards the imaging transducer (located at the top of image) is observed over a large region surrounding the focal zone, and such apparent motion appears before any hyper-echogenicity develops on the B-mode image. This result is related to the rapid increase in temperature in the focal region, which causes a decrease in acoustic travel time. Similarly, during the cool-down period (after t=2.2 seconds), apparent motion appears in the opposite direction, due to recovery of speed of sound values. In the time interval 1.8<t<2.2 seconds, a hyper-echogenic spot is seen on the B-mode image, while in the corresponding apparent displacement image, the area around the focal spot is delineated by an oval zone with colors indicating maximum positive and negative apparent motions in a random pattern, largely masked by the gray color. This result is most likely due to the rapid generation of bubbles producing de-correlation of the RF data. The bottom row in FIG. 17 shows the temperature induced strain ($\epsilon$) profiles during HIFU therapy delivery, one acquired shortly after HIFU commenced (t=0.2 seconds) and the other at t=2 seconds, when a hyperechoic spot appears on the B-mode image. Strain change related to the temperature increase at the focal spot can be clearly seen. The de-correlation in the RF data possibly due to the formation of bubbles also affects the $\epsilon$ maps in a manner similar to the $\delta t$ maps, as seen from the maps at time t=2 seconds.

The point lesion bovine liver experiment demonstrated that estimates of temperature induced strain ($\delta t$) computed from the RF data provides useful information for tracking the temperature rise during HIFU therapy. In addition, on a qualitative basis, since changes were seen on the maps before appreciable changes occurred on B-mode images, they provide a method of improved visualization of the lesion location and in guiding the therapy beam.

The scanned lesion protocol was employed because in clinical applications, the volume of tissue being treated is increased by scanning the focal point through a volume of tissue. In the scanned lesion experiments, temperature induced strain ($\epsilon$) maps were generated using the algorithm described above, using data collected during scanning of the HIFU focal point. Changes were made to the master control program so that the HIFU transducer attached to a 3-D motion stage could be translated along a circle during the experiment. The imaging transducer was oriented perpendicular to the HIFU beam propagation axis. The relative orientation of the HIFU transducer, imaging transducer, and the plane of lesion formation is illustrated in FIG. 18. The imaging transducer was oriented such that the imaging plane coincided with the plane in which the lesion is formed. The motion stage was programmed to move the HIFU transducer along a circular path of radius 0.75 cm, while HIFU was applied to a phantom (alginate dental impression material—Jeltrate™, Dentsply International, Milford, Del.) and RF data were collected during brief interruptions of HIFU delivery, and after therapy, as well. The therapy lasted 25 seconds, and RF data acquisition continued for an additional 50 seconds after HIFU delivery.

Maps of temperature induced strain ($\epsilon$) during therapy were generated by analysis of the RF data using the algorithm described above. The $\epsilon$ maps at four different time instants are shown in FIG. 19B, while the corresponding B-mode images are shown in FIG. 19A. The colorbar (a grey scale bar is illustrated, although the empirical data included full color) represents the magnitude of the induced strain towards the imaging transducer positioned above the image. Although no appreciable changes are seen on the B-mode images throughout therapy delivery and cool down, the $\epsilon$ maps clearly show the local temperature change induced by HIFU. As therapy progresses, the $\epsilon$ maps track the temperature rise along the scanning path of the HIFU transducer. These results demonstrate that local temperature changes induced by HIFU can be visualized by tracking changes in $\epsilon$ maps generated from the ultrasound backscatter signals.

To quantify the temperature induced strain over time, the amplitude and width of the strain profiles laterally along a test segment (R) were measured by fitting it to a Gaussian function. This test segment corresponded to the start of the HIFU transducer scanning path. The 1-D strain profiles are along segment R at five different time instants soon after HIFU therapy commenced were computed. The measured Gaussian radius and amplitude are shown in FIGS. 20 and 21, respectively. It can be seen that shortly after HIFU therapy commenced, the strain amplitude increased, consistent with the temperature rise. After a short time, the amplitude began to decrease, since the transducer had moved anti-clockwise, and was no longer depositing the heat at this location. The Gaussian radius increases with time during the course of HIFU therapy, due to thermal diffusion. These results demonstrate that the temperature induced strain maps provide an effective means of visualizing the thermal diffusion process. Furthermore, they illustrate the potential to extract quantitative temperature information by relating the strain information to a thermal diffusion model.

The empirical results show that analysis of the raw ultrasound backscatter provides improved visualization of lesion evolution by tracking the temperature rise compared to standard B-mode images. However, these techniques are qualitative in nature. Additional studies were performed to quantitatively compare temperatures estimated from the non-invasive ultrasound based technique with independent measurements made using thermocouples inserted in a tissue-mimicking phantom, in close proximity to the heat source, as described. A phantom was chosen instead of tissue for this preliminary experiment, so that the technique could be evaluated in a controlled setting. This experiment also served as a means for validating the strain estimation algorithm. The quantitative comparison was made in the temperature range 23-29° C. For this temperature range, the temperature induced strain is primarily due to the change in the speed of sound with the temperature, and the effect of thermal expansion can be ignored. To be able to invert the temperature induced strain data to obtain temperature, a separate experiment was performed to explicitly measure the relation between speed of sound and temperature. A detailed description of the experimental setup and the results is provided below.

An electrical heating element was employed in this experiment (instead of an acoustic heat source (i.e., HIFU)) to induce the temperature rise in the phantom. The main motivation in doing so for this preliminary experiment was to avoid the possibility that bubbles would be induced by acoustic cavitation, causing de-correlation artifacts in the RF data, and to focus on demonstrating the feasibility of obtaining quantitative temperature information from the ultrasound backscatter during heating with a controlled heat source. A tissue-mimicking gel made with polyacrylamide (and loaded with plastic microspheres to ensure scattering) was used as the phantom material for this experiment. Pre-gel polyacrylamide solution was prepared and poured into a custom-made sample holder (approximately a cube of 5 cm edges). A nichrome-chromium heating wire (available from Omega Engineering Inc., Stamford, Conn.) with a resistance of 1.6 Ohm/ft, was pulled taut through the center of the measurement cell. Four needle T-type thermocouples (available from Omega Engineering Inc., Stamford, Conn.) were carefully inserted into the gel, parallel to the heating wire. The thermocouples were placed at different radial distances from the wire, ranging from 4-11 mm. The exact distances of the thermocouples from the heating wire were measured using the ATL HDI 1000™ ultrasound scanner operating in the B-mode. The L11-5™ HDI 1000™ scan-head was rigidly mounted on the top of the measurement cell to acquire RF data during heating and cooling.

A DC voltage (supplied by "D" cell alkaline batteries, supplying ~6 V) was connected to the heating element, with a relay switch in series, to allow the heating circuit to be turned on and off remotely. The 4 thermocouples were connected to a data acquisition module (HP 34970™, available from Hewlett Packard Inc., Palo Alto, Calif.) to store the temperature readings in digitized form. The master control program for the ATL HDI 1000™ was modified for this experiment, to control the operation of the relay switch, to acquire temperature readings from the thermocouples using the data acquisition module, and to acquire the RF data using the ATL HDI 1000™. Such a data acquisition scheme ensured time-alignment between the invasive thermocouple measurements and non-invasive temperature estimation. A reference RF data frame was acquired before heating commenced. The relay switch was closed, and the heating circuit was activated. Instantaneously, the data acquisition module was initialized to begin acquisition of readings from the four thermocouples. RF data frames were acquired at intervals of 1 frame/sec during the heating phase. The relay switch was opened after 30 seconds to stop the heating phase. Acquisition of thermocouple readings continued at the same rate during the cooling phase, while RF data frames were acquired at a slower rate (a frame every 20 seconds) for an additional 2 minutes. The power dissipated in the heating element was constantly monitored by measuring the voltage and current in the circuit. The total power dissipation was approximately 15 W. The RF data were post-processed to obtain estimates of temperature induced strain, and the results were mapped to temperature, using the independently measured c(T) curves.

For the processing scheme employed in this validation experiment, it was necessary to obtain independent estimates of the c(T) curve, so that the measured temperature induced strain could be related to the c(T) mapping to temperature. It should be noted that since the contribution of thermal expansion is ignored, the c(T) mapping is the primary contribution to the mapping between strain and temperature. Furthermore, it should be recognized that the independent estimates of the c(T) curve were obtained for validation purposes only, and are not required for actual implementation of non-invasive techniques disclosed herein. Starting from an initial temperature of 22° C., speed of sound measurements were made using the sample substitution method, for every 10° C. rise in temperature. The experimental setup for the measurement is shown in FIG. 22. A broadband chirp pulse (1 MHz-10 MHz) with a duration 10 µs was applied to one of a pair of PVDF transducers placed across the sample immersed in a water bath heated with an electric heater. Thermocouples were placed in the water bath and also embedded in the sample. A spring-loaded assembly attached to the calipers ensured that the acoustic propagation distance through the sample was accurately measured throughout the experiment. The signal on the receiving transducer was digitized using an oscilloscope and stored for post-processing. The measurement setup was controlled remotely using custom software developed in Lab-VIEW™ (National Instruments, Austin, Tex.). At a given temperature, a reference measurement was first made in water by placing the transducer pair across the opening marked reference measurement. The transducer assembly was then placed across the sample, and a measurement was taken. The attenuation of the sample was computed by analyzing the frequency spectra of the signals received in water and the gel sample using the following equation, $$Attn(f) = \frac{|F_{ref}(f)|}{|F_{sample}(f)|} \quad (14)$$

where $F_{ref}(f)$ represents the FFT of the signal in the reference measurement, and $F_{sample}(f)$ represents the FFT of the signal in the sample measurement.

The attenuation versus frequency curve was used to equalize the signal received after propagation through the sample for use in the speed of sound calculation. By estimating the time shift between the signals received in the reference and sample, the speed of sound of the sample was calculated using the formula, $$c_t = \frac{1}{\frac{\Delta t}{d} + c_w} \quad (15)$$

where d=width of the sample, $c_w$=speed of sound in water at the temperature of measurement (known from reference data), and $c_t$=speed of sound in sample.

Before making a measurement at a given temperature, care was taken to ensure that thermal equilibrium was reached, by noting the readings of the thermocouples in the water bath and within the sample. FIG. 23 shows the c(T) curve measured for the gel phantom. Analysis of the RF data was performed using the algorithm developed above to compute changes in the speed of sound. By incorporating the c(T) curve information, temperature maps for the entire experiment were generated. The B-mode image was spatially registered to the temperature maps derived from the RF data, and thermocouple 1 was located on it. The time history of the temperature variation at that location was generated and is shown in FIG. 24. The temperature readings measured using thermocouples correspond to a curve 213, while the estimated temperatures using RF correspond to a curve 211. Good agreement between the measured values and the non-invasively estimated temperature values can be seen, with a maximum absolute error of approximately 2.5° C. Absolute errors of this magnitude would be acceptable over the therapeutic temperature range of interest. Results presented in this section demonstrate that quantitative temperature changes can be estimated non-invasively by analysis of the RF backscatter. The results show promise for extending the technique to obtain quantitative temperature information—which can be used as a method of monitoring HIFU therapy.

The discussion above shows that signal processing of raw ultrasound backscatter data can be used to generate maps of travel time changes (or temperature induced strain) for extracting temperature-related information. Direct inversion of travel time change to obtain quantitative temperature information requires explicit knowledge of the relationship between temperature induced strain ($\epsilon$) and temperature over the entire temperature range of interest. However, lack of sensitivity of speed of sound change to temperature near the tissue coagulation threshold (55°-60° C.) makes temperature estimation by direct inversion of the measured travel time shifts a challenging task. A solution to overcoming this problem of lack of sensitivity is to incorporate information about the underlying heat diffusion into the temperature estimation technique. The heat diffusion can be represented mathematically using the bio-heat transfer equation, parameterized with two constants, heating rate and the thermal diffusivity (for in vitro experimental conditions).

A model-based approach provides two direct advantages compared to a solely signal processing-based method relying on direct mapping of temperature induced strain ($\epsilon$) to temperature (T). First, by estimating the bio-heat transfer equation parameters using RF data collected immediately after HIFU therapy is turned on, only the region of high sensitivity in the $\epsilon(T)$ curve is used in the parameter estimation. After the bio-heat equation parameters have been estimated, the temperature field during the therapy can be computed numerically. Second, the spatial and temporal constraints imposed by the bio-heat equation can be used to regularize the temperature induced strain estimates, which avoids artifacts in the temperature maps due to smoothing and false peaks induced by processing the RF data.

Variability in the $\epsilon(T)$ relationship between tissue types and possibly between patients further complicates the inversion of temperature induced strain. For example, the speed of sound increases as a function of temperature for water-bearing tissues. However, for fatty tissue, the speed of sound actually decreases with temperature. It would therefore be desirable to have a non-invasive method of estimating this mapping in the treatment zone for use in clinical situations. Incorporating information about the underlying heat diffusion process using the bio-heat transfer equation enables the non-invasive estimation of the $\epsilon(T)$ relationship. Specifically, the temperature distribution at a calibration point (within the region of interest for HIFU therapy) can be first computed from the bio-heat equation using independently measured values for thermal diffusivity and heat source. The computed temperature distribution at this location can then be compared with the measured RF data to obtain the $\epsilon(T)$ curve. Thus, it can be seen that a heat transfer model-based temperature estimation approach can potentially overcome drawbacks associated with the low sensitivity and high variability of the $\epsilon(T)$ curve in the therapeutic temperature range. Much of the disclosure that follows focuses on the development and implementation of this non-invasive model-based temperature estimation technique. A detailed description of the technique and experimental results obtained in tissue-mimicking phantoms is provided below. Application of the methods to excised animal tissue is also described below.

The BHTE and Non-Invasively Measuring Two Parameters: The novelty of this concept that is disclosed herein lies in the ability to combine an underlying physical model based on the bio-heat equation (that describes the temperature evolution with non-invasive measurements of the ultrasound backscatter) to overcome the limitations associated with direct inversion of the ultrasound backscatter data, and thereby provide the capability to estimate tissue temperature over the entire therapeutic temperature range (i.e., from about (40°-80° C.). Thus, the techniques disclosed herein can be used as a tool for monitoring the progress of HIFU therapy. Combining the bio-heat equation with the backscattered ultrasound measurements for estimating temperature makes the technique robust. Previous methods have either been limited in their applicability to temperature ranges below the temperature range of interest for HIFU, or are based on simplifying presumptions regarding ($\delta(T)$), which introduces errors in the temperature estimation procedure.

As discussed above with respect to the high level flowcharts, the model-based temperature estimation algorithm disclosed herein is based on: (1) estimating the bio-heat equation parameters in situ using ultrasound backscatter data during a set of probe exposures performed before therapy begins in the region of interest; (2) non-invasive estimation of the relationship between acoustic travel time and temperature by combining forward computations of the bio-heat equation and the acoustic backscatter data acquired during the probe exposures; and, (3) during the therapy sessions, running forward computations of the model and adaptively updating the model parameters based on the received ultrasound backscatter. Additional details of this technique are provided below.

Bio-Heat Transfer Equation (BHTE): The basic law that relates the heat flow and the temperature gradient based on experimental observation was derived by Joseph Fourier around 1822. The general differential form of the heat transfer law is, $$rC\frac{\partial T}{\partial t} = -g(k-T) + f \tag{16}$$

where C is the specific heat capacity, k is the thermal conductivity, f represents the distributed source term, and T is the temperature.

In biological media, Eq. (16) cannot be applied directly, due to the complexity and the dynamics of the biological system. However, f can be expressed as a linear combination of heat sources and heat sinks. The internally generated heat sources that contribute to f include those related to metabolism, while the cooling processes are conduction, advection, and convection. The modified equation is referred to as the bio-heat transfer equation (BHTE). For the in vitro experimental procedures performed in developing the technology disclosed herein, the contribution of metabolism as a heat source, and convection and advection as heat sinks have been ignored. Hence the modified form of the BHTE becomes, $$\frac{\partial T}{\partial t} = K\nabla^2 T + Q' I(r,z) \tag{17}$$

where K is the thermal diffusivity ($m^2/sec$), given by $K=k/\rho C$, $Q(°C./s)$ represents the local in situ heating rate due to ultrasound energy absorption, $I(r,z)$ is the normalized spatial acoustic intensity distribution profile, r represents the axis perpendicular (transverse) to the direction of beam propagation, and z represents the beam propagation axis (longitudinal). The heating rate $Q(°C./s)$, and the heat energy deposition rate $Q'$ ($W/cm^3$) are related by the following equation, $$Q' = Q\rho C \tag{18}$$

In developing the techniques disclosed herein, the following assumptions are made regarding the parameters of the BHTE:

the tissue thermal properties, i.e., k and C are assumed to be spatially, and temporally invariant, and isotropic;
the thermal properties remain constant over the therapeutic temperature range; and a priori knowledge of the normalized (unit magnitude) spatial beam profile $I(r,z)$ is available (an experimentally measured beam profile or a simulated profile generated using a acoustic wave propagation code can be used).

It should be noted that for a HIFU heat source, Q' is a lumped quantity (referred to as the scaled local heat source) that is influenced by the attenuation along the beam path, local tissue absorption, and non-linear acoustic propagation effects. As used in the techniques disclosed herein, the emphasis is on estimating the lumped quantity, rather than the individual components.

The parameters K and Q' are individually estimated during two probe exposures immediately before the ablative therapy session begins. K is estimated during probe experiment 1, in which the sample is heated for a few seconds at a low intensity (sub-ablative), and then allowed to cool. The estimated value of K is then used in probe experiment 2, where the sample is quickly heated until a hyperechoic spot appears on the image. The time taken for the hyperechoic spot to appear is incorporated into the model to estimate the local heat source (Q'). Note that as discussed above, there are alternate techniques to conduct the Q' experiment, including using a thermal sensor and hydrophone to detect noise associated with the onset of boiling. FIG. 25 schematically illustrates exemplary overall steps.

Essential to the process are the two pre-therapy calibration steps that determine in situ values for BHTE parameters, K and Q. These two parameters can be measured at single points anywhere in the treatment region of interest and provide the characterization of local tissue and acoustic path properties necessary for accurate therapy planning and execution. The estimated parameters are then input into the BHTE to obtain temperature maps at the current location. The temperature estimates are related to strains estimated from the ultrasound backscatter during the calibration experiment, to obtain the non-invasive $\epsilon(T)$ mapping. It should be noted that once the BHTE parameters have been estimated at a given location using the calibration experiments, the temperature maps for that location can be obtained by computing the BHTE. It might thus appear that the estimation of $\epsilon(T)$ is not required, and the ultrasound backscatter information during monitoring is not needed either. However, such a technique is best suited for locations where the thermal parameter estimates are accurately known. The need for monitoring arises because tissue homogeneities result in local variation in the thermal parameters. Specifically, the present technique models the tissue heterogeneity variation in Q'. This assumption is based on prior dosimetry studies that demonstrated the variability in lesion widths while HIFU was applied to a uniform block of tissue, as the transducer was scanned along a circle at a constant velocity. The goal of the monitoring step is thus to accurately track these changes in Q'. The lower block in FIG. 25 illustrates the temperature monitoring step. The parameters estimated in the calibration step, K and $\epsilon(T)$, are passed on to this step. The therapy phase begins by following the planned experimental protocol and acquiring interleaved RF frames. These data are processed to compute the local strain and coupled with the BHTE to estimate the unknown heat source Q'. As can be clearly seen from the block diagram of FIG. 25, accurate knowledge of the $\epsilon(T)$ mapping is required to be able to compare the estimated strain with the predicted strain so that the heat source can be adaptively updated. This information can be used to modify the treatment protocol in real-time, to optimize safety and efficacy, while simultaneously minimizing treatment time.

FIGS. 26A-26C schematically illustrate how the proposed non-invasive model-based temperature estimation approach can be implemented in a clinical setting for therapy monitoring. First, the calibration experiments are performed at a single representative location within the treatment volume, to estimate the local acoustic and thermal parameters of interest (FIGS. 26A and 26B). After the calibration experiments have been completed, the therapy transducer is translated to a new location within the treatment region, and the HIFU therapy session commences (FIG. 26C). In this section, the estimation of K and Q are described in detail, along with results obtained in tissue-mimicking phantoms. The estimation of $\epsilon(T)$ and the temperature estimation step is explained in greater detail below.

The estimation of thermal diffusivity (K) is based on the principle of thermal clearance. In this approach, a short HIFU heating pulse is applied, and the resulting temperature distribution is measured. Sub-ablative HIFU intensities are employed, to ensure that the maximum temperature rise is no more than about 10°-15° C. The orientation of the HIFU transducer, the ultrasound imaging probe, and the geometric focus of the HIFU beam is schematically illustrated in FIG. 27. For an impulse HIFU heating pulse applied at time t=0, the resulting temperature distribution along the transverse direction r at z=0, after the HIFU pulse has been turned off, follows a Gaussian profile, which can be mathematically represented as:

$$T(r, t) - T_0 = \Delta T(r, t) = T_{max}(t) e^{\left[\frac{-r^2}{R(t)}\right]} \tag{19a}$$

where:

$$R(t) = 4K(t+\beta) \tag{19b}$$

In Eqs. (19a) and (19b), T(r,t) is the temperature distribution at distance r and time t, after the heating pulse was turned off, $T_{max}$ (° C.) represents the maximum temperature rise at time t, $T_0$ is the initial ambient temperature (typically 37° C.), R(t) (m²) is the Gaussian radius, K (m²/s) is the thermal diffusivity, and β(s) represents the diffusion time constant.

It has been demonstrated that in biological media, the temperature induced strain ($\epsilon$), measured from the ultrasound radio-frequency (RF) backscatter (due to changes in speed of sound) for temperature rises in the range of 10°-15° C. above ambient temperature, is directly proportional to the induced temperature change ($\Delta T(r,t)$):

$$\Delta T(r,t) = k\epsilon(r,t) \tag{20}$$

where k is a scalar constant.

From Eqs. (19a) and (20), the following relationship can be obtained:

$$\epsilon(r,t) = \epsilon_{max}(t) e^{-r^2/R(t)} \tag{21}$$

where $\epsilon_{max} = k T_{max}$.

Integrating Eq. (21) along r, the cumulative shift in the ultrasound RF echo locations s(r,t) along the imaging beam has the form of the error function (erf(x)):

$$s(r, t) = \int_{u=0}^{u=r} \varepsilon(u, t) du = A_{max}(t) \int_{u=0}^{u=r} e^{-u^2/R(t)} du \tag{22}$$

where $A_{max}(t)$ is the peak displacement at time t. From Eq. (22), it can be seen that the parameter R(t) can be measured from the Gaussian width of s(r,t) profiles for all times t. Differentiating Eq. (19b) with respect to t, yields:

$$\frac{d[R(t)]}{dt} = 4K \tag{23}$$

Eq. (23) shows that by computing the rate of change of R(t) versus t, the thermal diffusivity (K) can be estimated. The estimation procedure is non-invasive. It may be noted from Eq. (22) that errors introduced in the estimation of s(r,t) will affect the estimated R(t), and consequently, the thermal diffusivity K. The estimated value of K is used as a known quantity to then estimate the local heating rate Q, as described below.

Eq. (22) indicates that the echo location shifts s(r,t) can be represented by a closed functional form, and parameterized in terms of $A_{max}$ and R. In developing the technology disclosed herein, a novel parametric estimation approach is employed to estimate $A_{max}$ and R in Eq. (22) from the RF backscatter data collected during the HIFU experiment. A schematic representation of the estimation technique is presented in FIG. 28. Techniques for estimation of ultrasound echo location shifts s(r,t) between RF data frames acquired from a spatial region of interest that contains the HIFU focus have been previously used for ultrasound-based temperature estimation. However, the previous methods do not incorporate knowledge of the underlying physical heat diffusion mechanism in the estimation of the echo location shifts. The approach presented here allows direct estimation of thermal parameters, by iteratively relating the shift in the RF signals with a mathematical model describing the thermal diffusion process, without explicitly first estimating the strain, and then fitting the strain estimates to a physics-based mathematical model to derive the parameters of interest. The steps in the algorithm to compute R(t) between a pair of RF A-lines passing through the heated region, one acquired before heating commenced and one at $t=t_0$ (during cool down), are outlined below:

1. Mathematically model s(r,t), as indicated in Eq. (22), with unknown parameters $A_{max}$ and R, at a particular time $t_0$. $A_{max}$ and R are set to reasonable initial-guess values.
2. The RF line acquired at $t=t_0$ is temporally shifted by the magnitude of s(r,t) with values of $A_{max}$ and R set in step 1.
3. The shifted RF A-line (obtained at $t=t_0$) and preheated RF A-line are segmented into N non-overlapping segments and the normalized zero-lag correlation coefficient for each segment i is computed using Eq. (24), as noted below. A fixed value of N (typically 50) is chosen.

$$\sigma_i = \frac{\sum_{j=1}^{j=m} RF_{preheat}(j, i) * RF_{t=t_0}(j, i)}{\sqrt{\sum_{j=1}^{j=m} [RF_{preheat}(j, i)]^2 * \sum_{j=1}^{j=m} [RF_{t=t_0}(j, i)]^2}} \tag{24}$$

4. The error function err $$\sum_{i=1}^{i=N} (1 - \sigma_i)^2$$

is computed.

5. The parameters $A_{max}$ and R are updated to minimize err.
6. Steps 2, 3, 4, and 5 are repeated until err<(specified tolerance). The values of $A_{max}$ and R obtained after convergence are the best fit parameters. Typical plots of the zero-lag cross-correlation before and after convergence are shown in the bottom panel of FIG. 28. The zero-lag correlation drops significantly below unity after the focus location along depth. After convergence, the correlation coefficient improves to unity throughout the depth direction.

This procedure is repeated for all the RF frames collected during the cool down phase (after HIFU has been turned off), with respect to the frame acquired before heating commenced, to obtain values of R(t) corresponding to each frame. The optimization algorithm was implemented using the MATLAB™ (The Mathworks Inc., Natick, Mass.) function fminsearch, which is based on the Nelder-Mead Simplex search technique. The estimated values of R(t) are then fitted to a straight line, to obtain the local thermal diffusivity K, which is the thermal parameter of interest.

Experiments to validate the thermal diffusivity estimation algorithm were performed in a tissue-mimicking phantom made of alginate-based hydrogel, containing 95% water by weight. An experimental setup similar to that illustrated in FIG. 10B was employed. A 5 MHz HIFU therapy transducer (SU-104™, available from Sonic Concepts, Woodinville, Wash.) with an aperture diameter of 16 mm and a focal depth of 35 mm was used for delivering the HIFU heating pulse. The HIFU transducer was rigidly attached to a 3-D translation stage that allowed controlled motion in increments of 1 mm. The driving electronics for the HIFU transducer included a signal generator (HP 33120™, available from Hewlett Packard, Palo Alto, Calif.) driving a power amplifier (A300™, available from ENI, Rochester, N.Y.). The imaging probe used was the ATL CL10-5™ (Philips Medical Systems, Bothell, Wash.) with a bandwidth of 5 MHz to 10 MHz. Vertical alignment pins affixed to the base of the sample holder were used to co-register the HIFU beam propagation plane with the imaging plane. Specifically, before the experiment commenced, the HIFU transducer was operated in pulse-echo mode and translated using the motion stage until the received echo amplitude from the proximal alignment pin was maximized, thereby ensuring that the pins were in the HIFU focal plane. The imaging transducer was mounted on the sample holder, such that alignment pins were visible on B-mode images as straight lines, thus confirming that the imaging plane intersected the HIFU focal zone. RF data frames time-synchronized with the HIFU therapy delivery generation circuitry were acquired using the ATL HDI 1000™ ultrasound scanner during the brief HIFU heating phase lasting 5 seconds, and a cool down phase lasting 15 seconds. The RF data frames were acquired at a frame rate of 1 frame per second. A personal computer running a software program developed in Labview™ (National Instruments, Austin, Tex.) controlled the operation of the entire system. The RF data were transferred to the PC at the end of the experiment for offline data analysis. HIFU acoustic intensities were chosen such that the maximum temperature rise induced was approximately 10° C. The RF data sets were analyzed using the algorithm described above to compute R(t), and a least square fit was performed to estimate the thermal diffusivity K. The estimation procedure was tested on five phantom samples prepared using the same technique.

The thermal diffusivity (K) was also independently measured for the phantom samples using the transient hot-wire technique, a standard method for measuring the thermal properties of solids. The estimates obtained by this method were compared with those obtained using the non-invasive ultrasound-based estimation procedure.

The spatio-temporal temperature distribution radially outward from the heating wire is described by the following equations:

$$T(r, t) = -A \, Ei\left(-\frac{r^2}{4Kt}\right) \quad (25)$$

$$\text{where } A = \frac{q}{4\pi k}, \, Ei(-x) = -\int_x^\infty \frac{e^{-u}}{u} du \quad (26)$$

and where q represents the power (w) delivered per unit length of the wire, k represents the thermal conductivity (W/m/° C.), K is the thermal diffusivity (m²/s), r represents the radial distance away from the wire (m), and t represents the time (s) after heating commenced. Eq. (25) assumes that the heat source is infinitely long, with a negligible diameter, surrounded by an infinite solid. Eq. (26) was evaluated using the inbuilt function "expint" in MATLAB™ (The Mathworks Inc, Natick, Mass.). The thermocouple data were fitted to Eq. (25), and the unknown parameter A and thermal diffusivity K were estimated.

This procedure is repeated for all the RF frames collected during the cool down phase (after HIFU has been turned off) with respect to the frame acquired before heating commenced to obtain values of R(t) corresponding to each frame. The optimization algorithm was implemented using the MATLAB™ (The Mathworks Inc., Natick, Mass.) function fin-search, which is based on the Nelder-Mead Simplex search technique. The estimated values of R(t) are then fitted to a straight line to obtain the local thermal diffusivity K which is the thermal parameter of interest.

FIGS. 29A and 29B graphically illustrate model-derived s(r,t) and $\epsilon$(r,t) at various times after the HIFU heating pulse has been turned off, for a RF data set acquired in the alginate phantom (s(r,t) and $\epsilon$(rt) at times t=1 s (after heating pulse was turned off) through 19 s at intervals of 2 seconds for A-line passing through center of HIFU focal region; HIFU focus is at a depth of 0.021 m along the horizontal axis. Note $\epsilon$(r,t) follows the Gaussian shape, as expected from Eq. (21), and s(r,t) has the form of a "erf" function. It can be readily observed that the radius R of the Gaussian increases while the amplitude decreases, as time progresses after HIFU therapy is turned off This result is consistent with the temperature induced echo shift model represented by Eq. (22). After final convergence of the iterative strain estimation procedure, $\sigma_i$ is uniformly close to unity along depth, giving confidence in the model used to shift the post-heated RF line.

The estimated R(t) values are plotted as a function of time t in a least squares linear fit to the data points, based on Eq. (19b), as shown in FIG. 29C (i.e., a plot of the Gaussian radius R(t)² versus time t estimated from a RF data acquired in the alginate phantom). The straight line represents a least squares linear fit to the data points. Note the good agreement (r=0.96) of the data with the straight line model. K calculated using Eq. (23) was $1.72 \times 10^{-7}$ m²/s for this phantom sample. The mean estimate of K obtained non-invasively for the five phantom samples analyzed was $(1.7 \pm 0.07) \times 10^{-7}$ m²/s.

FIG. 29D graphically represents typical thermocouple profiles obtained during the transient hot wire experiments, and the superimposed analytical fit to the temperature data using Eq. (25). FIG. 29E graphically illustrates the residual error in the fit. The mean value of K estimated using this technique in four samples was $(1.44 \pm 0.2) \times 10^{-7}$ m²/s. A major source of uncertainty in the hot wire method is determining the exact distance between the thermocouples and the heating wire, and determining the orientation of the thermocouples. Since $r^2/4\alpha$ appears as a lumped term in Eq. (25), any errors in the measured distance impacts the estimated diffusivity. For example, an error of 0.2 mm in a thermocouple placed 2 mm from the wire results in an error of 20% in the estimated diffusivity. In addition, Eq. (25), which is used to fit the thermocouple temperature distribution, is based on a set of assumptions. It is assumed that the heating wire is an infinitely long line heat source. In addition, it is assumed that the thermal resistance between the heating wire and the sample at the outer edge of the wire is negligible, and that the specific heat capacity of the wire is also negligible. However, in the practical experimental setup employed, a heating wire of finite length was used. As a result, temperature distribution would not be radial close to the walls of the sample holder in the longitudinal direction. A thermal insulation layer between the outer boundary of the wire and the sample, possibly due to the creation of air cavities, could introduce significant thermal resistance, thereby reducing the rate at which the heat front propagates radially outward towards the thermocouples from the heating wire, which influences the thermal diffusivity estimate. The finite heat capacity of the heating wire implies that a finite time is required to first heat the wire, only after which the temperature rises in the sample, resulting in slower rate of temperature rise at the thermocouples. This factor is not accounted for by Eq. (25), and thus, would also bias the diffusivity estimate.

To validate the ultrasound RF-based estimation technique for the non-invasive estimation of K, simulation experiments were performed by generating RF A-lines during a HIFU heating experiment, and applying the iterative estimation technique described above. A random scatterer distribution was first generated with Gaussian distributed amplitudes, while the spacing between the scatterers was derived from a uniform distribution. Twenty scatterers per wavelength were generated to guarantee fully developed speckle. The temperature distribution due to ultrasonic absorption of HIFU energy over a 3 cm×2 cm 2-D region around the HIFU focus was computed using an axisymmetric finite element representation of the bio-heat equation (Eq. (17)), implemented in FEMLAB™ (Comsol AG, Sweden). A single element transducer with a geometric focal length of 35 mm and active diameter of 16 mm operating at 5 MHz was used as the HIFU therapy device. The normalized beam profile of the transducer simulated under linear acoustic conditions was used to represent the spatial distribution of the heat source. The HIFU therapy ON time was 5 s, while the cool-down phase was visualized for 15 s. The simulation parameters are listed in Table 1.

TABLE 1

Acoustic and Thermal parameters used to generate simulated RF lines for validation of ultrasound-based thermal diffusivity K estimation algorithm

| Parameter | Value |
| --- | --- |
| Center Frequency (MHz) | 8 MHz, 60% bandwidth |
| Scatterer Density | 20 per wavelength |
| Speed of sound (m/s) | 1540 |
| Ultrasonic SNR (dB) | 20 |
| Sampling Rate (MHz) | 32 |
| HIFU ON time (s) | 5 |
| HIFU Frequency (MHz) | 5 |
| Initial Temperature (° C.) | 25 |
| Thermal Conductivity (W/m/° C.) | 0.7 |
| Heat Capacity (J/kg/° C.) | 4180 |
| Density (kg/m$^3$) | 1000 |

The HIFU exposure intensity was chosen such that the maximum temperature reached after heating was not greater than 15° C. above ambient temperature (37° C.). The temperature maps were converted to equivalent speed of sound profiles using the mapping in FIG. 15 for liver tissue, which is a primary tissue of interest for HIFU treatment applications. The speed of sound profiles along the imaging beam were mapped to apparent displacements, and the new locations of the random scatterers were computed. For the ultrasound transmit system, the center frequency was 8 MHz with a fractional bandwidth of 60%. The transmit pulse was convolved with the scatterer profile to generate the RF A-lines. The SNR of the simulated RF signals was set to 20 dB, by adding white noise to represent realistic situations. RF frames were generated at a frame rate of 1 frame per second during the entire experiment. Fifty realizations of the simulation were performed to compute first and second order statistics.

For the estimation of K, signal analysis was performed along an RF A-line passing through the center of the HIFU focal zone (FIG. 23A). The echo location shifts s(r,t) and Gaussian radius R(t) were computed by processing each frame acquired during the cool down phase relative to the frame acquired before heating commenced.

The following provides yet another derivation for the estimation of K. The bio-heat equation for in vitro conditions can also be considered to be given by:

$$\frac{\partial T}{\partial t} = \left[\frac{k}{rC}\right]\tilde{N}g(\tilde{N}T) + \left[\frac{Q}{rC}\right]*I \quad (27)$$

The model parameters in the equation are the thermal diffusivity, represented by $$K = \frac{k}{rC}$$

(m$^2$/sec), and scaled local heat source, given by Q', where $$Q' = \frac{Q}{rC}.$$

Again, note that for a HIFU heat source, Q' is a lumped quantity that is influenced by the attenuation along the beam path, local tissue absorption and non-linear acoustic propagation effects.

In Eq. (27), setting the heat source to zero (representing tissue cooling), results in:

$$\frac{\partial T}{\partial t} = K\tilde{N}g(\tilde{N}T) \quad (28)$$

To solve the above equation numerically, a finite difference implementation will be adopted with forward differences used for the time derivative and central differences for the spatial derivatives.

2-D Cartesian coordinate geometry is chosen as an exemplary case for further simplifications. For this geometry, Eq. (28) can be represented in finite difference form as, $$T_{k+1}(x, z) = \tag{29}$$
$$T_k(x, z) + (K)\Delta t \left[ \frac{(T_k(x, z-1) - 2T_k(x, z) + T_k(x, z+1))}{(\Delta z)^2} + \frac{T_k(x-1, z) - 2T_k(x, z) + T_k(x+1, z)}{(\Delta x)^2} \right]$$

where x and z represent the lateral and axial dimensions respectively, $\Delta x$ and $\Delta z$ represent the grid spacing, $\Delta t$ represents the time step, and k is the time index. Typically, k and k+1 represent time instants when RF data was collected. Re-writing the equation for the next time step k+1 and subtracting Eq. (29) from it, a differential form of the equation that can be written as:

$$\Delta T_{k+1}(x, z) = \tag{30}$$
$$\Delta T_k(x, z) + (K)\Delta t \left[ \frac{(\Delta T_k(x, z-1) - 2\Delta T_k(x, z) + \Delta T_k(x, z+1))}{(\Delta z)^2} + \frac{\Delta T_k(x-1, z) - 2\Delta T_k(x, z) + \Delta T_k(x+1, z)}{(\Delta x)^2} \right]$$

where $\Delta T_k(x,z) = T_{k+1}(x,z) - T_k(x,z)$.

In the temperature range near body temperature (37°-50° C.), it has been shown that the change in temperature is proportional to the axial derivative of the echo location shifts, and can be represented by the following equation, $$DT_k = (\text{constant}) \frac{\partial(dt_{inc})}{\partial z} \tag{31}$$

Here, $\Delta T_k$ (i.e., $DT_k$) represents the change in temperature between frame k and k+1, while $\delta t_{inc}$ represents the corresponding integrated travel time change, and z is the depth direction. Substituting Eq. (31) into Eq. (30), and since $$\delta t_{local} = \frac{\partial(\delta t_{inc})}{\partial z},$$

Eq. (30) can be expressed in terms of local travel time shifts ($dt_{local}$) with the subscript$_{local}$ deleted for clarity, as:

$$\delta t_{k+1}(x, z) = \tag{32}$$
$$\delta t_k(x, z) + (K)\Delta t \left[ \frac{\delta t_k(x, z-1) - 2\delta t_k(x, z) + \delta t_k(x, z+1)}{(\Delta z)^2} + \frac{\delta t_k(x-1, z) - 2\delta t_k(x, z) + \delta t_k(x+1, z)}{(\Delta x)^2} \right]$$

From Eq. (32), it can be seen that the only unknown to solve for is the thermal diffusivity K. Since the local travel time change maps are typically 2-D matrices, Eq. (32) can be expressed in terms of a matrix equation as:

$$\text{Time Derivative} = K * \text{Laplacian} \tag{33}$$

with the terms in italics being 2-D matrices, where:

$$\text{Time Derivative} = \delta t_{k+1}(x,z) - \delta t_k(x,z) \tag{34}$$

and:

$$\text{Laplacian} = \left[ \frac{\delta t_k(x, z-1) - 2\delta t_k(x, z) + \delta t_k(x, z+1)}{(\Delta z)^2} + \frac{\delta t_k(x-1, z) - 2\delta t_k(x, z) + \delta t_k(x+1, z)}{(\Delta z)^2} \right] * \Delta t \tag{35}$$

are both known matrices. A least squares fitting approach is then applied to estimate the unknown parameter K. It is proposed that where the thermal source is HIFU, the finite difference equations will be computed using the axisymmetric 2-D geometry commonly employed. Thus, the procedure to estimate K for where the thermal source is HIFU includes the following steps: (1) heat the sample at sub-ablative intensities and allow the sample to cool down; (2) acquire ultrasound backscatter data at a frame rate of about 10 frames per second, and estimate travel time change maps from the backscatter data; and, (3) use Eq. (33) to estimate the thermal diffusivity using the travel time change data for the cooling phase.

Significantly, for the estimation of K, a first criteria is that a spatial temperature gradient must exist. Also, the source must approximate an impulse in both space and time. The sub-millimeter transverse beam width of the HIFU beam conveniently satisfies both requirements. In the empirical studies relating to K, the imaging scan-lines were oriented transverse to the HIFU beam. It is advantageous to image the temperature evolution in this direction, since the thermal gradients are greater, and hence, greater sensitivity to thermal diffusion exists in the ultrasound backscatter data.

Simulation results demonstrated that under realistic signal-to-noise conditions, K can be estimated with a variation of less than 10%. The estimates of K independently obtained using the invasive transient hot-wire method and the non-invasive method showed a difference of approximately 15%. A major source of uncertainty in the hot wire method is the distance between the thermocouples and the heating wire, and the orientation of the thermocouples. Significantly, other studies relating to thermal diffusivity indicate an expected uncertainty in thermal diffusivity measurements on the order of 30%. It should also be noted that the signal processing parameters employed in the empirical testing related to K, such as RF data sampling rate, transverse beam width of a HIFU transducer, cross-correlation window length (N in the equation) and thresholds in the optimization routines, were manually selected based on a priori knowledge and published literature values for similar signal analysis. A detailed error analysis could be performed to understand how the choice of these parameters affects the s(r,t) estimates, and consequently, K. Even without performing such optimization studies, the empirical data indicate the technique for estimating K non-invasively using RF data acquired during brief HIFU exposures at sub-ablative intensities is valid.

Note the A-line based RF processing scheme was adopted to estimate K, with the scan plane of the imaging transducer being oriented parallel to the HIFU beam propagation direction, to minimize the acoustic thermal lens effect (de-correlation in the RF signal due to refraction and refocusing of the beam during heating), because the thermal gradients laterally across the imaging beam are smaller at the center of the HIFU focal zone as compared to its edges. Extension of the A-line (1-D) based approach to a 2-D estimation technique performed over multiple adjacent scan lines in the heated region might benefit from incorporating the thermal lens effect in an appropriate numerical model to minimize model inconsistencies.

Estimation of Q': In this section, a novel non-invasive approach for estimating the local in situ heating rate Q' at the HIFU focus is described. The methodology is motivated by the fact that in HIFU treatments, focal heating rates on the order of 10° C. or more per second are commonly observed, and temperatures nearing boiling (100° C. at atmospheric pressure) have been reported. From Eq. (17), it can be observed that by measuring the rate of temperature rise at the therapeutic focus from ambient temperature to boiling (i.e., the term on the left side of Eq. (17)), and accounting for the temperature decay due to thermal conduction loss (the first term on the right side of Eq. (17)), the heating rate (Q') due to ultrasonic absorption can be estimated for a known spatial HIFU beam profile, I(x,y). In this technique, I(x,y) is computed a priori for the experimental HIFU transducer configuration, using a linear acoustic wave propagation tool, and is a constant throughout the procedure.

FIG. 30A graphically illustrates a typical representative plot of the temperature evolution at the geometric focus of a HIFU transducer, where the horizontal axis represents the time after heating commences, and $t_{boil}$ is the time (in seconds) to increase the temperature from ambient to boiling (assumed to be 100° C. for aqueous media), with $t_{boil}$ being measured experimentally during the HIFU exposure.

For a given known transducer geometry and spatial intensity beam profile, the time $t_{boil}$ required to raise the temperature of the tissue sample from ambient temperature to its boiling point can be non-invasively detected using a passive acoustic sensor sensitive to characteristic acoustic emissions (crackling and popping sounds related to the violent bursting of bubbles) in the audible frequency range (<20 KHz) that accompany boiling. Of course, a thermal sensor could be invasively disposed within the tissue mass; however, a non-invasive procedure is preferable, since HIFU therapy itself can be provided non-invasively. In this approach, starting with an initial estimated value for Q' and using the value of K estimated using the method described above, T(r,z,t) is computed iteratively using a finite element implementation of Eq. (17) to find the best estimate $Q_{est}$, such that T(r=0, z=0, t=$t_{boil}$)=100° C., where (r, z)=(0,0) represents the location of the HIFU focal spot.

For an independent validation, Q for the HIFU thermal source was also calculated using the following equation derived from HIFU parameters for linear acoustic propagation in an attenuating medium:

$$Q_{cal} = 2\alpha f I_{SP} e^{-(2\alpha f x)} \text{ W/cm}^3 \quad (36)$$

where α is the acoustic attenuation coefficient (Np/cm/MHz), $I_{SP}$ is the normalized spatial peak temporal average intensity (W/cm²), f is the HIFU frequency (MHz), and x represents the beam propagation distance (cm). Experimentally measured values for α and $I_{SP}$ were used to determine Q with Eq. (36). It was assumed that the absorption coefficient was equal to the attenuation coefficient, and losses due to scattering were negligible. The quantity $I_{SP}$ in Eq. (36) was determined using the following equation:

$$I_{SP} = 1.8 \cdot I_{SAL} \quad (37)$$

where:

$$I_{SAL} = \frac{0.683 \cdot W \cdot \eta}{\pi \cdot d^2}$$

and where $I_{SAL}$ represents the spatial average intensity (linear) (W/cm²), $I_{SP}$ represents the spatial peak intensity (W/cm²), W represents the electrical power input to the transducer (Watts), d represents the full width half maximum (FWHM) of the transducer (measured from the acoustic pressure profile (cm)), and η represents the electro-acoustic efficiency of the HIFU transducer. The parameters W, d, and η were measured during independent calibration experiments performed before the parameter calibration experiments.

To compare $Q_{cal}$ calculated using Eq. (36) to Q' determined using the non-invasive technique discussed above (i.e., the second calibration experiment), each value must be expressed in the same units, preferably (W/cm³) $Q_{est}$ was multiplied by the product of density (ρ) and specific heat (C), to ensure both values for the magnitude of the heat source were expressed in equivalent units.

A set of experiments was performed in alginate-based phantoms to validate the non-invasive technique for the estimation of Q' during HIFU exposures by measuring $t_{boil}$. A commercially available stethoscope was used as a passive sensor to detect the acoustic emissions in the audible frequency range (up to a few KHz) that are characteristic of the onset of boiling. The diaphragm of the stethoscope was attached to a microphone and placed against the alginate sample, on the far side from the HIFU transducer. The microphone output was sampled (using a sound card in the computing device being used for the system controller) at 44.1 KHz, and the samples were stored for offline processing. The total HIFU ON time was approximately 50 seconds, with brief interruption of the HIFU delivery (for 100 ms) every 0.5 s to enable acquisition of interference free B-mode images. The experiments were performed at in situ intensities ($I_{SAL}$) of 406 W/cm² and 523 W/cm². For each HIFU intensity, exposures were performed at five different spatial locations in a given sample, by translating the HIFU transducer along y and z directions using a 3-D motion stage. The treatment locations were separated by at least 1 cm, to avoid influence from sites already treated. For each of the exposures, the HIFU beam propagation was entirely within the sample. Bulk speed of sound and attenuation were measured for each of the samples.

Prior to the HIFU experiments, the operating characteristics of the HIFU transducer were measured and recorded. The full width half maximum (FWHM) distance (d) was determined to be approximately 0.91 mm. The electro-acoustic efficiency of the HIFU transducer was measured using a radiation force balance setup and was determined to be about 72.2%.

FIG. 30B graphically illustrates a typical time domain output of the stethoscope recorded during the HIFU exposure. At approximately t=10 s after the HIFU is turned on, a marked increase in the amplitude of the stethoscope output signal, due to acoustic emissions associated with the formation and collapse of bubbles related to boiling is seen. The periodic spikes every 2 seconds throughout the HIFU exposure are consistent with the HIFU beam being turned OFF and then ON after 100 ms, to capture RF data frames. This result is likely due to an acoustic radiation force-induced emission. The frequency domain representation (spectrogram) of the 700 Hz high-pass filtered time domain signal computed using the short time Fourier transform (STFT) is shown in FIG. 30C. The occurrence of strong broad-band signatures starting at t=30 s and extending in frequency up to 1.5 KHz corresponds to the onset of boiling. The power is computed from the spectrum of FIG. 30C by summing along the vertical axis at each time instant, as illustrated in FIG. 30D. This information can be used in an automated boiling detector to determine $t_{boil}$.

FIG. 30E graphically illustrates estimated boiling onset times for five independent exposures at two in situ HIFU intensities of 406 W/cm² and 523 W/cm². Good reproducibility in the boiling times for each of these intensities can be observed in this homogenous phantom sample. From the experimentally measured boiling times, $Q_{est}$ (W/cm³) was estimated using the techniques discussed above. In Table 2, the non-invasive estimate of the heat source along with the calculated value obtained using Eq. (36) is presented. A maximum difference of 20 percent is seen between $Q_{est}$ and $Q_{cal}$, with the calculated value higher at both intensities. This difference is likely due to the similar range of uncertainty in $Q_{cal}$, since it is dependent on the experimentally measured bulk acoustic attenuation of the sample, and the measured transducer characteristics, such as input electric power, electro-acoustic conversion efficiency, and the transducer beam profile.

TABLE 2

Comparison between non-invasively estimated in situ heat source ($Q_{est}$) and calculated heat source ($Q_{cal}$)

| Intensity [$I_{SAL}$] (W/cm²) | Estimated In-situ Q (W/cm³) ($Q_{est}$) | Calculated In-situ Q (W/cm³) ($Q_{cal}$) | % Difference ($Q_{cal} - Q_{est}$) × 100/$Q_{cal}$ |
|---|---|---|---|
| 406 | 291.97 | 325.75 | 10.53 |
| 523 | 308.74 | 389.73 | 20.78 |

The preceding disclosure describes novel non-invasive acoustical methods for estimating the in situ local thermal diffusivity (K) and the in situ heating rate (Q'). In the analysis described above, the medium being thermally treated was considered to be spatially homogenous and isotropic. In heterogeneous media, spatial variations in the thermal properties can be expected. To account for these spatial variations, measurements of K and Q' at a number of spatial locations within the region of interest can be repeated, and a spatial map of the thermal properties can be constructed. Significantly, the same transducer used for delivering the therapy dose can be used to determine the thermal parameters non-invasively. Application of the techniques to homogenous tissue-mimicking phantoms demonstrated the proof of principle.

The estimation of the heating rate Q' was based on first experimentally measuring the time required to raise the temperature of the focal point from ambient to boiling (assumed to be 100° C. in aqueous media), and applying the BHTE iteratively to compute the heating rate. The time series output of the stethoscope and the corresponding power spectrum in FIGS. 30B-30D illustrate that the $t_{boil}$ can be clearly detected. The boiling times measured within a given sample showed good reproducibility for both levels of acoustic intensities. This is consistent with the fact that the samples are prepared to be spatially homogeneous. $Q_{est}'$, obtained using the non-invasive technique, and $Q_{cal}$ (Eq. (36)) show a maximum difference of 20 percent, with the calculated value being higher than the estimated in both cases. This difference is on the order of the uncertainty in the measured values of attenuation ($\alpha$), and the spatial peak intensity ($I_{SP}$) in Eq. (36). Uncertainties in $I_{SP}$ result from measurements of the input electrical power, electro-acoustic efficiency, and the 6 dB beam width of the incident pressure field. The calculation also assumes that the attenuation coefficient is equal to the absorption coefficient.

Note that a linear acoustic propagation model was employed to compute the in situ beam profile I(r,z) used in Eq. (17), and $Q_{cal}$ in Eq. (36). However, the presence of acoustic nonlinearities has been previously reported for the intensity levels typically used in HIFU. The influence of the non-linearities in the magnitude of the local heating rate and its spatial intensity profile depend not only on the applied acoustic intensity, but also, on the intervening path attenuation. If the effect of non-linearities were only to influence the magnitude of the heating rate, while still maintaining the spatial profile close to the linear approximation, the estimated $Q_{est}$ would include this effect, since it is a free parameter in the fitting process. If the effect of non-linearities were strong enough to modify the local heat source spatial profile due to increased absorption of higher harmonics, $Q_{est}$ would be biased, since the estimation would be performed using an incorrect spatial heat source distribution profile. The effect of non-linearities can be explicitly included by employing a non-linear acoustic wave propagation model to compute the spatial intensity profile I(r,z) and the corresponding heating rate.

Alternate techniques for estimating Q' are briefly described below. It must be recognized that while the empirical studies disclosed herein emphasized HIFU therapy, the estimations of K and Q' as disclosed are also applicable to other thermal therapies, and to profiling tissue characteristics using different thermal sources (such as hot wires and cryogenic or other temperature sources). Thus, the HIFU application is intended to be exemplary, rather than limiting. With respect to estimating Q', where therapy is applied non-invasively, such as with HIFU, it is desirable to estimate Q' non-invasively. However, where the need for a non-invasive technique is not present, a thermal sensor can be inserted into the tissue mass (or placed adjacent to the tissue, to measure temperature directly, while recording the time required to reach a specific temperature). With respect to non-invasively estimating Q', in addition to using an acoustic sensor to detect the noise associated with the onset of boiling, an ultrasound image can be monitored to detect a hyperechoic spot that is also associated with the onset of boiling.

Thus, in one embodiment for estimating Q' for HIFU therapy, the tissue sample is heated rapidly so that boiling temperatures (~100° C.) are reached within 2-3 seconds. Ultrasound backscatter data are continuously acquired during the heating experiment, at about 10 fps. The time ($t_{100}$) measured since the start of heating, at which instant a hyperechoic spot (bright white region) on the B-mode image becomes visible (indicating boiling is occurring and the temperature in the tissue at the focal point of the HIFU beam is 100° C.) is thus determined. The ATL HDI-1000™ system discussed above provides a time stamp on each acquired frame relative to the start of the acquisition sequence. Thus, the onset of the hyperechoic spot can be accurately determined with good temporal resolution (~30 ms), enabling $t_{100}$ to be measured and used as an input parameter in an iterative algorithm used to estimate the heat source.

The iterative algorithm has been discussed above (with respect to estimating Q' by detecting noise associated with the onset of boiling). FIG. 30F is a flowchart showing exemplary steps of this iterative method. The inputs to the algorithm are the thermal diffusivity (K) previously determined as described above (i.e., probe experiment 1) and $t_{100}$ measured in probe experiment 2. The spatial intensity profile of the heat source distribution is assumed to be known a priori (obtaining such information of a HIFU therapy probe is not problematic, indeed, such data is generally useful to clinicians, and will often be available even when not required to implement the instant estimation of Q'). An initial estimated value for the heat source Q' is computed, assuming a linear rate of increase in temperature. The temperature distribution at $t_{100}$ is computed using Eq. (27) for these model parameter values, with the finite element solver FEMLAB™ (COMSOL Inc., Sweden). The heat source Q' is then adaptively updated using a minimization routine until the computed temperature in the focal region is 100° C. at time $t_{100}$.

Although the motivation for developing non-invasive methods to estimate the thermal diffusivity and the heat source was to be able to uniquely estimate the mapping between temperature and temperature induced strain ($\epsilon$) as shown in FIG. 25, the estimation methods disclosed herein can also be used in therapy planning applications, to predict the applied thermal dose at the treatment site, and accordingly decide on the treatment protocol. Current therapy planning procedures typically use values derived from the literature, or assumed standard values for the thermal diffusivity and local heating rate. However, these properties are tissue composition dependent and patient dependent. The availability of non-invasive in situ estimates at the treatment locations can reduce the uncertainty in the knowledge of these parameters and thus improve the accuracy of the predicted results. Note that within the limits of experimental uncertainties and model induced errors, the results from in vitro experiments performed in tissue-mimicking phantoms show good agreement between the non-invasive estimation techniques and independent validation procedures. The applicability of these techniques can be extended to assess the heterogeneity of biological tissue, and to construct spatial maps of the variation of these tissue specific parameters. Having discussed the estimating techniques for K and Q', the use of the estimated parameters to generate a temperature dependence curve calibrated to the tissue and thermal source is discussed below.

Using the BHTE, K, and Q': After the thermal properties (K and Q') have been estimated, temperature maps obtained by simulating the BHTE are related to the temperature induced strain c measured from the ultrasound backscatter to non-invasively obtain the mapping between temperature induced strain and temperature, referred to as $\epsilon(T)$. Then, using the estimated $\epsilon(T)$ mapping as a known quantity, temperature estimation is performed, as illustrated in FIG. 27. The following discussion focuses on the noninvasive estimation of $\epsilon(T)$, and the temperature estimation.

The relation between temperature induced strain ($\epsilon$) and temperature (T) incorporates the effect of the change of speed of sound versus temperature c(T) and thermal expansion. In the estimation procedure described herein, only the lumped quantity $\epsilon(T)$ is estimated. The goal is not to separate the contribution due to the speed of sound change and thermal expansion. The $\epsilon(T)$ relation is non-monotonic with temperature, and can be represented by a second-order polynomial of the form:

$$\epsilon(T)=bT^2+aT \quad (38)$$

where a,b represent scalar coefficients and T represents the temperature rise above the ambient value (typically 37 degrees C.). However, for a relatively small temperature rise of up to 10°-15° C. from ambient temperature, Eq. (38) can be approximated by a linear relation of the form:

$$\epsilon(T)=aT \quad (39)$$

In the context of the techniques disclosed herein, $\epsilon(T)$ corresponds to Eq. (39), because the parameter estimation for therapy monitoring is performed immediately (typically within 1 s) after HMFU therapy commences, while the maximum temperature rise is less than 15° C. Thus, the focus during the $\epsilon(T)$ estimation step is only on estimating the slope of the linear fit (parameter a). This parameter is determined by relating the echo shift between the first two RF frames acquired immediately after therapy commences, with simulated temperature maps at that location obtained using the BHTE. The flowchart of FIG. 31A illustrates the implementation of the $\epsilon(T)$ estimation algorithm. The estimation is performed using RF data collected during the calibration experiment (for determining Q').

The technique is implemented as an iterative optimization problem with the goal being to estimate the optimum value of parameter a for the given RF data set. An initial estimated value for parameter a is first selected. The BHTE equation is then evaluated using the values of K and Q' estimated from the calibration experiments, which provides the predicted temperature profiles for that particular location. The predicted temperature profiles are mapped into strain using $\epsilon(T)$, and then integrated along the depth direction to obtain the predicted echo shift. These echo shift estimates are then used to shift the samples of RF line RF(i). The RF lines RF(i) obtained after applying the echo shift and RF(i+1) are divided into a number of non-overlapping segments (typically each segment is 0.75 mm in length). The zero lag correlation p between corresponding segments on these RF lines is then computed as discussed above. The minimization function is computed as $(1-\rho)^2$ for each of the segments, and then summed to obtain the cumulative estimate. Parameter a is updated after each iteration, until the minimization function value is below a pre-defined threshold. It may be noted that although the temperature profiles for the current location can be directly evaluated based on knowledge of K and Q' without the need for explicit estimation of $\epsilon(T)$, this approach would not enable adaptively tracking changes in Q' during the therapy monitoring step. In order to be able to relate the BHTE predicted temperature maps with the RF backscatter data collected during therapy, $\epsilon(T)$ must be estimated, and thus, there is a need to carry out the steps outlined in FIG. 31A. It is assumed that $\epsilon(T)$ is spatially constant, and hence, the value estimated during the calibration step is used as a constant known parameter during therapy monitoring.

The experimental data used to validate the techniques for independent estimation of $\epsilon(T)$ were determined as part of the calibration procedures for K and Q' presented above. RF data were acquired and processed offline, based on the flowchart of FIG. 31A. It should be noted that the RF data collected during the boiling onset detection experiments were solely for use in the estimation of $\epsilon(T)$. The heat source (Q') and the thermal diffusivity (K) estimated during the calibration experiments are input into the BHTE to compute the predicted temperature profiles. In the empirical study, the value of Q was 291.72 W/cm³, while K was $1.7\times10^{-7}$ m²/s. The BHTE equation was implemented using the finite element technique in FEMLAB™ (Comsol AG, Stockholm, Sweden). The iterative algorithm in FIG. 31A was implemented using the MATLAB™ function fminsearch, which is an implementation of the Nelder-Mead simplex optimization technique. The analysis was performed on 10 adjacent RF A-lines passing through the center of the HIFU focal zone. The measurements were repeated at different test locations within two different phantom samples. The non-invasive estimates of $\epsilon(T)$ thus obtained were compared with invasive measurements of $\epsilon(T)$ independently obtained using the setup described below.

For independent validation of $\epsilon(T)$, the relationship was also measured using an invasive technique widely reported in the literature. The invasive estimates are considered ground truth measurements. These measurements are performed by tracking the echo shifts in the backscattered ultrasound when a sample is uniformly heated over the temperature range of interest, and $\epsilon(T)$ is computed from these echo shift estimates. A temperature-controlled water bath heating experiment was performed in order to uniformly characterize the $\epsilon(T)$ relationship of the alginate phantom sample. The sample was placed in a temperature-controlled water bath, with one thermocouple inserted into the phantom, and another immersed in the water bath. An electric heater with a built-in thermostat and circulator was immersed in the water bath, to uniformly heat the water bath and the sample. A commercial ultrasound imaging probe (L11-5™, Philips Medical Systems, Bothell, Wash.) was immersed in the water bath and oriented such that it imaged the sample. Care was taken to ensure that the imaging probe was not rigidly placed against the sample, so that the sample was free to expand. The water bath was heated in increments of approximately 10° C., and the thermostat on the water heater turned the heater off automatically, when a given preset temperature was reached. An RF data frame was collected using the ATL HDI-1000™ scanner at each temperature increment after ensuring that difference in the temperature readings between the two thermocouples was no greater than ±0.2° C.

FIG. 31B graphically illustrates RF echoes over an axial distance for a single scan-line, clearly showing echo shifts. The data from this validation experiment clearly show that the sensitivity of the temperature induced strain to temperature is greatest for temperatures close to ambient and body temperature. As the temperature rises above to 50° C., the sensitivity of the echo shifts to temperature decreases and reaches a plateau at about 70° C. Beyond 70° C., the echo shifts occur in the opposite direction, with the echoes moving away from the imaging transducer as the temperature rises. Thus, the best sensitivity for the estimation of parameters from the RF data is in the temperature range between 25°-55° C. From the echo shifts, the temperature induced strain was computed, and the mapping between strain and temperature ($\epsilon(T)$) is graphically illustrated in FIG. 31C (showing a polynomial fit to the data). Significantly, there is good correlation between the non-invasively estimated strain and the measured strain.

Having performed the strain estimation, that relationship can be used to perform non-invasive temperature estimations. The temperature estimation technique is based on non-invasive estimation of BHTE parameters. The non-invasive estimates of $\epsilon(T)$ obtained as indicated above are used as a known quantity in this step. A block diagram representation of the estimation technique is presented in FIG. 31D. It may be noted that the mapping between temperature and strain is modeled as a linear function in this estimation technique, because the iterations to estimate temperature by first estimating the BHTE parameter Q' are only performed on the initial frames (typically frames acquired within the first second after HIFU heating commences), and a linear model for $\epsilon(T)$ is valid in this range. Once Q' has been estimated using the initial set of frames, the BHTE is used to compute temperature throughout the exposure. This approach thus overcomes the limitations imposed by the low sensitivity of $\epsilon(T)$ over parts of the therapeutic temperature range of interest.

The technique is implemented as an iterative optimization problem as illustrated in FIG. 31D, with the goal being to estimate the optimum value of the parameter Q'. An initial estimated value for the parameter Q' is first selected. The BHTE equation is then evaluated using the values of K and Q' estimated from the calibration experiments, which gives the predicted temperature profiles for that particular location. The predicted temperature profiles are mapped to strain using the estimated parameter a, and then integrated along the depth direction to obtain the predicted echo shift. These echo shift estimates are then applied to shift the samples of RF line RF(i). The zero lag correlation p between the shifted RF line RF(i) and RF(i+1) is then computed by first dividing each of the RF lines into a number of non-overlapping segments. Parameter Q' is updated after each iteration until the minimization function is below a pre-defined threshold. The estimated value of Q' at convergence is then input into the BHTE to compute temperature maps at the site of the treatment. This approach is conceptually similar to that employed to estimate the parameter a, as described above.

The non-invasive temperature estimation technique was tested during in vitro experiments performed in the alginate tissue-mimicking phantom. Independent validation of the technique was performed by comparing the non-invasive temperature estimates with measurements from implanted thermocouples. A fixture enabling precise positioning of the HIFU probe and thermocouples was used. The thermocouples were precisely positioned around the geometric focus of the HIFU transducer, such that the thermocouples were located around the HIFU beam, where the temperature rises are significant, but yet not within the main lobe of the HIFU beam. This approach minimizes thermocouple artifacts caused by viscous heating effects in an ultrasound field that would affect the thermocouple readings. With this exemplary arrangement, the thermocouples are typically at transverse distances of 1, 3, and 4 mm from the HIFU beam propagation axis.

The master control program previously developed to collect RF data from the ATL HDI-1000™ commercial ultrasound scanner during HIFU therapy was modified so that the thermocouple readings could also be acquired simultaneously during the HIFU heating experiment. The thermocouples were connected to separate analog input channels on a computer controlled data acquisition unit (for example, an HP 34970™, available from Hewlett Packard, Palo Alto, Calif.). The sampling rate on each of the analog input channels was set to 10 Hz. Acquisition of thermocouple data was initiated at the start of HIFU therapy delivery, and continued during the cool-down period after HIFU delivery had been turned off. The total HIFU therapy delivery time was 7 seconds, with brief interruptions of 100 ms for acquiring RF data every 500 ms as described above. The in situ HIFU intensity for the exposures was 265 W/cm$^2$. The first two RF frames acquired immediately after therapy commenced (within the first 1 second) were used in the iterative estimation algorithm to determine the parameter Q'. The estimated values of Q' were then input in the BHTE to obtain the temperature maps. The experiments were performed starting at an initial baseline temperature of 29° C.

A comparison of the non-invasively estimated temperatures at the thermocouple locations (1, 3, and 4 mm from the HIFU beam propagation axis) and the corresponding thermocouple estimates is graphically illustrated in FIG. 31E. Note that there is no thermocouple data for the curve at the HIFU focus (since no thermocouples were positioned there), but the match between the thermocouple data and the non-invasively estimated data is excellent for the curves corresponding to 1, 3, and 4 mm from the HIFU beam propagation axis. Spatial maps of the temperature evolution around the HIFU focus were also computed and are shown in FIG. 31F, for the temperature evolution around the HTFU focus at times t=1, 2, 4, 7, and 8 s after the HIFU therapy delivery started. The HIFU therapy delivery was turned off at t=7.2 s. The color bar (if it were shown in color) represents the temperature rise in degrees Celsius above the ambient temperature. The HIFU transducer is at the top of spatial maps, and the beam propagates vertically downward. The comparison study demonstrates the ability of the temperature estimation algorithm to estimate temperatures in the therapeutic temperature range. The delivered thermal dose at the location of the maximum temperature rise for this case was 433 dose equivalent minutes, which exceeds the threshold for tissue necrosis of 120 minutes, referenced to 43° C. Furthermore, these results demonstrate that although the temperature induced strain lacks sensitivity over parts of the therapeutic temperature range, by combining information from the backscatter data with the BHTE, this limitation can be overcome.

A key difference between the current temperature estimation approach and previously reported methods is the coupling of the BHTE with echo shift information from the RF backscatter, to obtain the temperature information non-invasively. This approach enables estimation of temperatures in regions of low sensitivity of the $\epsilon(T)$ curve. Previously reported methods relied on direct inversion of $\epsilon$ via the $\epsilon(T)$ mapping to obtain temperature. However, since the $\epsilon(T)$ does not provide high sensitivity throughout the therapeutic temperature range, these prior art methods were only applicable in the low temperature range, where the sensitivity of the $\epsilon(T)$ curve was the greatest. In the current novel approach, the initial high sensitivity linear region of the $\epsilon(T)$ curve is used to non-invasively estimate the BHTE parameters. Once the BHTE parameters have been estimated, the BHTE is used to compute the temperature information throughout the HIFU exposure.

The estimation technique used in the novel approach assumes that the local in situ heat source $Q'$ does not change as a function of temperature, and that the value estimated at the beginning of treatment is valid throughout the exposure. The close agreement between the thermocouple measurements and the non-invasive temperature estimates appears to confirm this assumption. The local in situ heat source $Q'$ is a function of the local ultrasonic absorption coefficient and the intervening path attenuation.

An integral part of the temperature estimation technique is the non-invasive estimation of the mapping between temperature induced strain $\epsilon$ and temperature T. In previous studies, this mapping parameter was invasively determined prior to the therapy experiment. Such an invasive approach would not be effective in an in vivo clinical setting. Moreover, due to large scale variability in this parameter as a function of tissue type, it would be useful to estimate it for a given region of interest in the patient before the treatment commences. The non-invasive method proposed herein could be used for this purpose.

A related embodiment estimates temperatures by using the RF data to generate the $\delta(T)$ curve, rather than the strain curve. Such an embodiment is based on using the RF data to estimate the $\delta(T)$ curve. The calibration or probe experiments provide the necessary data, which are combined with the numerically computed temperature maps obtained by inserting the values for K and $Q'$ that were estimated during probe experiments 1 and 2, respectively, into Eq. (27), at the time instants when RF data were acquired. Travel time shifts are estimated from ultrasound backscatter data collected during probe experiment 2 (to estimate $Q'$). The travel time change data are then fitted against the simulated temperature maps to obtain an estimate of the $\delta(T)$ curve. This estimate of $\delta(T)$, obtained non-invasively, is assumed to be spatially invariant.

During therapy, temperature maps are obtained from forward computations of the bio-heat equation with the model parameters values initially set to the values for K and $Q'$ estimated in probe experiments. Because sample heterogeneities (especially in tissue) can result in changes to the local heat source ($Q'$), due to changes in attenuation caused by variations in beam propagation path and changes in local absorption, the technique to adaptively change the value of $Q'$ based on the backscatter data received is incorporated into therapy monitoring. The flowchart of FIG. 31G provides yet another explanation of the procedure to adaptively change $Q'$, using backscatter data acquired during the therapy. Estimates for $Q'$ and K derived from the probe experiments are used as initial inputs for the algorithm. The predicted temperature is mapped to equivalent travel time changes, using the $\delta(T)$ curve, and compared with the estimated travel time data derived from the ultrasound backscatter. The error between the estimated and simulated travel time change values is used to update $Q'$. The value of $Q'$ when the error is within a predefined tolerance level is then used in the bio-heat equation to obtain the temperature maps. Typically, the first two RF data frames acquired during therapy should be adequate to obtain the updated value of $Q'$, which can then be inserted into the bio-heat equation, to compute the temperature solution for the entire course of therapy.

The noninvasive temperature algorithm for HIFU therapy monitoring described above and empirically tested using alginate phantoms, was also tested using four different excised samples of turkey breast muscle. The K values determined for the samples were $1.42 \times 10^{-7}$, $1.18 \times 10^{-7}$, $1.3 \times 10^{-7}$, and $1.55 \times 10^{-7}$ m$^2$/s. The variation diffusivity values is likely due to the local heterogeneities, and inter-sample variability that would be expected between independent samples. For comparison, the reported value for thermal diffusivity in the literature for muscle is $1.4 \times 10^{-7}$ m$^2$/s. With respect to estimating $Q'$, a difference of approximately 18 percent between calculated values (using a priori measured parameters of the HIFU beam) and estimated values (based on detecting noise associated with the onset of boiling), closely matches the 20% variation discussed above, with respect to the alginate phantom validation, and can be explained by the similar range of uncertainties in the measured values of attenuation, electromechanical transducer efficiency, and applied electrical power. Comparing non-invasively determined temperature estimates during therapy with measurements obtained using thermocouples (generally as described above) yielded results similar to those graphically illustrated in FIG. 3E (i.e., provided a good agreement between the non-invasive in situ estimates and the data from the thermocouples inserted in the tissue). These results further demonstrate the applicability of ultrasound-based temperature estimates as described herein, for HIFU therapy monitoring. Such techniques appear to provide a viable alternative to MRI-based techniques, which are the gold standard for non-invasive thermometry during thermal ablation therapy in clinical use today.

The studies discussed above were based on in vitro conditions. The effect of tissue perfusion as a heat transport mechanism was therefore not considered, nor was external motion considered. To extend these techniques to in vivo conditions, the following potential complications should be considered: the effect of patient breathing, bulk motion of the transducer assembly (especially for freehand scanning), and the effect of perfusion. Given the short treatment times typically used in HIFU therapy, it can be expected that the effect of perfusion would likely be insignificant over the treatment duration. In cases where the effect is deemed to be significant enough (especially for highly perfused organs such as the liver) to be of concern, quantitative knowledge of the perfusion rate could be incorporated into the heat diffusion model, and determined during the calibration step. A non-invasive technique for determining perfusion has been recently proposed in the MRI imaging literature, and this approach can be extended to ultrasound data and used to estimate the perfusion rate as part of the calibration step. Potential techniques that could be applied for effective motion compensation are noted below.

The processing methods discussed above were based on 1-D analysis of the RF data. The echo shifts and temperature induced strain estimates were computed by processing a pair of RF lines from adjacent frames at the same lateral location. For model fitting, only the computed temperature estimates along a single axial scan line passing through the HIFU focal region were used. The techniques discussed above can be extended to 2-D processing. Thus, 2-D temperature maps obtained from the BHTE could be related to RF echo shifts determined using a 2-D cross-correlation algorithm, to estimate the thermal and acoustic parameters. If the 2-D data are properly pre-conditioned and filtered, such an approach can result in robust estimates of the parameters, since more independent data are used in the estimation analysis. However, care must be taken to properly account for the effect of acoustic beam-forming. Beam-forming errors could occur due to local thermal gradients within the width of the imaging beam, which could introduce artifacts distal to the heating zone and cause de-correlation effects in the RF signals. This effect is most severe at the extremities of the focal zone along the HIFU beam propagation direction, and less severe around the center of the heated region, where the thermal gradients are less severe. Methods for correcting the thermal lens artifact have been proposed and could be incorporated in the heat transfer model.

As discussed above, estimation of thermal and acoustic parameters were performed only over the initial portion of the $\epsilon(T)$ curve that could represented by a straight line ($\epsilon=aT$). These estimates were then used with the BHTE to compute the temperature maps. The limitation of such an approach is that the model does not permit the thermal parameters to change over time. Instead, once the thermal parameters have been estimated during the initial heating phase, they are assumed to be constant throughout the treatment. By modeling the $\epsilon(T)$ curve as a second order polynomial ($\epsilon=aT^2+bT$), information from the ultrasound backscatter can be related to the BHTE throughout the exposure, and the therapy parameters can also be updated throughout the exposure. This technique requires that all coefficients of the second order polynomial of the $\epsilon(T)$ curve be estimated accurately during the calibration step. For a single point lesion, only the region around the focal peak can be used to resolve the parameter a, since the higher temperatures only occur around a small region at the focus. This limitation introduces uncertainty in the estimates of a. However, if instead of a point lesion, a scanned lesion protocol is adopted, then the spatial extent of the temperature change will be greater, and will provide more spatial data to estimate a, thus improving its accuracy. This change also requires modification of the experimental protocol. However, the motivation to create scanned lesions in clinical HIFU practice is manifold, since the treatment throughput is greater and more cost effective. Modification of the estimation techniques to incorporate these changes could result in valuable improvement in the applicability of this non-invasive temperature estimation technique.

In clinical scenarios, bulk motion due to respiration and movement of the transducer during therapy, especially with freehand scanning, can influence the performance of time shift estimation techniques, such as those used herein to estimate the echo shifts and the temperature induced strain $\epsilon$. These motion effects typically include bulk translation, deformation, and rotation of tissue over regions much greater than the spatial extent of the heated zone. A possible technique for separating the artifacts would be to approach the concern as a two-step motion tracking problem. In the first step, block matching algorithms could be employed over regions of an RF image, to compensate for the motion effects. An appropriate signal-deformation model would need to be employed in this step. After the global bulk motion has been compensated, the BHTE model-based approach can be employed to estimate the temperature induced echo shifts, and inversely estimate the temperature. The advantage of using a BHTE model-based approach in such a scenario is that if bulk motion artifacts were not properly compensated, the iterative model-based approach would not converge, and the residuals of the minimization function would remain significant.

As noted above, it was assumed that the thermal and acoustic parameters are locally homogenous and isotropic. Hence, K, Q' in the BHTE equation, and $\epsilon(T)$ were scalars. It was further assumed that once K and $\epsilon(T)$ have been estimated during the calibration step, they can be assumed to be constant throughout the entire treatment region. Therefore, the results of the calibration step were used as known quantities during the monitoring step. In regions of large scale heterogeneity, as might be encountered in tissue regions with dense vasculature, it might be necessary to perform the calibration experiments at a number of different regions within the treatment volume to generate a spatial map of K and $\epsilon(T)$. This spatial map could then be used in the BHTE during the therapy monitoring step to obtain the non-invasive temperature information.

From the in situ measured temperature estimates during therapy, the applied thermal dose can be computed. This variable provides the ability to evaluate therapy progress and efficacy during the treatment, since the thermal dose has been shown to be a clinically effective indicator of the endpoint of ablative thermal therapy. The quantitative thermal dose estimates can be used to adaptively update the therapy delivery parameters, so that treatment efficacy is maximized. A feedback controller can be designed to update the applied heating rate, using information from the therapy monitoring system. Such control mechanisms have been previously applied for MRI thermometry-based dose optimization techniques. With the advent of ultrasound-based temperature estimation techniques, these adaptive control mechanisms can be applied on temperature information derived from ultrasound. Since the ultrasound data are acquired with greater temporal resolution, the approach can provide capability for improved therapeutic dose control in real-time.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for using ultrasound data to calibrate a biological tissue heat transfer model to a specific mass of tissue and a specific thermal source, comprising the steps of:
   (a) using the specific thermal source to change a temperature of the specific mass of tissue, and collecting a first set of ultrasound data as the specific mass of tissue returns to an ambient temperature;
   (b) using the first set of ultrasound data to determine a thermal diffusivity parameter corresponding to the specific mass of tissue;
   (c) using the specific thermal source to change a temperature of the specific mass of tissue to a predetermined value, while collecting a second set of ultrasound data and determining a length of time required to change the temperature of the specific mass of tissue to the predetermined value; and (d) using the thermal diffusivity parameter, the second set of ultrasound data, the length of time, and the biological tissue heat transfer model to determine a thermal source magnitude parameter corresponding to the specific thermal source and the specific mass of tissue, thereby calibrating the biological tissue heat transfer model to the specific thermal source and the specific mass of tissue.

2. The method of claim 1, further comprising the step of using the thermal source magnitude parameter, the thermal diffusivity parameter, the biological tissue heat transfer model, the first set of ultrasound data, and the second set of ultrasound data to generate a temperature dependence curve unique to the specific mass of tissue and the specific thermal source.

3. The method of claim 2, further comprising the step of using the temperature dependence curve to facilitate execution of at least one step selected from the group consisting essentially of:

(a) generating spatio-temporal temperature maps to facilitate pre-therapy planning of a thermal therapy; and (b) determining how long the specific thermal source should be used to change a temperature of the specific mass of tissue in order to deliver a desired thermal dose to the specific mass of tissue.

4. The method of claim 2, further comprising the steps of:

(a) using the specific thermal source to change the temperature of the specific mass of tissue to provide therapy to the specific mass of tissue;

(b) collecting a third set of ultrasound data during the therapy; and (c) using the third set of ultrasound data and the temperature dependence curve to estimate the temperature of the specific mass of tissue.

5. The method of claim 4, further comprising the steps of:

(a) using the thermal diffusivity parameter, the third set of ultrasound data, and the biological tissue heat transfer model to determine if the thermal source magnitude parameter has changed, and if so:

(i) updating the temperature dependence curve based on the updated value for the thermal source magnitude parameter to produce an updated temperature dependence curve; and (ii) using the third set of ultrasound data and the updated temperature dependence curve to estimate the temperature of the specific mass of tissue, thereby providing a more accurate temperature estimation.

6. The method of claim 2, further comprising the steps of:

(a) delivering a desired thermal dose to the specific mass of tissue by using the specific thermal source to change the temperature of the specific mass of tissue for a period of time required to achieve the desired thermal dose;

(b) collecting a third set of ultrasound data while the specific thermal source is delivering the desired thermal dose to the specific mass of tissue; and (c) using the thermal diffusivity parameter, the third set of ultrasound data, and the biological tissue heat transfer model to determine if the thermal source magnitude parameter has changed, and if so:

(i) updating the temperature dependence curve based on the updated value for the thermal source magnitude parameter to produce an updated temperature dependence curve;

(ii) determining how the updated temperature dependence curve affects the period of time required to achieve the desired thermal dose; and (iii) changing the period of time during which the specific thermal source is used to change the temperature of the specific mass of tissue as required to achieve the desired thermal dose, as a function of the effect of the updated temperature dependence curve.

7. The method of claim 2, wherein the step of using the thermal source magnitude parameter, the thermal diffusivity parameter, the biological tissue heat transfer model, the first set of ultrasound data, and the second set of ultrasound data to generate the temperature dependence curve unique to the specific mass of tissue and the specific thermal source comprises the steps of:

(a) generating a plurality of spatio-temporal temperature maps by inserting values for the thermal diffusivity parameter and the thermal source magnitude parameter into the biological tissue heat transfer model at time instances corresponding to the acquisition of at least the second set of ultrasound data;

(b) estimating travel time shifts from the second set of ultrasound data; and (c) fitting the time travel shifts to the spatio-temporal temperature maps to generate the temperature dependence curve.

8. The method of claim 1, further comprising the step of generating a plurality of spatio-temporal temperature maps by inserting values for the thermal diffusivity parameter and the thermal source magnitude parameter into the tissue heat transfer model at time instances corresponding to the acquisition of at least the second set of ultrasound data.

9. The method of claim 7, further comprising the step of using the spatio-temporal temperature maps for pre-therapy planning.

10. The method of claim 1, wherein the step of using the specific thermal source to change the temperature of the specific mass of tissue comprises the step of changing the temperature of the specific mass of tissue by about 5° C. to about 15° C.

11. The method of claim 1, wherein the step of using the first set of ultrasound data to determine the thermal diffusivity parameter comprises the step of processing the first set of ultrasound data to estimate a spatial width of a temperature distribution as a function of time.

12. The method of claim 11, wherein the step of processing the first set of ultrasound data comprises the steps of:

(a) determining an ultrasonic strain corresponding to a dissipation of thermal energy;

(b) fitting the ultrasonic strain to a Gaussian peak function; and (c) determining a rate of change of a Gaussian radius of the Gaussian peak function.

13. The method of claim 1, wherein the step of using the specific thermal source to change a temperature of the specific mass of tissue to the predetermined value comprises the step of using a thermal sensor inserted into the specific mass of tissue to determine when the predetermined value has been reached.

14. The method of claim 1, wherein the predetermined value is the boiling point of water, and wherein the step of using the thermal source to change the temperature of the specific mass of tissue to the predetermined value comprises at least one step selected from the group consisting essentially of:

(a) using an audio sensor to detect popping sounds associated with an onset of boiling to identify when the predetermined value has been reached; and (b) using ultrasound imaging to detect a hyperechoic spot in the specific mass of tissue to identify when the predetermined value has been reached.

15. The method of claim 1, wherein the step of using the thermal diffusivity parameter, the second set of ultrasound data, the length of time, and the tissue heat transfer model to determine a thermal source magnitude parameter corresponding to the specific thermal source and the specific mass of tissue comprises the step of determining the thermal source magnitude parameter by iteratively solving the tissue heat transfer model using the thermal diffusivity parameter, the second set of ultrasound data, and the length of time.

16. The method of claim 1, wherein the thermal source is selected from the group consisting essentially of:

(a) a high-intensity ultrasound transducer configured to raise a temperature of a portion of the specific mass of tissue sufficiently so as to cause tissue necrosis in the portion of the specific mass of tissue;

(b) a cryogenic source configured to lower a temperature of the specific mass of tissue for cryogenic therapy; and (c) a heat source configured to increase a temperature of the specific mass of tissue for heat-based therapy.

17. A method for using ultrasound data to determine a temperature dependence curve unique to a specific mass of tissue and a specific thermal source, thereby enabling temperature estimates as a function of time to be made for the specific mass of tissue and the specific thermal source, comprising the steps of:

(a) using the specific thermal source to change a temperature of the specific mass of tissue, and collecting a first set of ultrasound data as the specific mass of tissue returns to a previous temperature;

(b) using the first set of ultrasound data to determine a thermal diffusivity parameter corresponding to the specific mass of tissue;

(c) using the specific thermal source to change a temperature of the specific mass of tissue to a predetermined value, while collecting a second set of ultrasound data and determining a length of time required to change the temperature of the specific mass of tissue to the predetermined value;

(d) using the thermal diffusivity parameter, the second set of ultrasound data, the length of time, and a tissue heat transfer model to determine a thermal source magnitude parameter corresponding to the specific thermal source and the specific mass of tissue; and (e) using the thermal source magnitude parameter, the thermal diffusivity parameter, the tissue heat transfer model, the first set of ultrasound data, and the second set of ultrasound data to generate the temperature dependence curve unique to the specific mass of tissue and the specific thermal source.

18. The method of claim 17, further comprising the steps of:

(a) using the specific thermal source to change the temperature of the specific mass of tissue to provide therapy to the specific mass of tissue;

(b) collecting a third set of ultrasound data while providing the therapy; and (b) using time-of-flight data from the third set of ultrasound data and the temperature dependence curve to estimate the temperature of the specific mass of tissue.

19. The method of claim 18, further comprising the steps of:

(a) using the thermal diffusivity parameter, the third set of ultrasound data, and the biological tissue heat transfer model to determine if the thermal source magnitude parameter has changed; and if so, (b) updating the temperature dependence curve based on the updated value for the thermal source magnitude parameter to produce an updated temperature dependence curve; and (c) using time-of-flight data from the third set of ultrasound data, and the updated temperature dependence curve to more accurately estimate the temperature of the specific mass of tissue, thereby providing a more accurate temperature estimate.

20. The method of claim 17, wherein the step of using the thermal source magnitude parameter, the thermal diffusivity parameter, the tissue heat transfer model, the first set of ultrasound data, and the second set of ultrasound data to generate the temperature dependence curve unique to the specific mass of tissue and the specific thermal source comprises the steps of:

(a) generating a plurality of spatio-temporal temperature maps by inserting values for the thermal diffusivity parameter and the thermal source magnitude parameter into the tissue heat transfer model at time instances corresponding to the acquisition of at least the second set of ultrasound data;

(b) estimating travel time shifts from the second set of ultrasound data; and (c) fitting the time travel shifts to the spatio-temporal temperature maps to generate the temperature dependence curve.

21. The method of claim 20, further comprising the step of using the spatio-temporal temperature maps for pre-therapy planning.

22. The method of claim 17, further comprising the step of using the temperature dependence curve to facilitate execution of at least one step selected from the group consisting essentially of:

(a) generating spatio-temporal temperature maps to facilitate pre-therapy planning of a thermal therapy; and (b) determining how long the specific thermal source should be used to change a temperature of the specific mass of tissue in order to deliver a desired thermal dose to the specific mass of tissue.

23. The method of claim 17, further comprising the steps of:

(a) delivering a desired thermal dose to the specific mass of tissue by using the specific thermal source to change the temperature of the specific mass of tissue for a period of time required to achieve the desired thermal dose;

(b) collecting a third set of ultrasound data while the specific thermal source is delivering the desired thermal dose to the specific mass of tissue; and (c) using the thermal diffusivity parameter, the third set of ultrasound data, and the tissue heat transfer model to determine if the thermal source magnitude parameter has changed; and if so, (i) updating the temperature dependence curve based on the updated value for the thermal source magnitude parameter to produce an updated temperature dependence curve;

(ii) determining how the updated temperature dependence curve affects the period time required to achieve the desired thermal dose; and (iii) changing the period of time during which the thermal source is used to change the temperature of the specific mass of tissue as required to achieve the desired thermal dose, based upon an effect of the updated temperature dependence curve.

24. A system for selectively delivering a thermal therapy to a specific mass of tissue, comprising:
(a) a thermal source;
(b) an ultrasound imaging probe;
(c) means for identifying when the specific mass of tissue has reached a predetermined temperature; and
(d) a controller logically coupled to the thermal source, the ultrasound imaging probe, and the means for identifying when the specific mass of tissue has reached the predetermined temperature, the controller being configured to implement the functions of:
(i) using the thermal source to change a temperature of the specific mass of tissue, and collecting a first set of ultrasound data as the specific mass of tissue returns to a previous temperature;
(ii) using the first set of ultrasound data to determine a thermal diffusivity parameter corresponding to the specific mass of tissue;
(iii) using the thermal source to change a temperature of the specific mass of tissue to the predetermined value, while collecting a second set of ultrasound data, and determining a length of time required to change the temperature of the specific mass of tissue to the predetermined value; and
(iv) using the thermal diffusivity parameter, the second set of ultrasound data, the length of time, and a biological tissue heat transfer model to determine a thermal source magnitude parameter corresponding to the thermal source and the specific mass of tissue, thereby calibrating the biological tissue heat transfer model to the thermal source and the specific mass of tissue.

25. The system of claim 24, wherein the thermal source is selected from the group consisting essentially of:
(a) a high-intensity ultrasound transducer configured to raise a temperature of a portion of the specific mass of tissue sufficiently high so as to cause tissue necrosis in that portion of the specific mass of tissue;
(b) a cryogenic source configured to lower a temperature of the specific mass of tissue for administering cryogenic therapy; and
(c) a heat source configured to increase a temperature of the specific mass of tissue for administering heat-based therapy.

26. The system of claim 24, wherein the predetermined value is the boiling point of water, and wherein the means for identifying when the specific mass of tissue has reached the predetermined temperature comprises at least one means selected from the group consisting essentially of:
(a) an audio sensor, the audio sensor enabling a user to detect sounds indicative of an onset of boiling, the sounds thus indicating that the predetermined value has been reached; and
(b) the ultrasound imaging probe, a display, and the controller, the controller processing ultrasound data received from the ultrasound imaging probe to display an ultrasound image of the specific mass of tissue on the display, the display enabling a visualization of a hyperechoic spot in the specific mass of tissue, the hyperechoic spot indicating that the predetermined value has been reached.

27. The system of claim 24, wherein the means for identifying when the specific mass of tissue has reached the predetermined temperature comprises a thermal sensor configured to be positioned within the specific mass of tissue.

28. The system of claim 24, wherein the controller is further configured to implement the function of using the thermal source magnitude parameter, the thermal diffusivity parameter, the biological tissue heat transfer model, the first set of ultrasound data, and the second set of ultrasound data to generate a temperature dependence curve unique to the specific mass of tissue and the specific thermal source.

29. The system of claim 28, wherein the controller is further configured to implement at least one function selected from the group consisting essentially of:
(a) generating spatio-temporal temperature maps to facilitate pre-therapy planning of a thermal therapy; and
(b) determining how long the specific thermal source should be used to change a temperature of the specific mass of tissue in order to deliver a desired thermal dose to the specific mass of tissue.

30. The system of claim 28, wherein the controller is further configured to implement the functions of:
(a) controlling delivery of a desired thermal dose to the specific mass of tissue by using the thermal source to change the temperature of the specific mass of tissue for a period of time required to achieve the desired thermal dose;
(b) collecting a third set of ultrasound data while the thermal source is delivering the desired thermal dose to the specific mass of tissue; and
(c) using the thermal diffusivity parameter, the third set of ultrasound data, and the biological tissue heat transfer model to determine if the thermal source magnitude parameter has changed; and if so,
(i) updating the temperature dependence curve based on the updated value for the thermal source magnitude parameter to produce an updated temperature dependence curve;
(ii) determining how the updated temperature dependence curve affects the period of time required to achieve the desired thermal dose; and
(iii) changing the period of time during which the thermal source is used to change the temperature of the specific mass of tissue as required to achieve the desired thermal dose, as a function of an effect of the updated temperature dependence curve.

31. The system of claim 28, wherein the controller is further configured to implement the functions of:
(a) using the thermal source to change the temperature of the specific mass of tissue to provide therapy to the specific mass of tissue;
(b) collecting a third set of ultrasound data during the therapy; and
(b) using time-of-flight data from the third set of ultrasound data and the temperature dependence curve to estimate the temperature of the specific mass of tissue during therapy.

32. The system of claim 31, wherein the controller is further configured to implement the functions of:
(a) using the thermal diffusivity parameter, the third set of ultrasound data, and the biological tissue heat transfer model to determine if the thermal source magnitude parameter has changed; and if so,
(b) updating the temperature dependence curve based on the updated value for the thermal source magnitude parameter to produce an updated temperature dependence curve; and
(c) using time-of-flight data from the third set of ultrasound data and the updated temperature dependence curve to more accurately estimate the temperature of the specific mass of tissue, thereby providing a more accurate temperature estimation.

33. The system of claim 24, wherein the controller is further configured to implement the function of generating a plurality of spatio-temporal temperature maps obtained by inserting values for the thermal diffusivity parameter and the thermal source magnitude parameter into the tissue heat transfer model at time instances corresponding to the acquisition of the first set and the second set of ultrasound data.

34. A system for selectively delivering a thermal therapy to a specific mass of tissue, comprising:
  (a) a thermal source;
  (b) an ultrasound imaging probe;
  (c) means for identifying when the specific mass of tissue has reached a predetermined temperature; and
  (d) a controller logically coupled to the thermal source, the ultrasound imaging probe, and the means for identifying when the specific mass of tissue has reached the predetermined temperature, the controller being configured to implement the functions of:
    (i) using the thermal source to change a temperature of the specific mass of tissue, and collecting a first set of ultrasound data as the specific mass of tissue returns to a previous temperature;
    (ii) using the first set of ultrasound data to determine a thermal diffusivity parameter corresponding to the specific mass of tissue;
    (iii) using the thermal source to change a temperature of the specific mass of tissue to a predetermined value, while collecting a second set of ultrasound data, and determining a length of time required to change the temperature of the specific mass of tissue to the predetermined value;
    (iii) using the thermal diffusivity parameter, the second set of ultrasound data, the length of time, and a tissue heat transfer model to determine a thermal source magnitude parameter corresponding to the thermal source and the specific mass of tissue; and
    (iv) using the thermal source magnitude parameter, the thermal diffusivity parameter, the tissue heat transfer model, the first set of ultrasound data, and the second set of ultrasound data to generate the temperature dependence curve unique to the specific mass of tissue and the thermal source.

35. The system of claim 34, wherein the controller is further configured to implement the functions of:
  (a) using the thermal source to change the temperature of the specific mass of tissue to provide therapy to the specific mass of tissue;
  (b) collecting a third set of ultrasound data during the therapy; and
  (b) using the third set of ultrasound data and the temperature dependence curve to estimate the temperature of the specific mass of tissue during therapy.

36. The system of claim 34, wherein the controller is further configured to implement the functions of:
  (a) using the thermal diffusivity parameter, the third set of ultrasound data, and the biological tissue heat transfer model to determine if the thermal source magnitude parameter has changed; and if so,
  (b) updating the temperature dependence curve based on the updated value for the thermal source magnitude parameter to produce an updated temperature dependence curve; and
  (c) using the third set of ultrasound data and the updated temperature dependence curve to estimate the temperature of the specific mass of tissue, thereby providing a more accurate temperature estimation.

37. The system of claim 34, wherein the controller is further configured to implement the function of using the temperature dependence curve to determine how long the thermal source should be used to deliver a desired thermal dose to the specific mass of tissue.

38. The system of claim 34, wherein the controller is further configured to implement the functions of:
  (a) delivering a desired thermal dose to the specific mass of tissue by using the thermal source to change the temperature of the specific mass of tissue for a period of time required to achieve the desired thermal dose;
  (b) collecting a third set of ultrasound data while the thermal source is delivering the desired thermal dose to the specific mass of tissue; and
  (c) using the thermal diffusivity parameter, the third set of ultrasound data, and the biological tissue heat transfer model to determine if the thermal source magnitude parameter has changed; and if so,
    (i) updating the temperature dependence curve based on the updated value for the thermal source magnitude parameter to produce an updated temperature dependence curve;
    (ii) determining how the updated temperature dependence curve affects the period time required to achieve the desired thermal dose; and
    (iii) changing the period of time during which the thermal source is used to change the temperature of the specific mass of tissue as required to achieve the desired thermal dose, as a function of an effect of the updated temperature dependence curve.

\* \* \* \* \*